United States Patent
Bruenker et al.

(10) Patent No.: US 9,481,730 B2
(45) Date of Patent: Nov. 1, 2016

(54) DR5—FAP BISPECIFIC DEATH RECEPTOR AGONISTIC ANTIBODIES

(75) Inventors: Peter Bruenker, Hittnau (CH);
Claudia Ferrara Koller, Zug (CH);
Sandra Grau, Birmensdorf (CH);
Sylvia Herter, Regensdorf (CH);
Christoph Lampert, Zurich (CH);
Ekkehard Moessner, Kreuzlingen (CH); Pablo Umana, Wollerau (CH);
Inja Waldhauer, Urdorf (CH)

(73) Assignee: Roche Glycart AG, Schlieren (CH)

( * ) Notice: Subject to any disclaimer, the term of this patent is extended or adjusted under 35 U.S.C. 154(b) by 94 days.

(21) Appl. No.: 13/498,390

(22) PCT Filed: Sep. 27, 2010

(86) PCT No.: PCT/EP2010/064209
§ 371 (c)(1),
(2), (4) Date: Mar. 27, 2012

(87) PCT Pub. No.: WO2011/039126
PCT Pub. Date: Apr. 7, 2011

(65) Prior Publication Data
US 2012/0184718 A1   Jul. 19, 2012

(30) Foreign Application Priority Data
Sep. 29, 2009 (EP) .................... 09171659

(51) Int. Cl.
| | |
|---|---|
| C07K 16/30 | (2006.01) |
| C07K 16/28 | (2006.01) |
| C07K 16/18 | (2006.01) |
| C07K 16/40 | (2006.01) |
| C07K 14/715 | (2006.01) |
| C12N 9/00 | (2006.01) |

(52) U.S. Cl.
CPC ........... *C07K 16/2878* (2013.01); *C07K 16/18* (2013.01); *C07K 16/30* (2013.01); *C07K 16/3007* (2013.01); *C07K 16/40* (2013.01); *C07K 2317/31* (2013.01); *C07K 2317/73* (2013.01)

(58) Field of Classification Search
None
See application file for complete search history.

(56) References Cited

U.S. PATENT DOCUMENTS

| | | | |
|---|---|---|---|
| 5,580,774 | A | 12/1996 | Beavers et al. |
| 5,965,710 | A | 10/1999 | Bodmer et al. |
| 7,632,497 | B2 * | 12/2009 | Stavenhagen |
| 8,029,783 | B2 * | 10/2011 | Adams et al. |

(Continued)

FOREIGN PATENT DOCUMENTS

| | | |
|---|---|---|
| EP | 1 870 459 A1 | 12/2007 |
| WO | 02/08291 | 1/2002 |

(Continued)

OTHER PUBLICATIONS

Hermann et al., Construction of optimized bispecific antibodies for selective activation of the death receptor CD95, Canc. Res. 68(4):1221-1227, Feb. 2008.*

(Continued)

*Primary Examiner* — Claire Kaufman

(57) ABSTRACT

The present invention relates to bispecific antibodies comprising a first antigen binding site specific for a death receptor and a second antigen binding site specific for a second antigen, methods for their production, pharmaceutical compositions containing said antibodies, and uses thereof.

9 Claims, 20 Drawing Sheets

(56) References Cited

U.S. PATENT DOCUMENTS

| | | | |
|---|---|---|---|
| 9,011,847 | B2 | 4/2015 | Bacac et al. |
| 2003/0232049 | A1* | 12/2003 | Jung |
| 2004/0033511 | A1* | 2/2004 | Pfizenmaier et al. |
| 2007/0031414 | A1 | 2/2007 | Adams |
| 2014/0370019 | A1 | 12/2014 | Bruenker et al. |

FOREIGN PATENT DOCUMENTS

| | | |
|---|---|---|
| WO | 02/085946 | 10/2002 |
| WO | 2005/092927 | 10/2005 |
| WO | 2006/074397 | 7/2006 |

OTHER PUBLICATIONS

Carter, P., Bispecific human IgG by design, J. Immunol. Meth. 248:7-15, 2001.*
Booy et al., Monoclonal and bispecific antibodies as novel therapeutics, Arch. Immunol. Ther. Exp. 54:86-101, 2006.*
Marvin et al., Recombinant approaches to IgG-like bispecific antibodies, Acta Pharmacologica Sinica, 26(6):649-458, Jun. 2005.*
Kriangkum et al., Bispecific and bifunctional single chain recombinant antibodies, Biomolecular Engineering, 18:31-40, 2001.*
Wu et al., Simultaneous targeting of multiple disease mediators by a dual-variable-domain immunoglobulin, Nat. Biotech. 25(11):1290-1297, Nov. 2007.*
Asano et al., Protein structure and folding: Highly effective recombinant format of a humanized IGG-like bispecific antibody for ancer immunotherapy with regarging of lymphocytes to tumor cells, J. Biol. Chem. 282:27659-27665, Jul. 2007.*
Michaelson et al., Anti-tumor activity of stability-engineered IgG-like bispecific antibodies targeting TRAIL-R2 and LTβR, mAbs, 1(2):128-141, DOI: 10.4161/mabs.1.2.7631, Mar. 2009.*
Melero et al., Immunostimulatory monoclonal antibodies for cancer therapy, Nat. Rev. Canc. 7:95-106, Feb. 2007.*
IPER for PCT/EP2010/064209 (W02011039126) (Date Issued Apr. 3,2012).
ISR for PCT/EP2010/064209 (WO2011039126) (Mailing Date Feb. 2, 2011).
Michaelson et al., "Anti-tumor activity of stability-engineered IgG-like bispecific antibodies :targeting TRAIL-R2 and LTβR." MAbs (e-pub. Mar. 11, 2009), 1(2):128-141 (Mar. 2009).
Ridgway et al., "'Knobs-into-holes' Engineering of Antibody CH3 Domains for Heavy Chain Heterodimerization" Protein Eng 9(7):617-621 ( 1996).
Written Opinion for PCT/EP2010/064209 (WO2011039126) (Date of Mailing Feb. 2, 2011).
Wuest et al., "Construction of a bispecific single chain antibody for recruitment of cytotoxic T cells to the tumour stroma associated antigen fibroblast activation protein" J Biotechnol 92:159-168 ( 2001).
Hermann et al., "Construction of Optimized Bispecific Antibodies for Selective Activation of the Death Receptor CD95" Cancer Res 68(68):1221-1227 (Feb. 15, 2008).
Jung et al., "Target Cell-restricted Triggering of the CD95 (APO-1/Fas) Death Receptor with Bispecific Antibody Fragments" Cancer Res (61)5:1846-1848 ( 2001).
MacFarlane et al., "Identification and Molecular Cloning of Two Novel Receptors for the Cytotoxis Ligand TRAIL," Journal of Biological Chemistry 272:25417-25420 ( 1997).
Marsters et al., "A Novel Receptor for Apo2L/TRAIL Contains a Truncated Death Domain" Current Biology 7:1003-1006 (Oct. 6, 1997).
Ridgway et al., "'Knobs-into-holes' engineering of antibody CH3 domains for heavy chain heterodimerization" Protein Engineering 9(7):617-621 ( 1996).
Samel et al., "Generation of a FasL-based Proapoptotic Fusion Protein Devoid of Systemic Toxicity due to Cell-surface Antigen-restricted Activation" J. Biol. Chem. 278(34):32077-32082 (May 28, 2003).
Simonet et al., "Osteoprotegerin: A Novel Secreted Protein Involved in the Regulation of Bone Density" Cell 89:309-319 ( 1997).
Wagner et al., "Death Receptor O-Glycosylation Controls Tumor-Cell Sensitivity to the Proapoptotic Ligand Apo2L/TRAIL" Nature Medicine 13(9):1070-1077 (Sep. 2007).
Wajant et al., "Differential Activation of TRAIL-R1 and -2 by Soluble and Membrane TRAIL Allows Selective Surface Antigen-directed Activation of TRAIL-R2 by a Soluble TRAIL Derivative" Oncogene 20:4101-4106 (Apr. 19, 2001).

* cited by examiner

SEQUENCE LISTING

```
<160> NUMBER OF SEQ ID NOS: 9

<210> SEQ ID NO 1
<211> LENGTH: 468
<212> TYPE: PRT
<213> ORGANISM: Homo sapiens

<400> SEQUENCE: 1

Met Ala Pro Pro Pro Ala Arg Val His Leu Gly Ala Phe Leu Ala Val
1               5                   10                  15

Thr Pro Asn Pro Gly Ser Ala Ala Ser Gly Thr Glu Ala Ala Ala Ala
                20                  25                  30

Thr Pro Ser Lys Val Trp Gly Ser Ser Ala Gly Arg Ile Glu Pro Arg
            35                  40                  45

Gly Gly Gly Arg Gly Ala Leu Pro Thr Ser Met Gly Gln His Gly Pro
        50                  55                  60

Ser Ala Arg Ala Arg Ala Gly Arg Ala Pro Gly Pro Arg Pro Ala Arg
65                  70                  75                  80
```

```
Glu Ala Ser Pro Arg Leu Arg Val His Lys Thr Phe Lys Phe Val Val
                85                  90                  95
Val Gly Val Leu Leu Gln Val Val Pro Ser Ser Ala Ala Thr Ile Lys
            100                 105                 110
Leu His Asp Gln Ser Ile Gly Thr Gln Gln Trp Glu His Ser Pro Leu
        115                 120                 125
Gly Glu Leu Cys Pro Pro Gly Ser His Arg Ser Glu His Pro Gly Ala
    130                 135                 140
Cys Asn Arg Cys Thr Glu Gly Val Gly Tyr Thr Asn Ala Ser Asn Asn
145                 150                 155                 160
Leu Phe Ala Cys Leu Pro Cys Thr Ala Cys Lys Ser Asp Glu Glu Glu
                165                 170                 175
Arg Ser Pro Cys Thr Thr Thr Arg Asn Thr Ala Cys Gln Cys Lys Pro
            180                 185                 190
Gly Thr Phe Arg Asn Asp Asn Ser Ala Glu Met Cys Arg Lys Cys Ser
        195                 200                 205
Arg Gly Cys Pro Arg Gly Met Val Lys Val Lys Asp Cys Thr Pro Trp
    210                 215                 220
Ser Asp Ile Glu Cys Val His Lys Glu Ser Gly Asn Gly His Asn Ile
225                 230                 235                 240
Trp Val Ile Leu Val Val Thr Leu Val Val Pro Leu Leu Leu Val Ala
                245                 250                 255
Val Leu Ile Val Cys Cys Cys Ile Gly Ser Gly Cys Gly Gly Asp Pro
            260                 265                 270
Lys Cys Met Asp Arg Val Cys Phe Trp Arg Leu Gly Leu Leu Arg Gly
        275                 280                 285
Pro Gly Ala Glu Asp Asn Ala His Asn Glu Ile Leu Ser Asn Ala Asp
    290                 295                 300
Ser Leu Ser Thr Phe Val Ser Glu Gln Gln Met Glu Ser Gln Glu Pro
305                 310                 315                 320
Ala Asp Leu Thr Gly Val Thr Val Gln Ser Pro Gly Glu Ala Gln Cys
                325                 330                 335
Leu Leu Gly Pro Ala Glu Ala Glu Gly Ser Gln Arg Arg Arg Leu Leu
            340                 345                 350
Val Pro Ala Asn Gly Ala Asp Pro Thr Glu Thr Leu Met Leu Phe Phe
        355                 360                 365
Asp Lys Phe Ala Asn Ile Val Pro Phe Asp Ser Trp Asp Gln Leu Met
    370                 375                 380
Arg Gln Leu Asp Leu Thr Lys Asn Glu Ile Asp Val Val Arg Ala Gly
385                 390                 395                 400
Thr Ala Gly Pro Gly Asp Ala Leu Tyr Ala Met Leu Met Lys Trp Val
                405                 410                 415
Asn Lys Thr Gly Arg Asn Ala Ser Ile His Thr Leu Leu Asp Ala Leu
            420                 425                 430
Glu Arg Met Glu Glu Arg His Ala Lys Glu Lys Ile Gln Asp Leu Leu
        435                 440                 445
Val Asp Ser Gly Lys Phe Ile Tyr Leu Glu Asp Gly Thr Gly Ser Ala
    450                 455                 460
Val Ser Leu Glu
465

<210> SEQ ID NO 2
<211> LENGTH: 440
```

```
<212> TYPE: PRT
<213> ORGANISM: Homo sapiens

<400> SEQUENCE: 2

Met Glu Gln Arg Gly Gln Asn Ala Pro Ala Ser Gly Ala Arg Lys
1               5                   10                  15

Arg His Gly Pro Gly Pro Arg Glu Ala Arg Gly Ala Arg Pro Gly Leu
                20                  25                  30

Arg Val Pro Lys Thr Leu Val Leu Val Val Ala Ala Val Leu Leu Leu
                35                  40                  45

Val Ser Ala Glu Ser Ala Leu Ile Thr Gln Gln Asp Leu Ala Pro Gln
    50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
                100                 105                 110

Cys Leu Arg Cys Thr Arg Cys Asp Ser Gly Glu Val Glu Leu Ser Pro
                115                 120                 125

Cys Thr Thr Thr Arg Asn Thr Val Cys Gln Cys Glu Glu Gly Thr Phe
    130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Thr Lys His Ser Gly Glu Ala Pro
                180                 185                 190

Ala Val Glu Glu Thr Val Thr Ser Ser Pro Gly Thr Pro Ala Ser Pro
                195                 200                 205

Cys Ser Leu Ser Gly Ile Ile Ile Gly Val Thr Val Ala Ala Val Val
    210                 215                 220

Leu Ile Val Ala Val Phe Val Cys Lys Ser Leu Leu Trp Lys Lys Val
225                 230                 235                 240

Leu Pro Tyr Leu Lys Gly Ile Cys Ser Gly Gly Gly Gly Asp Pro Glu
                245                 250                 255

Arg Val Asp Arg Ser Ser Gln Arg Pro Gly Ala Glu Asp Asn Val Leu
                260                 265                 270

Asn Glu Ile Val Ser Ile Leu Gln Pro Thr Gln Val Pro Glu Gln Glu
                275                 280                 285

Met Glu Val Gln Glu Pro Ala Glu Pro Thr Gly Val Asn Met Leu Ser
    290                 295                 300

Pro Gly Glu Ser Glu His Leu Leu Glu Pro Ala Glu Ala Glu Arg Ser
305                 310                 315                 320

Gln Arg Arg Arg Leu Leu Val Pro Ala Asn Glu Gly Asp Pro Thr Glu
                325                 330                 335

Thr Leu Arg Gln Cys Phe Asp Asp Phe Ala Asp Leu Val Pro Phe Asp
                340                 345                 350

Ser Trp Glu Pro Leu Met Arg Lys Leu Gly Leu Met Asp Asn Glu Ile
                355                 360                 365

Lys Val Ala Lys Ala Glu Ala Ala Gly His Arg Asp Thr Leu Tyr Thr
                370                 375                 380

Met Leu Ile Lys Trp Val Asn Lys Thr Gly Arg Asp Ala Ser Val His
385                 390                 395                 400
```

```
Thr Leu Leu Asp Ala Leu Glu Thr Leu Gly Glu Arg Leu Ala Lys Gln
                405                 410                 415

Lys Ile Glu Asp His Leu Leu Ser Ser Gly Lys Phe Met Tyr Leu Glu
            420                 425                 430

Gly Asn Ala Asp Ser Ala Met Ser
        435                 440

<210> SEQ ID NO 3
<211> LENGTH: 335
<212> TYPE: PRT
<213> ORGANISM: Homo sapiens

<400> SEQUENCE: 3

Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Lys Glu Val Gln Lys Thr Cys Arg Lys His Arg Lys Glu Asn Gln Gly
        195                 200                 205

Ser His Glu Ser Pro Thr Leu Asn Pro Glu Thr Val Ala Ile Asn Leu
    210                 215                 220

Ser Asp Val Asp Leu Ser Lys Tyr Ile Thr Thr Ile Ala Gly Val Met
225                 230                 235                 240

Thr Leu Ser Gln Val Lys Gly Phe Val Arg Lys Asn Gly Val Asn Glu
                245                 250                 255

Ala Lys Ile Asp Glu Ile Lys Asn Asp Asn Val Gln Asp Thr Ala Glu
            260                 265                 270

Gln Lys Val Gln Leu Leu Arg Asn Trp His Gln Leu His Gly Lys Lys
        275                 280                 285

Glu Ala Tyr Asp Thr Leu Ile Lys Asp Leu Lys Lys Ala Asn Leu Cys
    290                 295                 300

Thr Leu Ala Glu Lys Ile Gln Thr Ile Ile Leu Lys Asp Ile Thr Ser
305                 310                 315                 320

Asp Ser Glu Asn Ser Asn Phe Arg Asn Glu Ile Gln Ser Leu Val
```

<210> SEQ ID NO 4
<211> LENGTH: 702
<212> TYPE: PRT
<213> ORGANISM: Homo sapiens

<400> SEQUENCE: 4

```
Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Val His Asn Leu Pro Gln His Leu Phe Gly
50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn
        195                 200                 205

Asp Ser Ala Ser Tyr Lys Cys Glu Thr Gln Asn Pro Val Ser Ala Arg
210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Thr Cys Gln Ala His Asn Ser
290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
            340                 345                 350

Thr Tyr Leu Trp Trp Val Asn Asn Gln Ser Leu Pro Val Ser Pro Arg
        355                 360                 365
```

-continued

```
Leu Gln Leu Ser Asn Asp Asn Arg Thr Leu Thr Leu Leu Ser Val Thr
        370                 375                 380

Arg Asn Asp Val Gly Pro Tyr Glu Cys Gly Ile Gln Asn Glu Leu Ser
385                 390                 395                 400

Val Asp His Ser Asp Pro Val Ile Leu Asn Val Leu Tyr Gly Pro Asp
                405                 410                 415

Asp Pro Thr Ile Ser Pro Ser Tyr Thr Tyr Arg Pro Gly Val Asn
                420                 425                 430

Leu Ser Leu Ser Cys His Ala Ala Ser Asn Pro Pro Ala Gln Tyr Ser
                435                 440                 445

Trp Leu Ile Asp Gly Asn Ile Gln Gln His Thr Gln Glu Leu Phe Ile
450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
                485                 490                 495

Ser Ala Glu Leu Pro Lys Pro Ser Ile Ser Ser Asn Asn Ser Lys Pro
                500                 505                 510

Val Glu Asp Lys Asp Ala Val Ala Phe Thr Cys Glu Pro Glu Ala Gln
                515                 520                 525

Asn Thr Thr Tyr Leu Trp Trp Val Asn Gly Gln Ser Leu Pro Val Ser
                530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                565                 570                 575

Val Ser Ala Asn Arg Ser Asp Pro Val Thr Leu Asp Val Leu Tyr Gly
                580                 585                 590

Pro Asp Thr Pro Ile Ile Ser Pro Pro Asp Ser Ser Tyr Leu Ser Gly
                595                 600                 605

Ala Asn Leu Asn Leu Ser Cys His Ser Ala Ser Asn Pro Ser Pro Gln
                610                 615                 620

Tyr Ser Trp Arg Ile Asn Gly Ile Pro Gln Gln His Thr Gln Val Leu
625                 630                 635                 640

Phe Ile Ala Lys Ile Thr Pro Asn Asn Asn Gly Thr Tyr Ala Cys Phe
                645                 650                 655

Val Ser Asn Leu Ala Thr Gly Arg Asn Asn Ser Ile Val Lys Ser Ile
                660                 665                 670

Thr Val Ser Ala Ser Gly Thr Ser Pro Gly Leu Ser Ala Gly Ala Thr
                675                 680                 685

Val Gly Ile Met Ile Gly Val Leu Val Gly Val Ala Leu Ile
                690                 695                 700

<210> SEQ ID NO 5
<211> LENGTH: 188
<212> TYPE: PRT
<213> ORGANISM: Homo sapiens

<400> SEQUENCE: 5

Met Asp Cys Arg Lys Met Ala Arg Phe Ser Tyr Ser Val Ile Trp Ile
1               5                   10                  15

Met Ala Ile Ser Lys Val Phe Glu Leu Gly Leu Val Ala Gly Leu Gly
                20                  25                  30

His Gln Glu Phe Ala Arg Pro Ser Arg Gly Tyr Leu Ala Phe Arg Asp
            35                  40                  45
```

```
Asp Ser Ile Trp Pro Gln Glu Glu Pro Ala Ile Arg Pro Arg Ser Ser
    50                  55                  60

Gln Arg Val Pro Pro Met Gly Ile Gln His Ser Lys Glu Leu Asn Arg
65                  70                  75                  80

Thr Cys Cys Leu Asn Gly Gly Thr Cys Met Leu Gly Ser Phe Cys Ala
                    85                  90                  95

Cys Pro Pro Ser Phe Tyr Gly Arg Asn Cys Glu His Asp Val Arg Lys
                100                 105                 110

Glu Asn Cys Gly Ser Val Pro His Asp Thr Trp Leu Pro Lys Lys Cys
            115                 120                 125

Ser Leu Cys Lys Cys Trp His Gly Gln Leu Arg Cys Phe Pro Gln Ala
    130                 135                 140

Phe Leu Pro Gly Cys Asp Gly Leu Val Met Asp Glu His Leu Val Ala
145                 150                 155                 160

Ser Arg Thr Pro Glu Leu Pro Pro Ser Ala Arg Thr Thr Thr Phe Met
                165                 170                 175

Leu Val Gly Ile Cys Leu Ser Ile Gln Ser Tyr Tyr
                180                 185

<210> SEQ ID NO 6
<211> LENGTH: 1007
<212> TYPE: PRT
<213> ORGANISM: Homo sapiens

<400> SEQUENCE: 6

Met Gly Ser Gly Gly Asp Ser Leu Leu Gly Gly Arg Gly Ser Leu Pro
1               5                   10                  15

Leu Leu Leu Leu Leu Ile Met Gly Gly Met Ala Gln Asp Ser Pro Pro
                20                  25                  30

Gln Ile Leu Val His Pro Gln Asp Gln Leu Phe Gln Gly Pro Gly Pro
                35                  40                  45

Ala Arg Met Ser Cys Gln Ala Ser Gly Gln Pro Pro Pro Thr Ile Arg
    50                  55                  60

Trp Leu Leu Asn Gly Gln Pro Leu Ser Met Val Pro Pro Asp Pro His
65                  70                  75                  80

His Leu Leu Pro Asp Gly Thr Leu Leu Leu Gln Pro Pro Ala Arg
                85                  90                  95

Gly His Ala His Asp Gly Gln Ala Leu Ser Thr Asp Leu Gly Val Tyr
                100                 105                 110

Thr Cys Glu Ala Ser Asn Arg Leu Gly Thr Ala Val Ser Arg Gly Ala
            115                 120                 125

Arg Leu Ser Val Ala Val Leu Arg Glu Asp Phe Gln Ile Gln Pro Arg
    130                 135                 140

Asp Met Val Ala Val Gly Glu Gln Phe Thr Leu Glu Cys Gly Pro
145                 150                 155                 160

Pro Trp Gly His Pro Glu Pro Thr Val Ser Trp Trp Lys Asp Gly Lys
                165                 170                 175

Pro Leu Ala Leu Gln Pro Gly Arg His Thr Val Ser Gly Gly Ser Leu
                180                 185                 190

Leu Met Ala Arg Ala Glu Lys Ser Asp Glu Gly Thr Tyr Met Cys Val
                195                 200                 205

Ala Thr Asn Ser Ala Gly His Arg Glu Ser Arg Ala Ala Arg Val Ser
            210                 215                 220

Ile Gln Glu Pro Gln Asp Tyr Thr Glu Pro Val Glu Leu Leu Ala Val
```

```
            225                 230                 235                 240

Arg Ile Gln Leu Glu Asn Val Thr Leu Leu Asn Pro Asp Pro Ala Glu
                            245                 250                 255

Gly Pro Lys Pro Arg Pro Ala Val Trp Leu Ser Trp Lys Val Ser Gly
                            260                 265                 270

Pro Ala Pro Ala Gln Ser Tyr Thr Ala Leu Phe Arg Thr Gln Thr
                275                 280                 285

Ala Pro Gly Gly Gln Gly Ala Pro Trp Ala Glu Leu Leu Ala Gly
                290                 295                 300

Trp Gln Ser Ala Glu Leu Gly Gly Leu His Trp Gly Gln Asp Tyr Glu
        305                 310                 315                 320

Phe Lys Val Arg Pro Ser Ser Gly Arg Ala Arg Gly Pro Asp Ser Asn
                            325                 330                 335

Val Leu Leu Leu Arg Leu Pro Glu Lys Val Pro Ser Ala Pro Pro Gln
                        340                 345                 350

Glu Val Thr Leu Lys Pro Gly Asn Gly Thr Val Phe Val Ser Trp Val
                        355                 360                 365

Pro Pro Pro Ala Glu Asn His Asn Gly Ile Ile Arg Gly Tyr Gln Val
                370                 375                 380

Trp Ser Leu Gly Asn Thr Ser Leu Pro Pro Ala Asn Trp Thr Val Val
        385                 390                 395                 400

Gly Glu Gln Thr Gln Leu Glu Ile Ala Thr His Met Pro Gly Ser Tyr
                            405                 410                 415

Cys Val Gln Val Ala Ala Val Thr Gly Ala Gly Ala Gly Glu Pro Ser
                        420                 425                 430

Arg Pro Val Cys Leu Leu Glu Gln Ala Met Glu Arg Ala Thr Gln
                    435                 440                 445

Glu Pro Ser Glu His Gly Pro Trp Thr Leu Glu Gln Leu Arg Ala Thr
                        450                 455                 460

Leu Lys Arg Pro Glu Val Ile Ala Thr Cys Gly Val Ala Leu Trp Leu
        465                 470                 475                 480

Leu Leu Leu Gly Thr Ala Val Cys Ile His Arg Arg Arg Ala Arg
                        485                 490                 495

Val His Leu Gly Pro Gly Leu Tyr Arg Tyr Thr Ser Glu Asp Ala Ile
                        500                 505                 510

Leu Lys His Arg Met Asp His Ser Asp Ser Gln Trp Leu Ala Asp Thr
                    515                 520                 525

Trp Arg Ser Thr Ser Gly Ser Arg Asp Leu Ser Ser Ser Ser Ser Leu
                530                 535                 540

Ser Ser Arg Leu Gly Ala Asp Ala Arg Asp Pro Leu Asp Cys Arg Arg
        545                 550                 555                 560

Ser Leu Leu Ser Trp Asp Ser Arg Ser Pro Gly Val Pro Leu Leu Pro
                            565                 570                 575

Asp Thr Ser Thr Phe Tyr Gly Ser Leu Ile Ala Glu Leu Pro Ser Ser
                        580                 585                 590

Thr Pro Ala Arg Pro Ser Pro Gln Val Pro Ala Val Arg Arg Leu Pro
                    595                 600                 605

Pro Gln Leu Ala Gln Leu Ser Ser Pro Cys Ser Ser Asp Ser Leu
                610                 615                 620

Cys Ser Arg Arg Gly Leu Ser Ser Pro Arg Leu Ser Leu Ala Pro Ala
        625                 630                 635                 640

Glu Ala Trp Lys Ala Lys Lys Lys Gln Glu Leu Gln His Ala Asn Ser
                            645                 650                 655
```

-continued

```
Ser Pro Leu Leu Arg Gly Ser His Ser Leu Glu Leu Arg Ala Cys Glu
            660                 665                 670

Leu Gly Asn Arg Gly Ser Lys Asn Leu Ser Gln Ser Pro Gly Ala Val
        675                 680                 685

Pro Gln Ala Leu Val Ala Trp Arg Ala Leu Gly Pro Lys Leu Leu Ser
    690                 695                 700

Ser Ser Asn Glu Leu Val Thr Arg His Leu Pro Pro Ala Pro Leu Phe
705                 710                 715                 720

Pro His Glu Thr Pro Pro Thr Gln Ser Gln Gln Thr Gln Pro Pro Val
                725                 730                 735

Ala Pro Gln Ala Pro Ser Ser Ile Leu Pro Ala Ala Pro Ile Pro
            740                 745                 750

Ile Leu Ser Pro Cys Ser Pro Pro Ser Pro Gln Ala Ser Ser Leu Ser
        755                 760                 765

Gly Pro Ser Pro Ala Ser Ser Arg Leu Ser Ser Ser Ser Leu Ser Ser
    770                 775                 780

Leu Gly Glu Asp Gln Asp Ser Val Leu Thr Pro Glu Glu Val Ala Leu
785                 790                 795                 800

Cys Leu Glu Leu Ser Glu Gly Glu Glu Thr Pro Arg Asn Ser Val Ser
                805                 810                 815

Pro Met Pro Arg Ala Pro Ser Pro Pro Thr Thr Tyr Gly Tyr Ile Ser
            820                 825                 830

Val Pro Thr Ala Ser Glu Phe Thr Asp Met Gly Arg Thr Gly Gly Gly
        835                 840                 845

Val Gly Pro Lys Gly Gly Val Leu Leu Cys Pro Pro Arg Pro Cys Leu
    850                 855                 860

Thr Pro Thr Pro Ser Glu Gly Ser Leu Ala Asn Gly Trp Gly Ser Ala
865                 870                 875                 880

Ser Glu Asp Asn Ala Ala Ser Ala Arg Ala Ser Leu Val Ser Ser Ser
                885                 890                 895

Asp Gly Ser Phe Leu Ala Asp Ala His Phe Ala Arg Ala Leu Ala Val
            900                 905                 910

Ala Val Asp Ser Phe Gly Phe Gly Leu Glu Pro Arg Glu Ala Asp Cys
        915                 920                 925

Val Phe Ile Asp Ala Ser Ser Pro Ser Pro Arg Asp Glu Ile Phe
    930                 935                 940

Leu Thr Pro Asn Leu Ser Leu Pro Leu Trp Glu Trp Arg Pro Asp Trp
945                 950                 955                 960

Leu Glu Asp Met Glu Val Ser His Thr Gln Arg Leu Gly Arg Gly Met
                965                 970                 975

Pro Pro Trp Pro Pro Asp Ser Gln Ile Ser Ser Gln Arg Ser Gln Leu
            980                 985                 990

His Cys Arg Met Pro Lys Ala Gly  Ala Ser Pro Val Asp  Tyr Ser
        995                 1000                1005

<210> SEQ ID NO 7
<211> LENGTH: 2322
<212> TYPE: PRT
<213> ORGANISM: Homo sapiens

<400> SEQUENCE: 7

Met Gln Ser Gly Pro Arg Pro Pro Leu Pro Ala Pro Gly Leu Ala Leu
1               5                   10                  15

Ala Leu Thr Leu Thr Met Leu Ala Arg Leu Ala Ser Ala Ala Ser Phe
```

```
                20                  25                  30
Phe Gly Glu Asn His Leu Glu Val Pro Val Ala Thr Ala Leu Thr Asp
             35                  40                  45

Ile Asp Leu Gln Leu Gln Phe Ser Thr Ser Gln Pro Glu Ala Leu Leu
 50                  55                  60

Leu Leu Ala Ala Gly Pro Ala Asp His Leu Leu Gln Leu Tyr Ser
 65                  70                  75                  80

Gly Arg Leu Gln Val Arg Leu Val Leu Gly Gln Glu Glu Leu Arg Leu
                     85                  90                  95

Gln Thr Pro Ala Glu Thr Leu Leu Ser Asp Ser Ile Pro His Thr Val
                100                 105                 110

Val Leu Thr Val Val Glu Gly Trp Ala Thr Leu Ser Val Asp Gly Phe
            115                 120                 125

Leu Asn Ala Ser Ser Ala Val Pro Gly Ala Pro Leu Glu Val Pro Tyr
        130                 135                 140

Gly Leu Phe Val Gly Gly Thr Gly Thr Leu Gly Leu Pro Tyr Leu Arg
145                 150                 155                 160

Gly Thr Ser Arg Pro Leu Arg Gly Cys Leu His Ala Ala Thr Leu Asn
                165                 170                 175

Gly Arg Ser Leu Leu Arg Pro Leu Thr Pro Asp Val His Glu Gly Cys
                180                 185                 190

Ala Glu Glu Phe Ser Ala Ser Asp Asp Val Ala Leu Gly Phe Ser Gly
            195                 200                 205

Pro His Ser Leu Ala Ala Phe Pro Ala Trp Gly Thr Gln Asp Glu Gly
        210                 215                 220

Thr Leu Glu Phe Thr Leu Thr Thr Gln Ser Arg Gln Ala Pro Leu Ala
225                 230                 235                 240

Phe Gln Ala Gly Gly Arg Arg Gly Asp Phe Ile Tyr Val Asp Ile Phe
                245                 250                 255

Glu Gly His Leu Arg Ala Val Val Glu Lys Gly Gln Gly Thr Val Leu
                260                 265                 270

Leu His Asn Ser Val Pro Val Ala Asp Gly Gln Pro His Glu Val Ser
            275                 280                 285

Val His Ile Asn Ala His Arg Leu Glu Ile Ser Val Asp Gln Tyr Pro
        290                 295                 300

Thr His Thr Ser Asn Arg Gly Val Leu Ser Tyr Leu Glu Pro Arg Gly
305                 310                 315                 320

Ser Leu Leu Leu Gly Gly Leu Asp Ala Glu Ala Ser Arg His Leu Gln
                325                 330                 335

Glu His Arg Leu Gly Leu Thr Pro Glu Ala Thr Asn Ala Ser Leu Leu
            340                 345                 350

Gly Cys Met Glu Asp Leu Ser Val Asn Gly Gln Arg Arg Gly Leu Arg
        355                 360                 365

Glu Ala Leu Leu Thr Arg Asn Met Ala Ala Gly Cys Arg Leu Glu Glu
        370                 375                 380

Glu Glu Tyr Glu Asp Asp Ala Tyr Gly His Tyr Glu Ala Phe Ser Thr
385                 390                 395                 400

Leu Ala Pro Glu Ala Trp Pro Ala Met Glu Leu Pro Glu Pro Cys Val
                405                 410                 415

Pro Glu Pro Gly Leu Pro Pro Val Phe Ala Asn Phe Thr Gln Leu Leu
            420                 425                 430

Thr Ile Ser Pro Leu Val Val Ala Glu Gly Gly Thr Ala Trp Leu Glu
        435                 440                 445
```

```
Trp Arg His Val Gln Pro Thr Leu Asp Leu Met Glu Ala Glu Leu Arg
        450                 455                 460

Lys Ser Gln Val Leu Phe Ser Val Thr Arg Gly Ala Arg His Gly Glu
465                 470                 475                 480

Leu Glu Leu Asp Ile Pro Gly Ala Gln Ala Arg Lys Met Phe Thr Leu
                        485                 490                 495

Leu Asp Val Val Asn Arg Lys Ala Arg Phe Ile His Asp Gly Ser Glu
                500                 505                 510

Asp Thr Ser Asp Gln Leu Val Leu Glu Val Ser Val Thr Ala Arg Val
            515                 520                 525

Pro Met Pro Ser Cys Leu Arg Arg Gly Gln Thr Tyr Leu Leu Pro Ile
        530                 535                 540

Gln Val Asn Pro Val Asn Asp Pro Pro His Ile Ile Phe Pro His Gly
545                 550                 555                 560

Ser Leu Met Val Ile Leu Glu His Thr Gln Lys Pro Leu Gly Pro Glu
                565                 570                 575

Val Phe Gln Ala Tyr Asp Pro Asp Ser Ala Cys Glu Gly Leu Thr Phe
                580                 585                 590

Gln Val Leu Gly Thr Ser Ser Gly Leu Pro Val Glu Arg Arg Asp Gln
            595                 600                 605

Pro Gly Glu Pro Ala Thr Glu Phe Ser Cys Arg Glu Leu Glu Ala Gly
        610                 615                 620

Ser Leu Val Tyr Val His Arg Gly Gly Pro Ala Gln Asp Leu Thr Phe
625                 630                 635                 640

Arg Val Ser Asp Gly Leu Gln Ala Ser Pro Pro Ala Thr Leu Lys Val
                645                 650                 655

Val Ala Ile Arg Pro Ala Ile Gln Ile His Arg Ser Thr Gly Leu Arg
                660                 665                 670

Leu Ala Gln Gly Ser Ala Met Pro Ile Leu Pro Ala Asn Leu Ser Val
            675                 680                 685

Glu Thr Asn Ala Val Gly Gln Asp Val Ser Val Leu Phe Arg Val Thr
        690                 695                 700

Gly Ala Leu Gln Phe Gly Glu Leu Gln Lys Gln Gly Ala Gly Gly Val
705                 710                 715                 720

Glu Gly Ala Glu Trp Trp Ala Thr Gln Ala Phe His Gln Arg Asp Val
                725                 730                 735

Glu Gln Gly Arg Val Arg Tyr Leu Ser Thr Asp Pro Gln His His Ala
            740                 745                 750

Tyr Asp Thr Val Glu Asn Leu Ala Leu Glu Val Gln Val Gly Gln Glu
        755                 760                 765

Ile Leu Ser Asn Leu Ser Phe Pro Val Thr Ile Gln Arg Ala Thr Val
770                 775                 780

Trp Met Leu Arg Leu Glu Pro Leu His Thr Gln Asn Thr Gln Gln Glu
785                 790                 795                 800

Thr Leu Thr Thr Ala His Leu Glu Ala Thr Leu Glu Glu Ala Gly Pro
                805                 810                 815

Ser Pro Pro Thr Phe His Tyr Glu Val Val Gln Ala Pro Arg Lys Gly
            820                 825                 830

Asn Leu Gln Leu Gln Gly Thr Arg Leu Ser Asp Gly Gln Gly Phe Thr
        835                 840                 845

Gln Asp Asp Ile Gln Ala Gly Arg Val Thr Tyr Gly Ala Thr Ala Arg
    850                 855                 860
```

-continued

```
Ala Ser Glu Ala Val Glu Asp Thr Phe Arg Phe Arg Val Thr Ala Pro
865                 870                 875                 880

Pro Tyr Phe Ser Pro Leu Tyr Thr Phe Pro Ile His Ile Gly Gly Asp
            885                 890                 895

Pro Asp Ala Pro Val Leu Thr Asn Val Leu Val Val Pro Glu Gly
        900                 905                 910

Gly Glu Gly Val Leu Ser Ala Asp His Leu Phe Val Lys Ser Leu Asn
        915                 920                 925

Ser Ala Ser Tyr Leu Tyr Glu Val Met Glu Arg Pro Arg His Gly Arg
        930                 935                 940

Leu Ala Trp Arg Gly Thr Gln Asp Lys Thr Thr Met Val Thr Ser Phe
945                 950                 955                 960

Thr Asn Glu Asp Leu Leu Arg Gly Arg Leu Val Tyr Gln His Asp Asp
            965                 970                 975

Ser Glu Thr Thr Glu Asp Asp Ile Pro Phe Val Ala Thr Arg Gln Gly
            980                 985                 990

Glu Ser Ser Gly Asp Met Ala Trp Glu Glu Val Arg Gly Val Phe Arg
            995                 1000                1005

Val Ala Ile Gln Pro Val Asn Asp His Ala Pro Val Gln Thr Ile
    1010                1015                1020

Ser Arg Ile Phe His Val Ala Arg Gly Gly Arg Leu Leu Thr
    1025                1030                1035

Thr Asp Asp Val Ala Phe Ser Asp Ala Asp Ser Gly Phe Ala Asp
    1040                1045                1050

Ala Gln Leu Val Leu Thr Arg Lys Asp Leu Leu Phe Gly Ser Ile
    1055                1060                1065

Val Ala Val Asp Glu Pro Thr Arg Pro Ile Tyr Arg Phe Thr Gln
    1070                1075                1080

Glu Asp Leu Arg Lys Arg Arg Val Leu Phe Val His Ser Gly Ala
    1085                1090                1095

Asp Arg Gly Trp Ile Gln Leu Gln Val Ser Asp Gly Gln His Gln
    1100                1105                1110

Ala Thr Ala Leu Leu Glu Val Gln Ala Ser Glu Pro Tyr Leu Arg
    1115                1120                1125

Val Ala Asn Gly Ser Ser Leu Val Val Pro Gln Gly Gly Gln Gly
    1130                1135                1140

Thr Ile Asp Thr Ala Val Leu His Leu Asp Thr Asn Leu Asp Ile
    1145                1150                1155

Arg Ser Gly Asp Glu Val His Tyr His Val Thr Ala Gly Pro Arg
    1160                1165                1170

Trp Gly Gln Leu Val Arg Ala Gly Gln Pro Ala Thr Ala Phe Ser
    1175                1180                1185

Gln Gln Asp Leu Leu Asp Gly Ala Val Leu Tyr Ser His Asn Gly
    1190                1195                1200

Ser Leu Ser Pro Arg Asp Thr Met Ala Phe Ser Val Glu Ala Gly
    1205                1210                1215

Pro Val His Thr Asp Ala Thr Leu Gln Val Thr Ile Ala Leu Glu
    1220                1225                1230

Gly Pro Leu Ala Pro Leu Lys Leu Val Arg His Lys Lys Ile Tyr
    1235                1240                1245

Val Phe Gln Gly Glu Ala Ala Glu Ile Arg Arg Asp Gln Leu Glu
    1250                1255                1260

Ala Ala Gln Glu Ala Val Pro Pro Ala Asp Ile Val Phe Ser Val
```

-continued

```
            1265                1270                1275
Lys Ser Pro Pro Ser Ala Gly Tyr Leu Val Met Val Ser Arg Gly
            1280                1285                1290

Ala Leu Ala Asp Glu Pro Pro Ser Leu Asp Pro Val Gln Ser Phe
            1295                1300                1305

Ser Gln Glu Ala Val Asp Thr Gly Arg Val Leu Tyr Leu His Ser
            1310                1315                1320

Arg Pro Glu Ala Trp Ser Asp Ala Phe Ser Leu Asp Val Ala Ser
            1325                1330                1335

Gly Leu Gly Ala Pro Leu Glu Gly Val Leu Val Glu Leu Glu Val
            1340                1345                1350

Leu Pro Ala Ala Ile Pro Leu Glu Ala Gln Asn Phe Ser Val Pro
            1355                1360                1365

Glu Gly Gly Ser Leu Thr Leu Ala Pro Pro Leu Leu Arg Val Ser
            1370                1375                1380

Gly Pro Tyr Phe Pro Thr Leu Leu Gly Leu Ser Leu Gln Val Leu
            1385                1390                1395

Glu Pro Pro Gln His Gly Ala Leu Gln Lys Glu Asp Gly Pro Gln
            1400                1405                1410

Ala Arg Thr Leu Ser Ala Phe Ser Trp Arg Met Val Glu Glu Gln
            1415                1420                1425

Leu Ile Arg Tyr Val His Asp Gly Ser Glu Thr Leu Thr Asp Ser
            1430                1435                1440

Phe Val Leu Met Ala Asn Ala Ser Glu Met Asp Arg Gln Ser His
            1445                1450                1455

Pro Val Ala Phe Thr Val Thr Val Leu Pro Val Asn Asp Gln Pro
            1460                1465                1470

Pro Ile Leu Thr Thr Asn Thr Gly Leu Gln Met Trp Glu Gly Ala
            1475                1480                1485

Thr Ala Pro Ile Pro Ala Glu Ala Leu Arg Ser Thr Asp Gly Asp
            1490                1495                1500

Ser Gly Ser Glu Asp Leu Val Tyr Thr Ile Glu Gln Pro Ser Asn
            1505                1510                1515

Gly Arg Val Val Leu Arg Gly Ala Pro Gly Thr Glu Val Arg Ser
            1520                1525                1530

Phe Thr Gln Ala Gln Leu Asp Gly Gly Leu Val Leu Phe Ser His
            1535                1540                1545

Arg Gly Thr Leu Asp Gly Gly Phe Arg Phe Arg Leu Ser Asp Gly
            1550                1555                1560

Glu His Thr Ser Pro Gly His Phe Phe Arg Val Thr Ala Gln Lys
            1565                1570                1575

Gln Val Leu Leu Ser Leu Lys Gly Ser Gln Thr Leu Thr Val Cys
            1580                1585                1590

Pro Gly Ser Val Gln Pro Leu Ser Ser Gln Thr Leu Arg Ala Ser
            1595                1600                1605

Ser Ser Ala Gly Thr Asp Pro Gln Leu Leu Leu Tyr Arg Val Val
            1610                1615                1620

Arg Gly Pro Gln Leu Gly Arg Leu Phe His Ala Gln Gln Asp Ser
            1625                1630                1635

Thr Gly Glu Ala Leu Val Asn Phe Thr Gln Ala Glu Val Tyr Ala
            1640                1645                1650

Gly Asn Ile Leu Tyr Glu His Glu Met Pro Pro Glu Pro Phe Trp
            1655                1660                1665
```

```
Glu Ala His Asp Thr Leu Glu Leu Gln Leu Ser Ser Pro Pro Ala
    1670            1675            1680

Arg Asp Val Ala Ala Thr Leu Ala Val Ala Val Ser Phe Glu Ala
    1685            1690            1695

Ala Cys Pro Gln His Pro Ser His Leu Trp Lys Asn Lys Gly Leu
    1700            1705            1710

Trp Val Pro Glu Gly Gln Arg Ala Arg Ile Thr Val Ala Ala Leu
    1715            1720            1725

Asp Ala Ser Asn Leu Leu Ala Ser Val Pro Ser Pro Gln Arg Ser
    1730            1735            1740

Glu His Asp Val Leu Phe Gln Val Thr Gln Phe Pro Ser Arg Gly
    1745            1750            1755

Gln Leu Leu Val Ser Glu Glu Pro Leu His Ala Gly Gln Pro His
    1760            1765            1770

Phe Leu Gln Ser Gln Leu Ala Ala Gly Gln Leu Val Tyr Ala His
    1775            1780            1785

Gly Gly Gly Gly Thr Gln Gln Asp Gly Phe His Phe Arg Ala His
    1790            1795            1800

Leu Gln Gly Pro Ala Gly Ala Ser Val Ala Gly Pro Gln Thr Ser
    1805            1810            1815

Glu Ala Phe Ala Ile Thr Val Arg Asp Val Asn Glu Arg Pro Pro
    1820            1825            1830

Gln Pro Gln Ala Ser Val Pro Leu Arg Leu Thr Arg Gly Ser Arg
    1835            1840            1845

Ala Pro Ile Ser Arg Ala Gln Leu Ser Val Val Asp Pro Asp Ser
    1850            1855            1860

Ala Pro Gly Glu Ile Glu Tyr Glu Val Gln Arg Ala Pro His Asn
    1865            1870            1875

Gly Phe Leu Ser Leu Val Gly Gly Leu Gly Pro Val Thr Arg
    1880            1885            1890

Phe Thr Gln Ala Asp Val Asp Ser Gly Arg Leu Ala Phe Val Ala
    1895            1900            1905

Asn Gly Ser Ser Val Ala Gly Ile Phe Gln Leu Ser Met Ser Asp
    1910            1915            1920

Gly Ala Ser Pro Pro Leu Pro Met Ser Leu Ala Val Asp Ile Leu
    1925            1930            1935

Pro Ser Ala Ile Glu Val Gln Leu Arg Ala Pro Leu Glu Val Pro
    1940            1945            1950

Gln Ala Leu Gly Arg Ser Ser Leu Ser Gln Gln Gln Leu Arg Val
    1955            1960            1965

Val Ser Asp Arg Glu Glu Pro Glu Ala Ala Tyr Arg Leu Ile Gln
    1970            1975            1980

Gly Pro Gln Tyr Gly His Leu Leu Val Gly Gly Arg Pro Thr Ser
    1985            1990            1995

Ala Phe Ser Gln Phe Gln Ile Asp Gln Gly Glu Val Val Phe Ala
    2000            2005            2010

Phe Thr Asn Phe Ser Ser Ser His Asp His Phe Arg Val Leu Ala
    2015            2020            2025

Leu Ala Arg Gly Val Asn Ala Ser Ala Val Val Asn Val Thr Val
    2030            2035            2040

Arg Ala Leu Leu His Val Trp Ala Gly Gly Pro Trp Pro Gln Gly
    2045            2050            2055
```

```
Ala Thr Leu Arg Leu Asp Pro Thr Val Leu Asp Ala Gly Glu Leu
    2060                2065                2070

Ala Asn Arg Thr Gly Ser Val Pro Arg Phe Arg Leu Leu Glu Gly
    2075                2080                2085

Pro Arg His Gly Arg Val Val Arg Val Pro Arg Ala Arg Thr Glu
    2090                2095                2100

Pro Gly Gly Ser Gln Leu Val Glu Gln Phe Thr Gln Gln Asp Leu
    2105                2110                2115

Glu Asp Gly Arg Leu Gly Leu Glu Val Gly Arg Pro Glu Gly Arg
    2120                2125                2130

Ala Pro Gly Pro Ala Gly Asp Ser Leu Thr Leu Glu Leu Trp Ala
    2135                2140                2145

Gln Gly Val Pro Pro Ala Val Ala Ser Leu Asp Phe Ala Thr Glu
    2150                2155                2160

Pro Tyr Asn Ala Ala Arg Pro Tyr Ser Val Ala Leu Leu Ser Val
    2165                2170                2175

Pro Glu Ala Ala Arg Thr Glu Ala Gly Lys Pro Glu Ser Ser Thr
    2180                2185                2190

Pro Thr Gly Glu Pro Gly Pro Met Ala Ser Ser Pro Glu Pro Ala
    2195                2200                2205

Val Ala Lys Gly Gly Phe Leu Ser Phe Leu Glu Ala Asn Met Phe
    2210                2215                2220

Ser Val Ile Ile Pro Met Cys Leu Val Leu Leu Leu Ala Leu
    2225                2230                2235

Ile Leu Pro Leu Leu Phe Tyr Leu Arg Lys Arg Asn Lys Thr Gly
    2240                2245                2250

Lys His Asp Val Gln Val Leu Thr Ala Lys Pro Arg Asn Gly Leu
    2255                2260                2265

Ala Gly Asp Thr Glu Thr Phe Arg Lys Val Glu Pro Gly Gln Ala
    2270                2275                2280

Ile Pro Leu Thr Ala Val Pro Gly Gln Gly Pro Pro Pro Gly Gly
    2285                2290                2295

Gln Pro Asp Pro Glu Leu Leu Gln Phe Cys Arg Thr Pro Asn Pro
    2300                2305                2310

Ala Leu Lys Asn Gly Gln Tyr Trp Val
    2315                2320

<210> SEQ ID NO 8
<211> LENGTH: 2201
<212> TYPE: PRT
<213> ORGANISM: Homo sapiens

<400> SEQUENCE: 8

Met Gly Ala Met Thr Gln Leu Leu Ala Gly Val Phe Leu Ala Phe Leu
1               5                   10                  15

Ala Leu Ala Thr Glu Gly Gly Val Leu Lys Lys Val Ile Arg His Lys
                20                  25                  30

Arg Gln Ser Gly Val Asn Ala Thr Leu Pro Glu Glu Asn Gln Pro Val
            35                  40                  45

Val Phe Asn His Val Tyr Asn Ile Lys Leu Pro Val Gly Ser Gln Cys
        50                  55                  60

Ser Val Asp Leu Glu Ser Ala Ser Gly Glu Lys Asp Leu Ala Pro Pro
65                  70                  75                  80

Ser Glu Pro Ser Glu Ser Phe Gln Glu His Thr Val Asp Gly Glu Asn
                85                  90                  95
```

-continued

```
Gln Ile Val Phe Thr His Arg Ile Asn Ile Pro Arg Arg Ala Cys Gly
            100                 105                 110
Cys Ala Ala Ala Pro Asp Val Lys Glu Leu Leu Ser Arg Leu Glu Glu
            115                 120                 125
Leu Glu Asn Leu Val Ser Ser Leu Arg Glu Gln Cys Thr Ala Gly Ala
            130                 135                 140
Gly Cys Cys Leu Gln Pro Ala Thr Gly Arg Leu Asp Thr Arg Pro Phe
145                 150                 155                 160
Cys Ser Gly Arg Gly Asn Phe Ser Thr Glu Gly Cys Gly Cys Val Cys
                165                 170                 175
Glu Pro Gly Trp Lys Gly Pro Asn Cys Ser Glu Pro Glu Cys Pro Gly
            180                 185                 190
Asn Cys His Leu Arg Gly Arg Cys Ile Asp Gly Gln Cys Ile Cys Asp
            195                 200                 205
Asp Gly Phe Thr Gly Glu Asp Cys Ser Gln Leu Ala Cys Pro Ser Asp
            210                 215                 220
Cys Asn Asp Gln Gly Lys Cys Val Asn Gly Val Cys Ile Cys Phe Glu
225                 230                 235                 240
Gly Tyr Ala Gly Ala Asp Cys Ser Arg Glu Ile Cys Pro Val Pro Cys
                245                 250                 255
Ser Glu Glu His Gly Thr Cys Val Asp Gly Leu Cys Val Cys His Asp
            260                 265                 270
Gly Phe Ala Gly Asp Asp Cys Asn Lys Pro Leu Cys Leu Asn Asn Cys
            275                 280                 285
Tyr Asn Arg Gly Arg Cys Val Glu Asn Glu Cys Val Cys Asp Glu Gly
            290                 295                 300
Phe Thr Gly Glu Asp Cys Ser Glu Leu Ile Cys Pro Asn Asp Cys Phe
305                 310                 315                 320
Asp Arg Gly Arg Cys Ile Asn Gly Thr Cys Tyr Cys Glu Glu Gly Phe
                325                 330                 335
Thr Gly Glu Asp Cys Gly Lys Pro Thr Cys Pro His Ala Cys His Thr
            340                 345                 350
Gln Gly Arg Cys Glu Glu Gly Gln Cys Val Cys Asp Glu Gly Phe Ala
            355                 360                 365
Gly Leu Asp Cys Ser Glu Lys Arg Cys Pro Ala Asp Cys His Asn Arg
            370                 375                 380
Gly Arg Cys Val Asp Gly Arg Cys Glu Cys Asp Asp Gly Phe Thr Gly
385                 390                 395                 400
Ala Asp Cys Gly Glu Leu Lys Cys Pro Asn Gly Cys Ser Gly His Gly
                405                 410                 415
Arg Cys Val Asn Gly Gln Cys Val Cys Asp Glu Gly Tyr Thr Gly Glu
            420                 425                 430
Asp Cys Ser Gln Leu Arg Cys Pro Asn Asp Cys His Ser Arg Gly Arg
            435                 440                 445
Cys Val Glu Gly Lys Cys Val Cys Glu Gln Gly Phe Lys Gly Tyr Asp
            450                 455                 460
Cys Ser Asp Met Ser Cys Pro Asn Asp Cys His Gln His Gly Arg Cys
465                 470                 475                 480
Val Asn Gly Met Cys Val Cys Asp Asp Gly Tyr Thr Gly Glu Asp Cys
                485                 490                 495
Arg Asp Arg Gln Cys Pro Arg Asp Cys Ser Asn Arg Gly Leu Cys Val
            500                 505                 510
```

-continued

```
Asp Gly Gln Cys Val Cys Glu Asp Gly Phe Thr Gly Pro Asp Cys Ala
        515                 520                 525
Glu Leu Ser Cys Pro Asn Asp Cys His Gly Gln Gly Arg Cys Val Asn
    530                 535                 540
Gly Gln Cys Val Cys His Glu Gly Phe Met Gly Lys Asp Cys Lys Glu
545                 550                 555                 560
Gln Arg Cys Pro Ser Asp Cys His Gly Gln Gly Arg Cys Val Asp Gly
                565                 570                 575
Gln Cys Ile Cys His Glu Gly Phe Thr Gly Leu Asp Cys Gly Gln His
                580                 585                 590
Ser Cys Pro Ser Asp Cys Asn Asn Leu Gly Gln Cys Val Ser Gly Arg
            595                 600                 605
Cys Ile Cys Asn Glu Gly Tyr Ser Gly Glu Asp Cys Ser Glu Val Ser
610                 615                 620
Pro Pro Lys Asp Leu Val Val Thr Glu Val Thr Glu Glu Thr Val Asn
625                 630                 635                 640
Leu Ala Trp Asp Asn Glu Met Arg Val Thr Glu Tyr Leu Val Val Tyr
                645                 650                 655
Thr Pro Thr His Glu Gly Gly Leu Glu Met Gln Phe Arg Val Pro Gly
                660                 665                 670
Asp Gln Thr Ser Thr Ile Ile Gln Glu Leu Glu Pro Gly Val Glu Tyr
                675                 680                 685
Phe Ile Arg Val Phe Ala Ile Leu Glu Asn Lys Lys Ser Ile Pro Val
            690                 695                 700
Ser Ala Arg Val Ala Thr Tyr Leu Pro Ala Pro Glu Gly Leu Lys Phe
705                 710                 715                 720
Lys Ser Ile Lys Glu Thr Ser Val Glu Val Glu Trp Asp Pro Leu Asp
                725                 730                 735
Ile Ala Phe Glu Thr Trp Glu Ile Ile Phe Arg Asn Met Asn Lys Glu
                740                 745                 750
Asp Glu Gly Glu Ile Thr Lys Ser Leu Arg Arg Pro Glu Thr Ser Tyr
            755                 760                 765
Arg Gln Thr Gly Leu Ala Pro Gly Gln Glu Tyr Glu Ile Ser Leu His
770                 775                 780
Ile Val Lys Asn Asn Thr Arg Gly Pro Gly Leu Lys Arg Val Thr Thr
785                 790                 795                 800
Thr Arg Leu Asp Ala Pro Ser Gln Ile Glu Val Lys Asp Val Thr Asp
                805                 810                 815
Thr Thr Ala Leu Ile Thr Trp Phe Lys Pro Leu Ala Glu Ile Asp Gly
                820                 825                 830
Ile Glu Leu Thr Tyr Gly Ile Lys Asp Val Pro Gly Asp Arg Thr Thr
            835                 840                 845
Ile Asp Leu Thr Glu Asp Glu Asn Gln Tyr Ser Ile Gly Asn Leu Lys
850                 855                 860
Pro Asp Thr Glu Tyr Glu Val Ser Leu Ile Ser Arg Arg Gly Asp Met
865                 870                 875                 880
Ser Ser Asn Pro Ala Lys Glu Thr Phe Thr Thr Gly Leu Asp Ala Pro
                885                 890                 895
Arg Asn Leu Arg Arg Val Ser Gln Thr Asp Asn Ser Ile Thr Leu Glu
                900                 905                 910
Trp Arg Asn Gly Lys Ala Ala Ile Asp Ser Tyr Arg Ile Lys Tyr Ala
            915                 920                 925
Pro Ile Ser Gly Gly Asp His Ala Glu Val Asp Val Pro Lys Ser Gln
```

-continued

```
            930             935             940
Gln Ala Thr Thr Lys Thr Thr Leu Thr Gly Leu Arg Pro Gly Thr Glu
945                 950             955                 960

Tyr Gly Ile Gly Val Ser Ala Val Lys Glu Asp Lys Glu Ser Asn Pro
            965             970             975

Ala Thr Ile Asn Ala Ala Thr Glu Leu Asp Thr Pro Lys Asp Leu Gln
            980             985             990

Val Ser Glu Thr Ala Glu Thr Ser Leu Thr Leu Leu Trp Lys Thr Pro
        995             1000            1005

Leu Ala Lys Phe Asp Arg Tyr Arg Leu Asn Tyr Ser Leu Pro Thr
    1010            1015            1020

Gly Gln Trp Val Gly Val Gln Leu Pro Arg Asn Thr Thr Ser Tyr
    1025            1030            1035

Val Leu Arg Gly Leu Glu Pro Gly Gln Glu Tyr Asn Val Leu Leu
    1040            1045            1050

Thr Ala Glu Lys Gly Arg His Lys Ser Lys Pro Ala Arg Val Lys
    1055            1060            1065

Ala Ser Thr Glu Gln Ala Pro Glu Leu Glu Asn Leu Thr Val Thr
    1070            1075            1080

Glu Val Gly Trp Asp Gly Leu Arg Leu Asn Trp Thr Ala Ala Asp
    1085            1090            1095

Gln Ala Tyr Glu His Phe Ile Ile Gln Val Gln Glu Ala Asn Lys
    1100            1105            1110

Val Glu Ala Ala Arg Asn Leu Thr Val Pro Gly Ser Leu Arg Ala
    1115            1120            1125

Val Asp Ile Pro Gly Leu Lys Ala Ala Thr Pro Tyr Thr Val Ser
    1130            1135            1140

Ile Tyr Gly Val Ile Gln Gly Tyr Arg Thr Pro Val Leu Ser Ala
    1145            1150            1155

Glu Ala Ser Thr Gly Glu Thr Pro Asn Leu Gly Glu Val Val Val
    1160            1165            1170

Ala Glu Val Gly Trp Asp Ala Leu Lys Leu Asn Trp Thr Ala Pro
    1175            1180            1185

Glu Gly Ala Tyr Glu Tyr Phe Phe Ile Gln Val Gln Glu Ala Asp
    1190            1195            1200

Thr Val Glu Ala Ala Gln Asn Leu Thr Val Pro Gly Gly Leu Arg
    1205            1210            1215

Ser Thr Asp Leu Pro Gly Leu Lys Ala Ala Thr His Tyr Thr Ile
    1220            1225            1230

Thr Ile Arg Gly Val Thr Gln Asp Phe Ser Thr Thr Pro Leu Ser
    1235            1240            1245

Val Glu Val Leu Thr Glu Glu Val Pro Asp Met Gly Asn Leu Thr
    1250            1255            1260

Val Thr Glu Val Ser Trp Asp Ala Leu Arg Leu Asn Trp Thr Thr
    1265            1270            1275

Pro Asp Gly Thr Tyr Asp Gln Phe Thr Ile Gln Val Gln Glu Ala
    1280            1285            1290

Asp Gln Val Glu Glu Ala His Asn Leu Thr Val Pro Gly Ser Leu
    1295            1300            1305

Arg Ser Met Glu Ile Pro Gly Leu Arg Ala Gly Thr Pro Tyr Thr
    1310            1315            1320

Val Thr Leu His Gly Glu Val Arg Gly His Ser Thr Arg Pro Leu
    1325            1330            1335
```

-continued

```
Ala Val Glu Val Val Thr Glu Asp Leu Pro Gln Leu Gly Asp Leu
    1340                1345                1350

Ala Val Ser Glu Val Gly Trp Asp Gly Leu Arg Leu Asn Trp Thr
    1355                1360                1365

Ala Ala Asp Asn Ala Tyr Glu His Phe Val Ile Gln Val Gln Glu
    1370                1375                1380

Val Asn Lys Val Glu Ala Ala Gln Asn Leu Thr Leu Pro Gly Ser
    1385                1390                1395

Leu Arg Ala Val Asp Ile Pro Gly Leu Glu Ala Ala Thr Pro Tyr
    1400                1405                1410

Arg Val Ser Ile Tyr Gly Val Ile Arg Gly Tyr Arg Thr Pro Val
    1415                1420                1425

Leu Ser Ala Glu Ala Ser Thr Ala Lys Glu Pro Glu Ile Gly Asn
    1430                1435                1440

Leu Asn Val Ser Asp Ile Thr Pro Glu Ser Phe Asn Leu Ser Trp
    1445                1450                1455

Met Ala Thr Asp Gly Ile Phe Glu Thr Phe Thr Ile Glu Ile Ile
    1460                1465                1470

Asp Ser Asn Arg Leu Leu Glu Thr Val Glu Tyr Asn Ile Ser Gly
    1475                1480                1485

Ala Glu Arg Thr Ala His Ile Ser Gly Leu Pro Pro Ser Thr Asp
    1490                1495                1500

Phe Ile Val Tyr Leu Ser Gly Leu Ala Pro Ser Ile Arg Thr Lys
    1505                1510                1515

Thr Ile Ser Ala Thr Ala Thr Thr Glu Ala Leu Pro Leu Leu Glu
    1520                1525                1530

Asn Leu Thr Ile Ser Asp Ile Asn Pro Tyr Gly Phe Thr Val Ser
    1535                1540                1545

Trp Met Ala Ser Glu Asn Ala Phe Asp Ser Phe Leu Val Thr Val
    1550                1555                1560

Val Asp Ser Gly Lys Leu Leu Asp Pro Gln Glu Phe Thr Leu Ser
    1565                1570                1575

Gly Thr Gln Arg Lys Leu Glu Leu Arg Gly Leu Ile Thr Gly Ile
    1580                1585                1590

Gly Tyr Glu Val Met Val Ser Gly Phe Thr Gln Gly His Gln Thr
    1595                1600                1605

Lys Pro Leu Arg Ala Glu Ile Val Thr Glu Ala Glu Pro Glu Val
    1610                1615                1620

Asp Asn Leu Leu Val Ser Asp Ala Thr Pro Asp Gly Phe Arg Leu
    1625                1630                1635

Ser Trp Thr Ala Asp Glu Gly Val Phe Asp Asn Phe Val Leu Lys
    1640                1645                1650

Ile Arg Asp Thr Lys Lys Gln Ser Glu Pro Leu Glu Ile Thr Leu
    1655                1660                1665

Leu Ala Pro Glu Arg Thr Arg Asp Leu Thr Gly Leu Arg Glu Ala
    1670                1675                1680

Thr Glu Tyr Glu Ile Glu Leu Tyr Gly Ile Ser Lys Gly Arg Arg
    1685                1690                1695

Ser Gln Thr Val Ser Ala Ile Ala Thr Thr Ala Met Gly Ser Pro
    1700                1705                1710

Lys Glu Val Ile Phe Ser Asp Ile Thr Glu Asn Ser Ala Thr Val
    1715                1720                1725
```

```
Ser Trp Arg Ala Pro Thr Ala Gln Val Glu Ser Phe Arg Ile Thr
1730                1735                1740

Tyr Val Pro Ile Thr Gly Gly Thr Pro Ser Met Val Thr Val Asp
1745                1750                1755

Gly Thr Lys Thr Gln Thr Arg Leu Val Lys Leu Ile Pro Gly Val
1760                1765                1770

Glu Tyr Leu Val Ser Ile Ile Ala Met Lys Gly Phe Glu Glu Ser
1775                1780                1785

Glu Pro Val Ser Gly Ser Phe Thr Thr Ala Leu Asp Gly Pro Ser
1790                1795                1800

Gly Leu Val Thr Ala Asn Ile Thr Asp Ser Glu Ala Leu Ala Arg
1805                1810                1815

Trp Gln Pro Ala Ile Ala Thr Val Asp Ser Tyr Val Ile Ser Tyr
1820                1825                1830

Thr Gly Glu Lys Val Pro Glu Ile Thr Arg Thr Val Ser Gly Asn
1835                1840                1845

Thr Val Glu Tyr Ala Leu Thr Asp Leu Glu Pro Ala Thr Glu Tyr
1850                1855                1860

Thr Leu Arg Ile Phe Ala Glu Lys Gly Pro Gln Lys Ser Ser Thr
1865                1870                1875

Ile Thr Ala Lys Phe Thr Thr Asp Leu Asp Ser Pro Arg Asp Leu
1880                1885                1890

Thr Ala Thr Glu Val Gln Ser Glu Thr Ala Leu Leu Thr Trp Arg
1895                1900                1905

Pro Pro Arg Ala Ser Val Thr Gly Tyr Leu Leu Val Tyr Glu Ser
1910                1915                1920

Val Asp Gly Thr Val Lys Glu Val Ile Val Gly Pro Asp Thr Thr
1925                1930                1935

Ser Tyr Ser Leu Ala Asp Leu Ser Pro Ser Thr His Tyr Thr Ala
1940                1945                1950

Lys Ile Gln Ala Leu Asn Gly Pro Leu Arg Ser Asn Met Ile Gln
1955                1960                1965

Thr Ile Phe Thr Thr Ile Gly Leu Leu Tyr Pro Phe Pro Lys Asp
1970                1975                1980

Cys Ser Gln Ala Met Leu Asn Gly Asp Thr Thr Ser Gly Leu Tyr
1985                1990                1995

Thr Ile Tyr Leu Asn Gly Asp Lys Ala Gln Ala Leu Glu Val Phe
2000                2005                2010

Cys Asp Met Thr Ser Asp Gly Gly Gly Trp Ile Val Phe Leu Arg
2015                2020                2025

Arg Lys Asn Gly Arg Glu Asn Phe Tyr Gln Asn Trp Lys Ala Tyr
2030                2035                2040

Ala Ala Gly Phe Gly Asp Arg Arg Glu Glu Phe Trp Leu Gly Leu
2045                2050                2055

Asp Asn Leu Asn Lys Ile Thr Ala Gln Gly Gln Tyr Glu Leu Arg
2060                2065                2070

Val Asp Leu Arg Asp His Gly Glu Thr Ala Phe Ala Val Tyr Asp
2075                2080                2085

Lys Phe Ser Val Gly Asp Ala Lys Thr Arg Tyr Lys Leu Lys Val
2090                2095                2100

Glu Gly Tyr Ser Gly Thr Ala Gly Asp Ser Met Ala Tyr His Asn
2105                2110                2115

Gly Arg Ser Phe Ser Thr Phe Asp Lys Asp Thr Asp Ser Ala Ile
```

```
                           2120                2125                2130
Thr Asn Cys Ala Leu Ser Tyr Lys Gly Ala Phe Trp Tyr Arg Asn
    2135                2140                2145
Cys His Arg Val Asn Leu Met Gly Arg Tyr Gly Asp Asn Asn His
    2150                2155                2160
Ser Gln Gly Val Asn Trp Phe His Trp Lys Gly His Glu His Ser
    2165                2170                2175
Ile Gln Phe Ala Glu Met Lys Leu Arg Pro Ser Asn Phe Arg Asn
    2180                2185                2190
Leu Glu Gly Arg Arg Lys Arg Ala
    2195                2200

<210> SEQ ID NO 9
<211> LENGTH: 760
<212> TYPE: PRT
<213> ORGANISM: Homo sapiens

<400> SEQUENCE: 9

Met Lys Thr Trp Val Lys Ile Val Phe Gly Val Ala Thr Ser Ala Val
1               5                   10                  15
Leu Ala Leu Leu Val Met Cys Ile Val Leu Arg Pro Ser Arg Val His
                20                  25                  30
Asn Ser Glu Glu Asn Thr Met Arg Ala Leu Thr Leu Lys Asp Ile Leu
            35                  40                  45
Asn Gly Thr Phe Ser Tyr Lys Thr Phe Phe Pro Asn Trp Ile Ser Gly
        50                  55                  60
Gln Glu Tyr Leu His Gln Ser Ala Asp Asn Asn Ile Val Leu Tyr Asn
65                  70                  75                  80
Ile Glu Thr Gly Gln Ser Tyr Thr Ile Leu Ser Asn Arg Thr Met Lys
                85                  90                  95
Ser Val Asn Ala Ser Asn Tyr Gly Leu Ser Pro Asp Arg Gln Phe Val
            100                 105                 110
Tyr Leu Glu Ser Asp Tyr Ser Lys Leu Trp Arg Tyr Ser Tyr Thr Ala
        115                 120                 125
Thr Tyr Tyr Ile Tyr Asp Leu Ser Asn Gly Glu Phe Val Arg Gly Asn
    130                 135                 140
Glu Leu Pro Arg Pro Ile Gln Tyr Leu Cys Trp Ser Pro Val Gly Ser
145                 150                 155                 160
Lys Leu Ala Tyr Val Tyr Gln Asn Asn Ile Tyr Leu Lys Gln Arg Pro
                165                 170                 175
Gly Asp Pro Pro Phe Gln Ile Thr Phe Asn Gly Arg Glu Asn Lys Ile
            180                 185                 190
Phe Asn Gly Ile Pro Asp Trp Val Tyr Glu Glu Glu Met Leu Ala Thr
        195                 200                 205
Lys Tyr Ala Leu Trp Trp Ser Pro Asn Gly Lys Phe Leu Ala Tyr Ala
    210                 215                 220
Glu Phe Asn Asp Thr Asp Ile Pro Val Ile Ala Tyr Ser Tyr Tyr Gly
225                 230                 235                 240
Asp Glu Gln Tyr Pro Arg Thr Ile Asn Ile Pro Tyr Pro Lys Ala Gly
                245                 250                 255
Ala Lys Asn Pro Val Val Arg Ile Phe Ile Ile Asp Thr Thr Tyr Pro
            260                 265                 270
Ala Tyr Val Gly Pro Gln Glu Val Pro Val Pro Ala Met Ile Ala Ser
        275                 280                 285
```

-continued

```
Ser Asp Tyr Tyr Phe Ser Trp Leu Thr Trp Val Thr Asp Glu Arg Val
290                 295                 300

Cys Leu Gln Trp Leu Lys Arg Val Gln Asn Val Ser Val Leu Ser Ile
305                 310                 315                 320

Cys Asp Phe Arg Glu Asp Trp Gln Thr Trp Asp Cys Pro Lys Thr Gln
                325                 330                 335

Glu His Ile Glu Glu Ser Arg Thr Gly Trp Ala Gly Phe Phe Val
            340                 345                 350

Ser Thr Pro Val Phe Ser Tyr Asp Ala Ile Ser Tyr Lys Ile Phe
        355                 360                 365

Ser Asp Lys Asp Gly Tyr Lys His Ile His Tyr Ile Lys Asp Thr Val
370                 375                 380

Glu Asn Ala Ile Gln Ile Thr Ser Gly Lys Trp Glu Ala Ile Asn Ile
385                 390                 395                 400

Phe Arg Val Thr Gln Asp Ser Leu Phe Tyr Ser Ser Asn Glu Phe Glu
                405                 410                 415

Glu Tyr Pro Gly Arg Arg Asn Ile Tyr Arg Ile Ser Ile Gly Ser Tyr
            420                 425                 430

Pro Pro Ser Lys Lys Cys Val Thr Cys His Leu Arg Lys Glu Arg Cys
        435                 440                 445

Gln Tyr Tyr Thr Ala Ser Phe Ser Asp Tyr Ala Lys Tyr Tyr Ala Leu
450                 455                 460

Val Cys Tyr Gly Pro Gly Ile Pro Ile Ser Thr Leu His Asp Gly Arg
465                 470                 475                 480

Thr Asp Gln Glu Ile Lys Ile Leu Glu Glu Asn Lys Glu Leu Glu Asn
                485                 490                 495

Ala Leu Lys Asn Ile Gln Leu Pro Lys Glu Ile Lys Lys Leu Glu
            500                 505                 510

Val Asp Glu Ile Thr Leu Trp Tyr Lys Met Ile Leu Pro Pro Gln Phe
        515                 520                 525

Asp Arg Ser Lys Lys Tyr Pro Leu Leu Ile Gln Val Tyr Gly Gly Pro
530                 535                 540

Cys Ser Gln Ser Val Arg Ser Val Phe Ala Val Asn Trp Ile Ser Tyr
545                 550                 555                 560

Leu Ala Ser Lys Glu Gly Met Val Ile Ala Leu Val Asp Gly Arg Gly
                565                 570                 575

Thr Ala Phe Gln Gly Asp Lys Leu Leu Tyr Ala Val Tyr Arg Lys Leu
            580                 585                 590

Gly Val Tyr Glu Val Glu Asp Gln Ile Thr Ala Val Arg Lys Phe Ile
        595                 600                 605

Glu Met Gly Phe Ile Asp Glu Lys Arg Ile Ala Ile Trp Gly Trp Ser
610                 615                 620

Tyr Gly Gly Tyr Val Ser Ser Leu Ala Leu Ala Ser Gly Thr Gly Leu
625                 630                 635                 640

Phe Lys Cys Gly Ile Ala Val Ala Pro Val Ser Ser Trp Glu Tyr Tyr
                645                 650                 655

Ala Ser Val Tyr Thr Glu Arg Phe Met Gly Leu Pro Thr Lys Asp Asp
            660                 665                 670

Asn Leu Glu His Tyr Lys Asn Ser Thr Val Met Ala Arg Ala Glu Tyr
        675                 680                 685

Phe Arg Asn Val Asp Tyr Leu Leu Ile His Gly Thr Ala Asp Asp Asn
690                 695                 700

Val His Phe Gln Asn Ser Ala Gln Ile Ala Lys Ala Leu Val Asn Ala
```

-continued

```
            705                 710                 715                 720
Gln Val Asp Phe Gln Ala Met Trp Tyr Ser Asp Gln Asn His Gly Leu
                    725                 730                 735

Ser Gly Leu Ser Thr Asn His Leu Tyr Thr His Met Thr His Phe Leu
                740                 745                 750

Lys Gln Cys Phe Ser Leu Ser Asp
            755                 760
```

DR5—FAP BISPECIFIC DEATH RECEPTOR AGONISTIC ANTIBODIES

RELATED APPLICATIONS

This application is a 371 US national phase application of PCT/EP2010/064209 claiming priority to EP Application 09171659.7 filed Sep. 29, 2009, the contents of which are incorporated herein by reference.

FIELD OF THE INVENTION

The present invention relates to bispecific antibodies comprising a first antigen binding site specific for a death receptor and a second antigen binding site specific for a second antigen, methods for their production, pharmaceutical compositions containing said antibodies, and uses thereof.

BACKGROUND OF THE INVENTION

Monoclonal antibodies are proving to be powerful therapeutic agents in the treatment of cancer owing to the selective targeting of antigens which are differentially expressed on cancer cells. The therapeutic strategies of most currently developed monoclonal antibodies include the targeting of tumor-associated antigens to modify tumor-cell biology, inhibition of growth factor receptors, inhibition of angiogenesis, apoptosis induction and cytotoxicity via complement fixation or antibody-dependent cellular cytotoxicity. Some antibodies target the growth factor receptors that are crucial for cancer cell survival, such as trastuzumab (Herceptin®) and cetuximab (Erbitux®). Targeting of the TRAIL death receptors on cancer cells with agonistic monoclonal antibodies represents a new generation of monoclonal antibody therapy, as they are able to directly induce apoptosis of targeted cells. The use of an agonistic monoclonal antibody against the death receptors instead of TRAIL may be advantageous: TRAIL targets multiple receptors including both the death receptors and decoy receptors and, therefore, selectivity is a concern. In addition, TRAIL has a much shorter blood half-life compared with monoclonal antibodies, a factor which affects dose and schedule parameters. The very short blood half-life of TRAIL would require large and frequent doses compared with monoclonal antibodies. In addition recombinant TRAIL is very difficult and tedious to produce.

Michaelson J. S. et al. (mAbs, Vol 1, Issue 2, p:128-141; March/April 2009) describe engineered IgG like biscpecific antibodies targeting two TNF family member receptors, namely TRAIL-R2 (TNF related Apoptosis Inducing Ligand Receptor-2) and LTβR (Lymphotoxin-beta Receptor).

Herrmann T. et al. (Cancer Res 2008; 68: (4); p: 1221-1227) describe bispecific monovalent chemically combined Fab molecules directed to CD95/Fas/Apo-1 cell surface receptor and three target antigens on glioblastoma cells: NG2, EGFR and CD40.

SUMMARY OF THE INVENTION

The present invention relates to antibodies combining a death receptor targeting antigen binding site with a second antigen binding site that targets a second antigen. By that the death receptors become cross linked and apoptosis of the target cell is induced. The advantage of these bispecific death receptor agonistic antibodies over conventional death receptor targeting antibodies is the specificity of induction of apoptosis only at the site where the second antigen is expressed.

In a first object, the present invention relates to a bispecific antibody comprising a first antigen binding site specific for a death receptor antigen and a second antigen binding site specific for a second antigen.

In a preferred embodiment of the bispecific antibody, the death receptor is selected from death receptor 4 polypeptide (DR4), death receptor 5 polypeptide (DR5) or FAS polypeptide, preferably human DR4 polypeptide (Seq. Id. No. 1), human DR5 polypeptide (Seq. Id. No. 2) or human FAS polypeptide (Seq. Id. No. 3).

In a further preferred embodiment of the bispecific antibody, the second antigen is associated with an oncological disease or rheumatoid arthritis.

In a further preferred embodiment of the bispecific antibody, the second antigen is selected from, carcinoembryonic antigen (CEA) polypeptide, CRIPTO protein, magic roundabout homolog 4 (ROBO4) polypeptide, melanoma-associated chondroitin sulfate proteoglycan (MCSP) polypeptide, tenascin C polypeptide and fibroblast activation protein (FAP) polypeptide, preferably human CEA polypeptide (Seq. Id. No. 4), human CRIPTO polypeptide (Seq. Id. No. 5), human ROBO4 polypeptide (Seq. Id. No. 6), human MCSP polypeptide (Seq. Id. No. 7), human tenascin C polypeptide (Seq. Id. No. 8) and human FAP polypeptide (Seq. Id. No. 9).

In a further preferred embodiment of the bispecific antibody, the bispecific antibody is a dimeric molecule comprising a first antibody comprising the first antigen binding site and a second antibody comprising the second antigen binding site.

In a preferred embodiment of the dimeric bispecific antibody of the present invention, the first and second antibody comprise an Fc part of an antibody heavy chain, wherein the Fc part of the first antibody comprises a first dimerization module and the Fc part of the second antibody comprises a second dimerization module allowing a heterodimerization of the two antibodies.

In a further preferred embodiment of the dimeric bispecific antibody, the first dimerization module comprises knobs and the second dimerization module comprises holes according to the knobs into holes strategy (see Carter P.; Ridgway J. B. B.; Presta L. G.: Immunotechnology, Volume 2, Number 1, February 1996, pp. 73-73(1)).

In a further preferred embodiment of the dimeric bispecific antibody, the first antibody is an Immunoglobulin (Ig) molecule comprising a light chain and a heavy chain and the second antibody is selected from the group consisting of scFv, scFab, Fab or Fv.

In a further preferred embodiment the bispecific antibody comprises a modified Fc part having a reduced binding affinity for the Fcγ receptors compared to a wildtype Fc part e.g. a LALA modification.

In yet a further preferred embodiment of the dimeric bispecific antibody, the Ig molecule comprises the first antigen binding site specific for the death receptor and the second antibody comprises the second antigen binding site specific for the second antigen.

In a further preferred embodiment of the bispecific antibody, the Ig molecule comprises the second antigen binding site specific for the second antigen and the second antibody comprises the antigen binding site specific for the death receptor.

In a further preferred embodiment of the dimeric bispecific antibody, the second antibody is fused to the N- or C-terminus of the heavy chain of the Ig molecule.

In a further preferred embodiment of the dimeric bispecific antibody, the second antibody is fused to the N- or C-terminus of the light chain of the Ig molecule.

In yet another preferred embodiment of the dimeric bispecific antibody, the Ig molecule is an IgG. In a further preferred embodiment of the dimeric bispecific antibody, the second molecule is fused to the Ig molecule by a peptide linker, preferably a peptide linker having a length of about 10-30 amino acids.

In a further preferred embodiment of the dimeric bispecific antibody, the second antibody comprises additional cysteine residues to form disulfide bonds.

The bispecific antibodies according to the invention are at least bivalent and can be trivalent or multivalent e.g. tetravalent or hexavalent.

In a second object the present invention relates to a pharmaceutical composition comprising a bispecific antibody of the present invention.

In a third object the present invention relates to a bispecific antibody of the present invention for the treatment of cancer or rheumatoid arthritis.

In further objects the present invention relates to a nucleic acid sequence comprising a sequence encoding a heavy chain of a bispecific antibody of the present invention, a nucleic acid sequence comprising a sequence encoding a light chain of a bispecific antibody of the present invention, an expression vector comprising a nucleic acid sequence of the present invention and to a prokaryotic or eukaryotic host cell comprising a vector of the present invention.

DETAILED DESCRIPTION OF THE INVENTION

Figure 1:
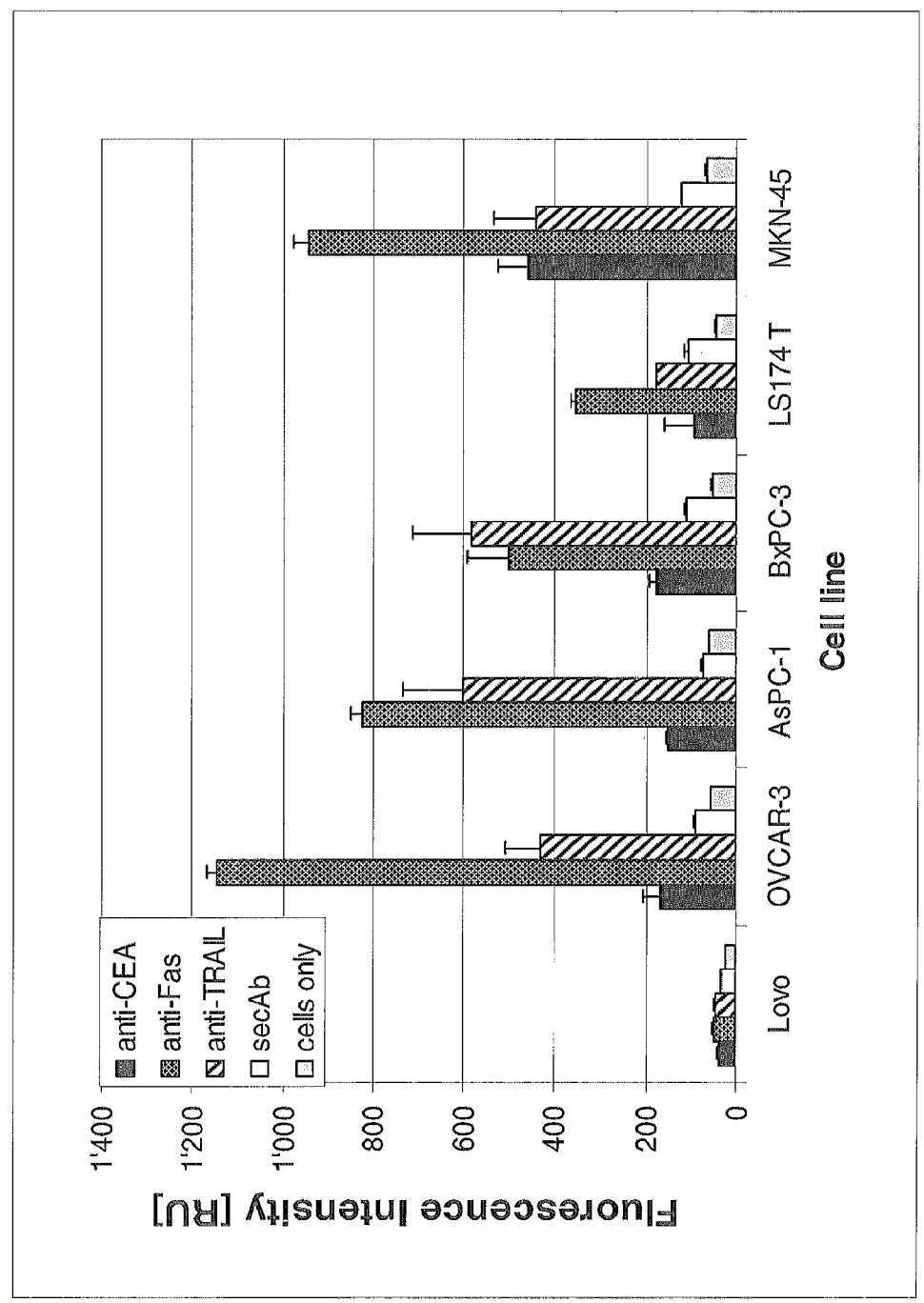
FIG. 1: FACS binding analysis of CEA, DR5 and FAS expression levels on different human cell lines (Lovo, OVCAR-3, AsPC-1, BxPC3, LS174T and MKN-45) using unlabelled, commercially available murine IgG1 antibodies (CEA: Abcam #11330; DR5: R&D #MAB631; FAS: BD #555671) and a common goat anti mouse FITC labelled IgG (Serotec Star105F) for detection. As controls samples containing only cells or cells and secondary antibody alone were used. Except Lovo cells all tested cell lines express significant amounts of DR5 and FAS on the surface. Compared to that CEA expression was rather low. When the same cells were tested with other antibodies for the three antigens also Lovo cells were positive in FACS analysis to express DR5, FAS and CEA (data not shown).

The term "polypeptide" is used herein to refer to native amino acid sequences and sequence variants of the polypeptides of the present invention i.e. DR4, DR5, FAS, CEA, CRIPTO, ROBO4, MCSP, Tenascin C and FAP from any animal, e.g. mammalian species, including humans.

"Native polypeptide" refers to a polypeptide having the same amino acid sequence as a polypeptide occurring in nature regardless of its mode of preparation. The term "native polypeptide" specifically encompasses naturally occurring truncated or secreted forms, naturally occurring variant forms (e.g. alternatively spliced forms), and naturally occurring allelic variants of the polypeptides of the present invention. The amino acid sequences in the Sequence Listing (Seq. Id. No. 1-9) refer to native human sequences of the proteins of the present invention.

The term "polypeptide variant" refers to amino acid sequence variants of a native sequence containing one or more amino acid substitution and/or deletion and/or insertion in the native sequence. The amino acid sequence variants generally have at least about 75%, preferably at least about 80%, more preferably at least about 85%, even more preferably at least about 90%, most preferably at least about 95% sequence identity with the amino acid sequence of a native sequence of a polypeptide of the present invention.

The term "antibody" encompasses the various forms of antibody structures including but not being limited to whole antibodies and antibody fragments. The antibody according to the invention is preferably a fully human antibody, humanized antibody, chimeric antibody, or further genetically engineered antibody as long as the characteristic properties according to the invention are retained.

"Antibody fragments" comprise a portion of a full length antibody, preferably the variable domain thereof, or at least the antigen binding site thereof. Examples of antibody fragments include diabodies, single-chain antibody molecules, and multispecific antibodies formed from antibody fragments. scFv antibodies are, e.g. described in Houston, J. S., Methods in Enzymol. 203 (1991) 46-96). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

The terms "monoclonal antibody" or "monoclonal antibody composition" as used herein refer to a preparation of antibody molecules of a single amino acid composition.

The term "chimeric antibody" refers to an antibody comprising a variable region, i.e., binding region, from one source or species and at least a portion of a constant region derived from a different source or species, usually prepared by recombinant DNA techniques. Chimeric antibodies comprising a murine variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies.". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See e.g. Morrison, S. L., et al., Proc. Natl. Acad. Sci. USA 81 (1984) 6851-6855; U.S. Pat. Nos. 5,202,238 and 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See e.g. Riechmann, L., et al., Nature 332 (1988) 323-327; and Neuberger, M. S., et al., Nature 314 (1985) 268-270. Particularly preferred CDRs correspond to those representing sequences recognizing the antigens noted above for chimeric antibodies. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germline immunoglobulin gene array in such germ-line mutant mice will result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Bruggemann, M., et al., Year Immunol. 7 (1993) 33-40). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole et al. and Boerner et al. are also available for the preparation of human monoclonal antibodies (Cole et al., Monoclonal Antibodies and Cancer Therapy, Alan R. Liss, p. 77 (1985); and Boerner, P., et al., J. Immunol. 147 (1991) 86-95). As already mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation.)

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

The "variable domain" (variable domain of a light chain (VL), variable domain of a heavy chain (VH)) as used herein denotes each of the pair of light and heavy chain domains which are involved directly in binding the antibody to the antigen. The variable light and heavy chain domains have the same general structure and each domain comprises four framework (FR) regions whose sequences are widely conserved, connected by three "hypervariable regions" (or complementary determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody's heavy and light chain CDR3 regions play a particularly important role in the binding specificity/affinity of the antibodies according to the invention and therefore provide a further object of the invention.

The term "antigen-binding site of an antibody" when used herein refer to the amino acid residues of an antibody which are responsible for antigen-binding. The antigen-binding portion of an antibody comprises amino acid residues from the "complementary determining regions" or "CDRs". "Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4. Especially, CDR3 of the heavy chain is the region which contributes most to antigen binding and defines the antibody's properties. CDR and FR regions are determined according to the standard definition of Kabat et al., Sequences of Proteins of Immunological Interest, 5th ed., Public Health Service, National Institutes of Health, Bethesda, Md. (1991) and/or those residues from a "hypervariable loop".

Antibody specificity refers to selective recognition of the antibody for a particular epitope of an antigen. Natural antibodies, for example, are monospecific. "Bispecific antibodies" according to the invention are antibodies which have two different antigen-binding specificities. Antibodies of the present invention are specific for two different antigens, i.e. death receptor antigen as first antigen and a second antigen.

The term "monospecific" antibody as used herein denotes an antibody that has one or more binding sites each of which bind to the same epitope of the same antigen.

The term "bispecific" antibody as used herein denotes an antibody that has at least two binding sites each of which bind to different epitopes of the same antigen or a different antigen.

The term "valent" as used within the current application denotes the presence of a specified number of binding sites in an antibody molecule. As such, the terms "bivalent", "tetravalent", and "hexavalent" denote the presence of two binding sites, four binding sites, and six binding sites, respectively, in an antibody molecule. The bispecific antibodies according to the invention are at least "bivalent" and may be "trivalent" or "multivalent" (e.g."tetravalent" or "hexavalent").

Antibodies of the present invention have two or more binding sites and are bispecific. That is, the antibodies may be bispecific even in cases where there are more than two binding sites (i.e. that the antibody is trivalent or multivalent). Bispecific antibodies of the invention include, for example, multivalent single chain antibodies, diabodies and triabodies, as well as antibodies having the constant domain structure of full length antibodies to which further antigen-binding sites (e.g., single chain Fv, a VH domain and/or a VL domain, Fab, or (Fab)2) are linked via one or more peptide-linkers. The antibodies can be full length from a single species, or be chimerized or humanized.

A "single chain Fab fragment" is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids. Said single chain Fab fragments a) VH-CH1-linker-VL-CL, b) VL-CL-linker-VH-CH1, c) VH-CL-linker-VL-CH1 and d) VL-CH1-linker-VH-CL, are stabilized via the natural disulfide bond between the CL domain and the CH1 domain. In addition, these single chain Fab molecules might be further stabilized by generation of interchain disulfide bonds via insertion of cysteine residues (e.g. position 44 in the variable heavy chain and position 100 in the variable light chain according to Kabat numbering). The term "N-terminus denotes the last amino acid of the N-terminus, The term "C-terminus denotes the last amino acid of the C-terminus.

The terms "nucleic acid" or "nucleic acid molecule", as used herein, are intended to include DNA molecules and RNA molecules. A nucleic acid molecule may be single-stranded or double-stranded, but preferably is double-stranded DNA.

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

A nucleic acid is "operably linked" when it is placed into a functional relationship with another nucleic acid. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are colinear, and, in the case of a secretory leader, contiguous and in reading frame. However, enhancers do not have to be contiguous Linking is accomplished by ligation at convenient restriction sites. If such sites do not exist, synthetic oligonucleotide adaptors or linkers are used in accordance with conventional practice.

As used herein, the expressions "cell", "cell line", and "cell culture" are used interchangeably and all such designations include progeny. Thus, the words "transfectants" and "transfected cells" include the primary subject cell and cultures derived there from without regard for the number of transfers. It is also understood that all progeny may not be precisely identical in DNA content, due to deliberate or inadvertent mutations. Variant progeny that have the same function or biological activity as screened for in the originally transformed cell are included.

As used herein, the term "binding" or "specifically binding" refers to the binding of the antibody to an epitope of the antigen in an in-vitro assay, preferably in a surface plasmon resonance assay (SPR, BIAcore, GE-Healthcare Uppsala, Sweden). The affinity of the binding is defined by the terms ka (rate constant for the association of the antibody from the antibody/antigen complex), kD (dissociation constant), and KD (kD/ka). Binding or specifically binding means a binding affinity (KD) of 10-8 mol/l or less, preferably 10-9 M to 10-13 mol/l.

Binding of the antibody to the death receptor can be investigated by a BIAcore assay (GE-Healthcare Uppsala, Sweden). The affinity of the binding is defined by the terms ka (rate constant for the association of the antibody from the antibody/antigen complex), kD (dissociation constant), and KD (kD/ka)

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

The "Fc part" of an antibody is not involved directly in binding of an antibody to an antigen, but exhibit various effector functions. A "Fc part of an antibody" is a term well known to the skilled artisan and defined on the basis of papain cleavage of antibodies. Depending on the amino acid sequence of the constant region of their heavy chains, antibodies or immunoglobulins are divided in the classes: IgA, IgD, IgE, IgG and IgM, and several of these may be further divided into subclasses (isotypes), e.g. IgG1, IgG2, IgG3, and IgG4, IgA1, and IgA2. According to the heavy chain constant regions the different classes of immunoglobulins are called α, δ, ε, γ, and μ, respectively. The Fc part of an antibody is directly involved in ADCC (antibody-dependent cell-mediated cytotoxicity) and CDC (complement-dependent cytotoxicity) based on complement activation, C1q binding and Fc receptor binding. Complement activation (CDC) is initiated by binding of complement factor C1q to the Fc part of most IgG antibody subclasses. While the influence of an antibody on the complement system is dependent on certain conditions, binding to C1q is caused by defined binding sites in the Fc part. Such binding sites are known in the state of the art and described e.g. by Boakle et al., Nature 282 (1975) 742-743, Lukas et al., J. Immunol. 127 (1981) 2555-2560, Brunhouse and Cebra, Mol. Immunol. 16 (1979) 907-917, Burton et al., Nature 288 (1980) 338-344, Thommesen et al., Mol. Immunol. 37 (2000) 995-1004, Idusogie et al., J. Immunol 164 (2000) 4178-4184, Hezareh et al., J. Virology 75 (2001) 12161-12168, Morgan et al., Immunology 86 (1995) 319-324, EP 0307434. Such binding sites are e.g. L234, L235, D270, N297, E318, K320, K322, P331 and P329 (numbering according to EU index of Kabat, see below). Antibodies of subclass IgG1, IgG2 and IgG3 usually show complement activation and C1q and C3 binding, whereas IgG4 do not activate the complement system and do not bind C1q and C3.

The antibodies according to the invention are produced by recombinant means. Thus, one aspect of the current invention is a nucleic acid encoding the antibody according to the invention and a further aspect is a cell comprising said nucleic acid encoding an antibody according to the invention. Methods for recombinant production are widely known in the state of the art and comprise protein expression in prokaryotic and eukaryotic cells with subsequent isolation of the antibody and usually purification to a pharmaceutically acceptable purity. For the expression of the antibodies as aforementioned in a host cell, nucleic acids encoding the respective modified light and heavy chains are inserted into expression vectors by standard methods. Expression is performed in appropriate prokaryotic or eukaryotic host cells like CHO cells, NS0 cells, SP2/0 cells, HEK293 (including HEK293 EBNA) cells, COS cells, PER.C6 cells, yeast, or *E. coli* cells, and the antibody is recovered from the cells (supernatant or cells after lysis). General methods for recombinant production of antibodies are well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-161; Werner, R. G., Drug Res. 48 (1998) 870-880.

The antibodies according to the invention are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells such as HEK293 cells, CHO cells, or myeloma cells that do not otherwise produce immunoglobulin protein, to obtain the synthesis of recombinant monoclonal antibodies in the host cells.

Amino acid sequence variants (or mutants) of the antibody according to the invention are prepared by introducing appropriate nucleotide changes into the antibody DNA, or by nucleotide synthesis. Such modifications can be performed, however, only in a very limited range, e.g. as described above. For example, the modifications do not alter the above mentioned antibody characteristics such as the IgG isotype and antigen binding, but may improve the yield of the recombinant production, protein stability or facilitate the purification.

The term "host cell" as used in the current application denotes any kind of cellular system which can be engineered to generate the antibodies according to the current invention. In one embodiment HEK293 cells and CHO cells are used as host cells. As used herein, the expressions "cell," "cell line," and "cell culture" are used interchangeably and all such designations include progeny. Thus, the words "transfectants" and "transfected cells" include the primary subject cell and cultures derived there from without regard for the number of transfers. It is also understood that all progeny may not be precisely identical in DNA content, due to deliberate or inadvertent mutations. Variant progeny that have the same function or biological activity as screened for in the originally transformed cell are included.

Expression in NS0 cells is described by, e.g., Barnes, L. M., et al., Cytotechnology 32 (2000) 109-123; Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; and Norderhaug, L., et al., J. Immunol. Methods 204 (1997) 77-87. A preferred transient expression system (HEK 293) is described by Schlaeger, E.-J., and Christensen, K., in Cytotechnology 30 (1999) 71-83 and by Schlaeger, E.-J., in J. Immunol. Methods 194 (1996) 191-199.

The regulatory element sequences that are suitable for prokaryotes, for example, include a promoter, optionally an operator sequence, and a ribosome binding site. Eukaryotic cells are known to utilize promoters, enhancers and polyadenylation signals.

Purification of antibodies is performed in order to eliminate cellular components or other contaminants, e.g. other cellular nucleic acids or proteins, by standard techniques, including alkaline/SDS treatment, CsCl banding, column chromatography, agarose gel electrophoresis, and others well known in the art. See Ausubel, F., et al., ed. Current Protocols in Molecular Biology, Greene Publishing and Wiley Interscience, New York (1987). Different methods are well established and widespread used for protein purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A. Appl. Biochem. Biotech. 75 (1998) 93-102).

As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intra-muscular, subcutaneous, parenteral, spinal or epidermal administration (e.g. by injection or infusion).

A composition of the present invention can be administered by a variety of methods known in the art. As will be appreciated by the skilled artisan, the route and/or mode of administration will vary depending upon the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The term cancer as used herein refers to proliferative diseases, such as lymphomas, lymphocytic leukemias, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, including refractory versions of any of the above cancers, or a combination of one or more of the above cancers.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier preferably is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

The term "transformation" as used herein refers to process of transfer of a vectors/nucleic acid into a host cell. If cells without formidable cell wall barriers are used as host cells, transfection is carried out e.g. by the calcium phosphate precipitation method as described by Graham and Van der Eh, Virology 52 (1978) 546ff. However, other methods for introducing DNA into cells such as by nuclear injection or by protoplast fusion may also be used. If prokaryotic cells or cells which contain substantial cell wall constructions are used, e.g. one method of transformation is calcium treatment using calcium chloride as described by Cohen, F. N, et al, PNAS. 69 (1972) 7110ff.

As used herein, "expression" refers to the process by which a nucleic acid is transcribed into mRNA and/or to the process by which the transcribed mRNA (also referred to as transcript) is subsequently being translated into peptides, polypeptides, or proteins. The transcripts and the encoded polypeptides are collectively referred to as gene product. If the polynucleotide is derived from genomic DNA, expression in a eukaryotic cell may include splicing of the mRNA.

A "vector" is a nucleic acid molecule, in particular self-replicating, which transfers an inserted nucleic acid molecule into and/or between host cells. The term includes vectors that function primarily for insertion of DNA or RNA into a cell (e.g., chromosomal integration), replication of vectors that function primarily for the replication of DNA or RNA, and expression vectors that function for transcription and/or translation of the DNA or RNA. Also included are vectors that provide more than one of the functions as described.

An "expression vector" is a polynucleotide which, when introduced into an appropriate host cell, can be transcribed and translated into a polypeptide. An "expression system" usually refers to a suitable host cell comprised of an expression vector that can function to yield a desired expression product.

The following examples, and sequence listing and figures herein are provided to aid the understanding of the present invention, the true scope of which is set forth in the appended claims. It is understood that modifications can be made in the procedures set forth without departing from the spirit of the invention.

EXAMPLES

Example 1

Design of Bispecific Antibodies Recognizing Human Death Receptor 5 and Human CEA In the following tetravalent bispecific antibodies comprising a full length antibody binding to a first antigen (human death receptor, DR5) combined with two single chain Fv fragments binding to a second antigen (human carcinoembryonic antigen, CEA) fused via a peptide linker either to the C-terminus of the heavy or light chain of the full length antibody are described. The antibody domains and the linker in said single chain Fvs have the following orientation: VH-linker-VL.

As the variable light and heavy chains of the DR5 recognizing antibody sequences of ApomAb antibody described by Adams in US2007/0031414 A1 were used.

For the CEA antigen binding scFvs the sequences of the variable light and heavy chains of PR1A3 (Bodmer et al., 1999; U.S. Pat. No. 5,965,710) and sm3e (Begent et al., 2003; U.S. Pat. No. 7,232,888 B2) were used.

By gene synthesis and recombinant DNA technology the VH and VL of the corresponding CEA antibodies were linked by a glycine-serine (G4S)4 linker to generate single chain Fvs which were fused by a (G4S)n connector (where n=2 or 4) to either the C-terminus of the heavy or light chain of the ApomAb IgG1.

In addition to the 'wild type' scFvs, variants containing cysteine residues at Kabat position 44 in the variable heavy chain and Kabat position 100 in the variable light chain were produced to generate interchain disulfide bridges between VH and VL. This had the aim to stabilize the scFv molecule to minimize potential aggregation tendency.

To prevent non-specific cross-linking of the bispecific molecules, e.g. via Fcγ receptors such as the human FcγRIIIa, two amino acids in the Fc region of the IgG part of the bispecific molecules were changed. By site directed mutagenesis the two leucine residues at position 234 and 235 in the Fc region were exchanged by alanine residues. This so called LALA mutation is described as to abolish Fc-FcR interaction (Hessell et al., Nature 449 (2007), 101 ff).

All these molecules were recombinantly expressed, produced and purified using standard antibody purification techniques including protein A affinity chromatography followed by size exclusion chromatography. The molecules were characterized in terms of expression yield, stability and biological activity.

A summary of the different bispecific death receptor agonistic antibody molecules consisting of ApomAb-CEA combinations is given in table 1. The description of the design of the different molecules can be concluded from the molecule names, where the first part characterizes the death receptor targeting IgG (e.g. ApomAb), the second name describes the source of the CEA targeting scFv (e.g. PR1A3 or sm3e) and the letter and number combination describes the fusion position and disulfide stabilization property of the scFv.

TABLE 1

Description of the different bispecific death receptor agonistic antibodies targeting human DR5 and human CEA with their relevant characteristics.

| Name | IgG | scFv (CEA) | Fusion position | Linker | Connector | Disulfide stabilization |
|---|---|---|---|---|---|---|
| ApomAb-sm3e-A | ApomAb | sm3e | C-terminus heavy chain | $(G_4S)_4$ | $(G_4S)_2$ | no |
| ApomAb-sm3e-A1 | ApomAb | sm3e | C-terminus heavy chain | $(G_4S)_4$ | $(G_4S)_2$ | yes |

TABLE 1-continued

Description of the different bispecific death receptor agonistic antibodies targeting human DR5 and human CEA with their relevant characteristics.

| Name | IgG | scFv (CEA) | Fusion position | Linker | Connector | Disulfide stabilization |
|---|---|---|---|---|---|---|
| ApomAb-sm3e-B | ApomAb | sm3e | C-terminus light chain | $(G_4S)_4$ | $(G_4S)_2$ | no |
| ApomAb-sm3e-B1 | ApomAb | sm3e | C-terminus light chain | $(G_4S)_4$ | $(G_4S)_2$ | yes |
| ApomAb-PR1A3-A | ApomAb | PR1A3 | C-terminus heavy chain | $(G_4S)_4$ | $(G_4S)_2$ | no |
| ApomAb-PR1A3-A1 | ApomAb | PR1A3 | C-terminus heavy chain | $(G_4S)_4$ | $(G_4S)_2$ | yes |
| ApomAb-PR1A3-B | ApomAb | PR1A3 | C-terminus light chain | $(G_4S)_4$ | $(G_4S)_2$ | no |
| ApomAb-PR1A3-B1 | ApomAb | PR1A3 | C-terminus light chain | $(G_4S)_4$ | $(G_4S)_2$ | yes |

Example 2

Expression and Purification of Bispecific Death Receptor Agonistic Antibodies

Separate expression vectors for the light and heavy chains for each bispecific antibody were constructed. These vectors contain a prokaryotic selection marker, regulatory elements for gene expression in mammalian cells and an origin of replication, oriP, from Ebstein-Barr virus for autonomous replication of the plasmids in EBNA containing HEK293 cells. The plasmids were propagated in *E. coli*, amplified, purified and co-transfected into HEK293 EBNA cells using Ca-phosphate mediated precipitation for transient expression. After seven days the cell culture supernatants were harvested and the antibodies were purified by protein A and size exclusion chromatography. The purified molecules were analyzed for homogeneity, stability and integrity by analytical size exclusion chromatography (before and after one freeze-thaw step) and SDS-PAGE analysis (under non-reducing and reducing conditions).

TABLE 2

Summary of the purification yields and monomer content of different death receptor agonistic bispecific antibodies

| Name | Yield [mg/L] | Concentration [mg/ml] | Monomer content [%] | Aggregate increase after freezing |
|---|---|---|---|---|
| ApomAb-sm3e-A | 4.34 | 0.14 | 100.00 | no |
| ApomAb-sm3e-A1 | 4.38 | 1.25 | 100.00 | no |
| ApomAb-sm3e-B | 3.18 | 1.27 | 100.00 | no |
| ApomAb-sm3e-B1 | 2.19 | 1.10 | 100.00 | no |
| ApomAb-PR1A3-A | 5.83 | 0.22 | 98.48 | yes |
| ApomAb-PR1A3-A1 | 5.62 | 0.20 | 100.00 | no |
| ApomAb-PR1A3-B | 5.00 | 0.43 | 98.88 | yes |
| ApomAb-PR1A3-B1 | 11.46 | 1.25 | 100.00 | no |

All molecules could be produced and purified in sufficient amounts and with appropriate quality for further characterization and testing. The yields after purification were in the range of about 5 mg/L with some deviations for some molecules. For example the yield for ApomAb-sm3e-B1 was significantly lower (2.19 mg/L) while of the corresponding construct, ApomAb-PR1A3_B1 even more than 11 mg/L could be purified.

Determination of aggregate formation after freezing/thawing and increasing of the antibody concentration revealed that, depending on the molecule, the stabilization via interchain disulfide bridges can have beneficial effects on the tendency to form aggregates. In general the disulfide stabilization yielded in higher monomer content of the molecules at least at higher concentrations (table 3).

TABLE 3 aggregate formation of bispecific death receptor agonistic antibodies in correlation with protein concentration

| Construct | Concentration [mg/ml] | Monomer content [%] |
|---|---|---|
| ApomAb-PR1A3-A | 0.22 | 98.48 |
| | 1.73 | 90.90 |
| | 3.30 | 81.50 |
| ApomAb-PR1A3-A1 | 0.20 | 100.00 |
| | 1.50 | 100.00 |
| | 3.37 | 100.00 |
| ApomAb-sm3e-A | 0.14 | 100.00 |
| | 1.11 | 95.00 |
| | 2.74 | 94.00 |
| ApomAb-sm3e-A1 | 1.25 | 100.00 |
| | 0.79 | 98.60 |
| | 2.00 | 97.10 |

The tendency to form aggregates is not only dependent on the disulfide stabilization of the scFv but also on the used antigen binding scFv. From table 3 it is obvious that bispecific Apo-mAb molecules containing PR1A3 scFvs undergo significant aggregation upon increase of protein concentration. At concentrations of more than 3 mg/ml only 80% of the material appears as monomer, while after introduction of two additional cysteine residues (VH44/VL100 according to Kabat numbering) these molecules do not form aggregates at the used concentration.

The degree of aggregate formation with bispecific ApomAb molecules containing sm3e scFvs is not as pronounced since here the monomer content still is around 94% without and 97% with disulfide stabilization, respectively.

Example 3

Induction of Apoptosis by Death Receptor Bispecific DR5-CEA Antibody Molecules

The human DR5 death receptor agonistic antibody ApomAb induces apoptosis of DR5 expressing tumor cells, such as the colon cancer cell lines LS 180 or Colo-205. In-vitro, ApomAb on its own mediates significant apoptosis which can be dramatically increased by cross-linking of the ApomAb-bound DR5 with antibodies binding to the human Fc region of ApomAb. This induction of Apoptosis also translates into in-vivo where it could be shown for different tumor models that ApomAb exhibits significant efficacy (Jin et al., 2008; Adams et al., 2008), most probably by cross-linking events via the human Fc-receptors. To evaluate the potential of DR5-CEA bispecific antibodies for tumor site targeted cross-linking of DR5 with subsequent induction of apoptosis the activity of ApomAb-CEA bispecific molecules in terms of apoptosis mediation was analyzed in-vitro.

In order to determine if DR5-CEA bispecific antibody molecules are able to induce tumor antigen binding dependent apoptosis of target cells DNA fragmentation in tumor cells after incubation with death receptor agonistic bispecific antibodies as a measure of apoptosis was analyzed using a cell death detection ELISA assay.

To figure out which cell lines would be suitable to measure antigen binding dependent cross-linking of DR5 which leads to induction of apoptosis several different tumor cell lines were analyzed for surface expression of DR5, FAS and CEA.

All used target cell lines were analyzed for relative expression levels of tumor-related antigens and FAS or DR5 death receptors before apoptosis assays were performed as follows.

Number and viability of cells was determined. For this, adherently growing cells were detached with cell dissociation buffer (Gibco-Invitrogen #13151-014). Cells were harvested by centrifugation (4 min, 400×g), washed with FACS buffer (PBS/0.1% BSA) and the cell number was adjusted to $1.111 \times 10^6$ cells/ml in FACS buffer. 180 µl of this cell suspension was used per well of a 96 well round bottom plate, resulting in $2 \times 10^5$ cell per well. The cells were incubated for 30 min at 4° C. with the first antibody in appropriate dilution. Then the cells were harvested by centrifugation (4 min, 400×g), supernatant was completely removed and cells were washed once with 150 µl of FACS buffer. The cells were resuspended in 150 µl FACS buffer and incubated with the secondary antibody (in case unlabelled first antibody was used) for 30 min at 4° C. in the dark. After two washing steps with FACS buffer cells were resuspended in 200 µl of FACS buffer and analyzed in a HTS FACSCanto II (BD, Software FACS Diva). Alternatively the cells could be fixed with of 200 µl of 2% PFA (paraformaldehyde) in FACS buffer for 20 min at 4° C. and analyzed later. All assays were performed in triplicates.

In FIG. 1 the results of FACS binding analysis of different tumor cell lines with three specific antibodies recognizing CEA, DR5 or FAS are shown. Except the Lovo cells all other tested cell lines express the tested antigens at different levels. CEA expression was highest in MKN-45 cells and more or less similar in OVCAR-3, AsPC-1, BxPC-3 and LS174T. In terms of DR5 expression the AsPC-1 and BxPC.3 cells express most of the receptor compared to the other cell lines followed by OVCAR-3 and MKN-45 whereas LS174T has the lowest DR5 expression level. Regarding FAS expression the cell lines were different but all showing significant FAS expression. When the Lovo cells which were negative in this assay were analyzed later with different antibodies against CEA, DR5 and FAS they also showed significant expression of the tested antigens (data not shown).

For determination of induced apoptosis the Cell Death Detection ELISA PLUS kit from Roche was used. In short, $10^4$ cells per well of a 96-well plate (after detaching, and determination of cell number and viability) were seeded in 200 µl appropriate medium and were incubated over night at 37° C. in a 5% CO2 atmosphere. The next day the medium was replaced by fresh medium containing the apoptosis inducing antibodies, control antibodies and other controls in appropriate concentrations:

The bispecific antibodies were used in a final concentration of 0.01-10 µg/ml; control antibodies were used at 0.5 µg/ml and cross-linking antibodies were used at 100 µg/ml. Competing antibodies were used at a 100 fold excess.

The cells were incubated for 4-24 hrs at 37° C., 5% $CO_2$ to allow induction of apoptosis. The cells were harvested by centrifugation (10 min, 200×g) and incubated for 1 h at room temperature in 200 µl of lysis buffer (supplied by the kit). Intact cells were sedimented by centrifugation (10 min, 200×g) and 20 µl of the supernatant was analyzed according to the manufacturer's recommendations for induction of apoptosis.

Figure 2:
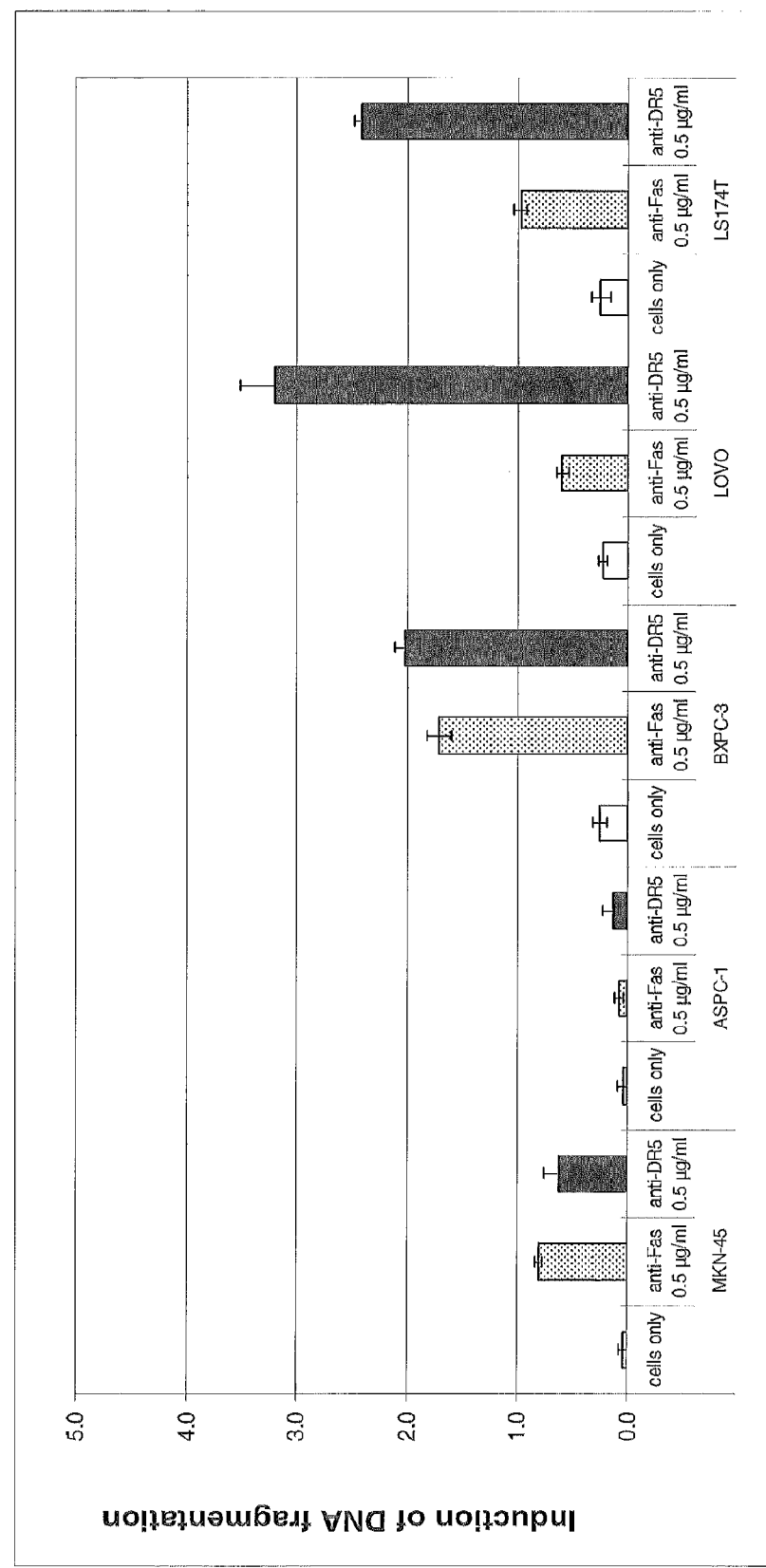
FIG. 2: Analysis of apoptosis induction (DNA fragmentation assay) of different cell lines after 4 hrs incubation with commercially available antibodies that are able to induce apoptosis in solution without cross-linking (DR5: R&D #MAB631; FAS: Millipore/Upstate: CH11). For detection of apoptosis the Cell Death Detection ELISAPLUS kit for analysis of histone-associated DNA fragmentation was used. In BxPC-3, Lovo and LS174T cells apoptosis clearly can be induced via DR5 and FAS, while ASPC-1 cells do not undergo apoptosis at all. MKN-45 cells are more resistant to DR5 compared to the other cell lines.

A set of cell lines also was analyzed for the ability to undergo apoptosis by incubation with commercially available antibodies against DR5 or FAS which are known to cross-link the death receptors already in solution (FIG. 2).

Here significant differences among the cell lines were observed in terms of induction of apoptosis as shown in FIG. 2. While in MKN-45 and BxPC-3 apoptosis induction via DR5 and FAS was similar (although in MKN-45 the DNA fragmentation value reached only 50% of that with BxPC-3), in LS174T and Lovo cells apoptosis could be induced much better with the DR5 cross-linking antibody than with the FAS binding antibody. In LS174T cells apoptosis induction via DR5 cross-linking was about two-fold as effective as apoptosis via FAS cross-linking. In Lovo cells this difference in apoptosis induction was even four-fold. ASPC-1 cells are very resistant to apoptosis induction via death receptor cross-linking Based on these results the two cell lines Lovo and LS174T were chosen to analyze apoptosis induction by tumor antigen targeted cross-linking of DR5.

Figure 3:
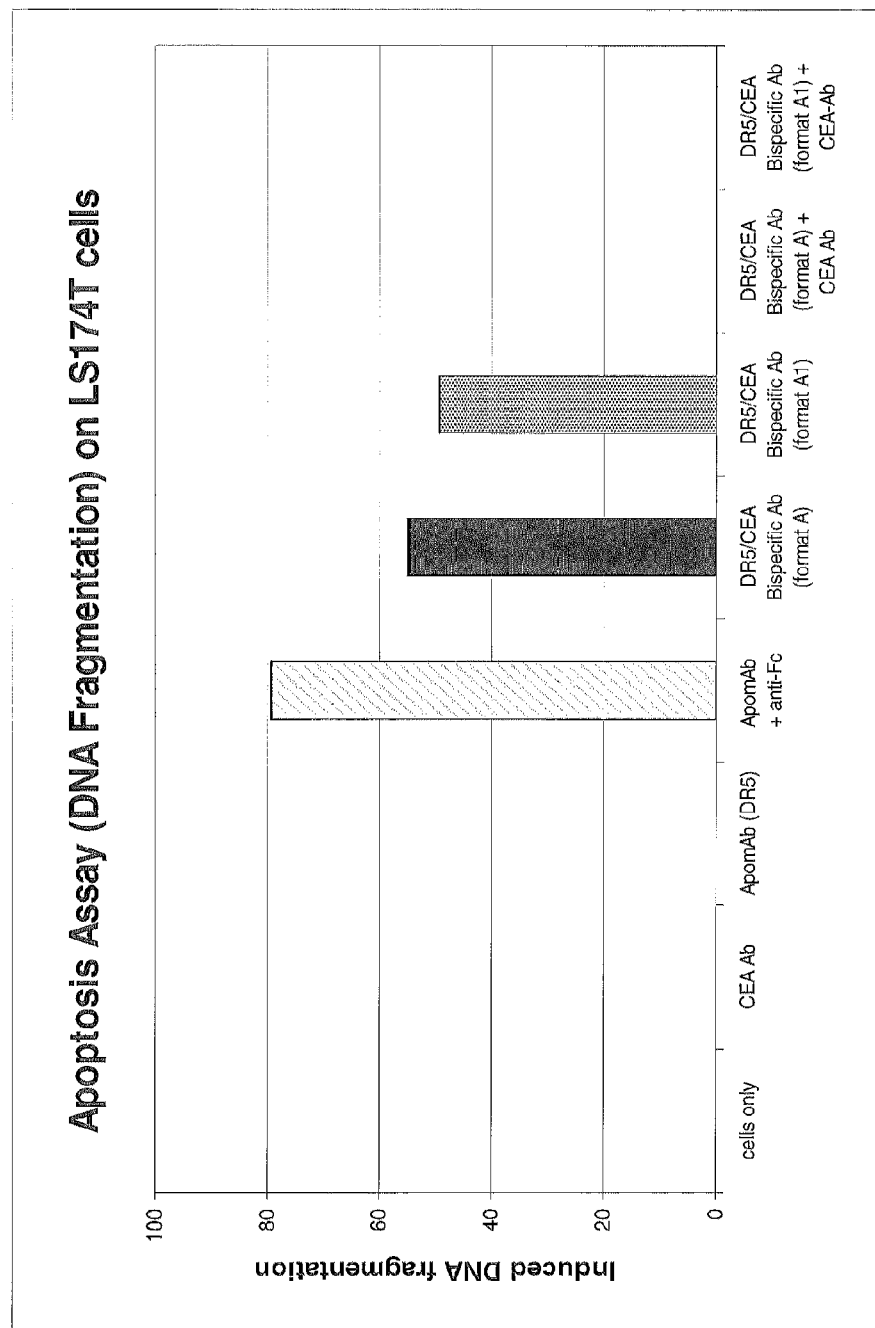
FIG. 3: Induction of apoptosis (DNA fragmentation assay) of LS174T cells after 4 hrs incubation with ApomAb (white bar), ApomAb cross-linked with an anti human Fc antibody (hatched, grey bar), ApomAb_sm3e_A (black bar) and ApomAb_sm3e_A1 (stippled grey bar) bispecific molecules. CEA binding dependent induction of apoptosis by targeted hyper-cross-linking via the bispecific antibodies can be detected. This effect is in the same range as the apoptosis induced by cross-linking of ApomAb and could be completely abolished by pre-incubation with an excess amount of sm3e IgG. No apoptosis was observed with the controls (cells only or sm3e IgG) and also the ApomAb alone did not induce apoptosis in the used concentration (1 μg/ml).

The results of apoptosis induction in LS174T cells upon treatment with bispecific DR5-CEA molecules (ApomAb-sm3e) in comparison with the effect of ApomAb or cross-linked ApomAb is illustrated in FIG. 3. Under the used assay conditions (4 hrs incubation at a concentration of 1 µg/ml) ApomAb alone or sm3e in IgG1 format did not exhibit detectable DNA fragmentation (normalized to the 'cells only' value), while the bispecific ApomAb-sm3e molecules (either wild type (format A) or disulfide stabilized (format A1) scFv) showed significant induction of apoptosis which was comparable to the theoretical maximum of hyper-cross-linked ApomAb. The two bispecific molecules showed very similar activity, demonstrating that the stabilization of the molecule by insertion of interchain disulfides does not affect biological activity. When the cells were pre-incubated with an excess of sm3e IgG (100-fold higher concentration compared to the bispecific constructs) no apoptosis can be induced anymore, indicating that the sm3e IgG blocks all CEA antigen on the cell surface and prevents additional binding of the bispecific death receptor agonistic molecule. This demonstrates that the induced apoptosis is specifically dependent on cross-linking of the DR5 death receptor via the tumor antigen.

Figure 4:
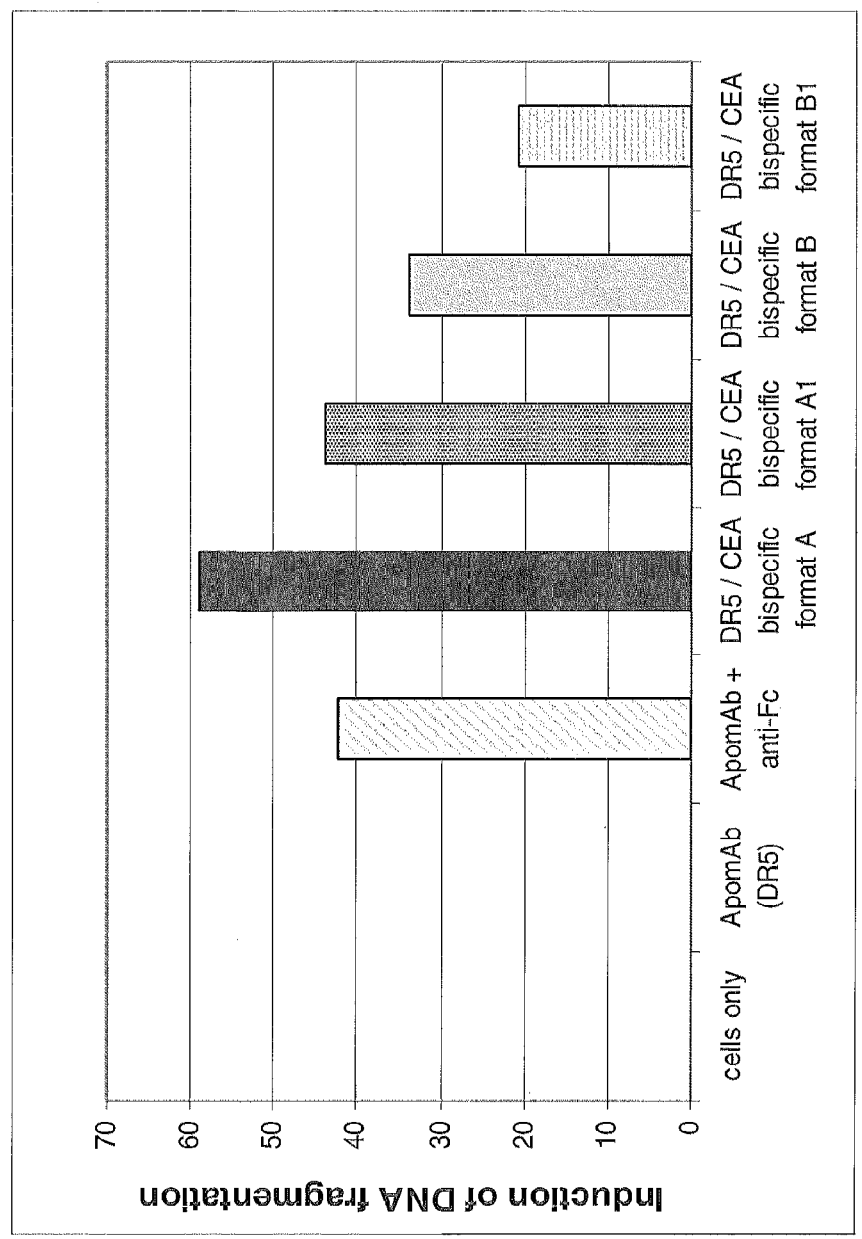
FIG. 4: Comparison of apoptosis inducing activity of different ApomAb_sm3e bispecific molecules compared to ApomAb (white bar) alone or ApomAb cross-linked with an anti human Fc antibody (hatched, grey bar), in a DNA fragmentation assay with LS174T cells incubated for 4 hrs with apoptosis inducing agents. In general, molecules where the sm3e scFv is fused to the C-terminus of the heavy chain of ApomAb (format A, black bar) seem to be more active than constructs in which the sm3e scFv is fused to the C-terminus of the light chain of ApomAb (format B, grey bar). Furthermore, disulfide stabilized scFv containing bispecific antibodies (format A1, dotted grey bar and B1, small grid bar) seem to be slightly inferior to molecules with the wild type scFv.

In FIG. 4 the results of a comparison between different molecule formats of the bispecific ApomAb-sm3e constructs on apoptosis induction of LS174T cells are summarized. Induction of apoptosis was performed for 4 hrs at a concentration of 1 µg/ml. Again, the bispecific Apo-mAb-sm3e molecules in which the sm3e scFv is fused to the C-terminus of the heavy chain of ApomAb (A and A1 format) demonstrated significant induction of apoptosis which was, in this case, even superior to the hyper-cross-linked ApomAb. ApomAb alone did not induce detectable DNA fragmentation under the used conditions. Two additional bispecific constructs (sm3e scFv fused to the C-terminus of the light chain of ApomAb, either wild type=B format or disulfide stabilized=B1 format) also exhibited high levels of apoptosis induction which was, at least for the B format, in a similar range as with cross-linked ApomAb, indicating that both formats basically are functional. The fusion of the scFv to the C-terminus of the heavy chain of ApomAb seem to be slightly advantageous over fusion to the light chain. In comparison to the results shown in FIG. 4, it also might be that the disulfide-stabilized molecules exhibit a slightly reduced activity compared to molecules with wild type scFv.

The ApomAb-sm3e constructs described above worked very well in terms of antigen dependent specific induction of apoptosis as shown in FIGS. 3 and 4. This CEA antibody, sm3e, exhibits a very high affinity towards its antigen (low picomolar range). In order to evaluate if the effect of apoptosis induction with bispecific DR5-CEA constructs also can be mediated with molecules with lower binding affinity to the tumor antigen additional constructs, analogous to the former ones, were generated. The CEA targeting scFv was engineered using the sequence of the CEA antibody PR1A3 which has a rather low affinity to CEA which is in the micromolar range. For evaluation of this antibody bispecific constructs were generated in which the PR1A3 scFv (wild type or disulfide stabilized) was fused to either the C-terminus of the heavy or light chain of ApomAb IgG. The nomenclature of the resulting molecules is analogous to the already described: ApomAb_PR1A3_A/A1/B/B1 where A and A1 describe fusion to the C-terminus of the heavy chain and B and B1 show fusion to the C-terminus of the light chain. A and B contain wild type scFv whereas A1 and B1 indicate disulfide stabilized scFv.

Figure 5:
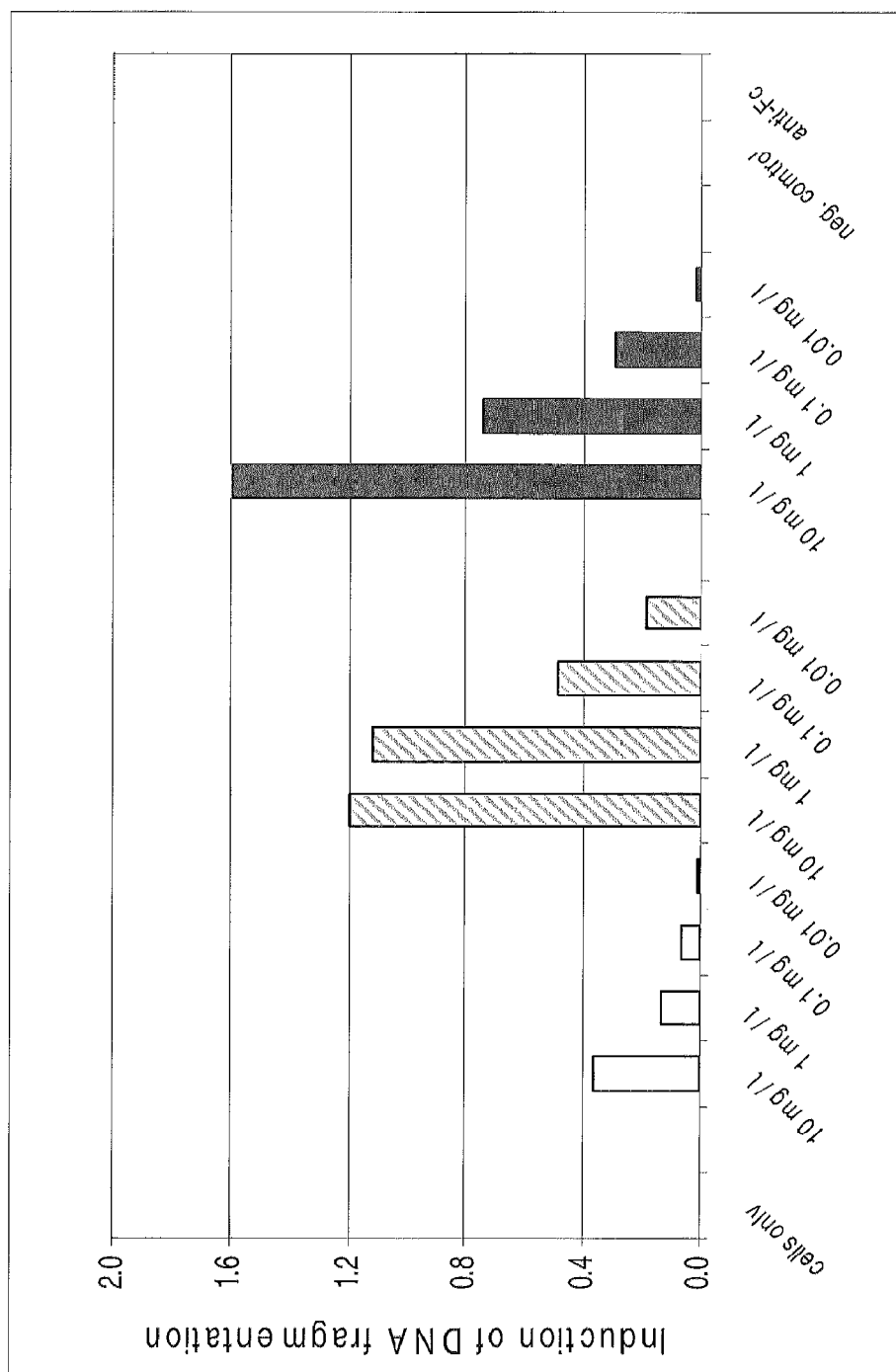
FIG. 5: Analysis of apoptosis induction (DNA fragmentation assay) of LS174T cells after 4 hrs of incubation with either Apomab (white bars), ApomAb that was cross-linked with an anti human Fc antibody (hatched, grey bars) or ApomAb_PR1A3_A bispecific construct (black bars). In each case apoptosis induction was dependent on the concentration of the antibody used. ApomAb alone also induced low levels of apoptosis at high concentrations but this was significantly increased by cross-linking. The bispecific ApomAb_PR1A3_A molecule was even more active without secondary cross-linking agent than the cross-linked ApomAb was.

In FIG. 5 the induction of apoptosis on LS174T cells by ApomAb, cross-linked ApomAb and ApomAb_PR1A3 bispecific antibody (wild type PR1A3 scFv fused to C-terminus of the ApomAb heavy chain) is shown over a concentration range from 0.01 to 10.0 µg/ml. ApomAb on its own exhibits a certain degree of concentration dependent apoptosis induction which could be significantly increased by cross-linking of ApomAb with an anti human Fc antibody. The bispecific ApomAb-PR1A3 molecule also demonstrated concentration dependent induction of apoptosis, which at a concentration of 10.0 µg/ml, was even higher as with the cross-linked ApomAb at concentration at the same concentration indicating that it is not absolutely necessary to use the highest affine tumor antigen binders in this bispecific death receptor agonistic antibody format to achieve good in-vitro efficacy in terms of apoptosis induction.

Figure 6:
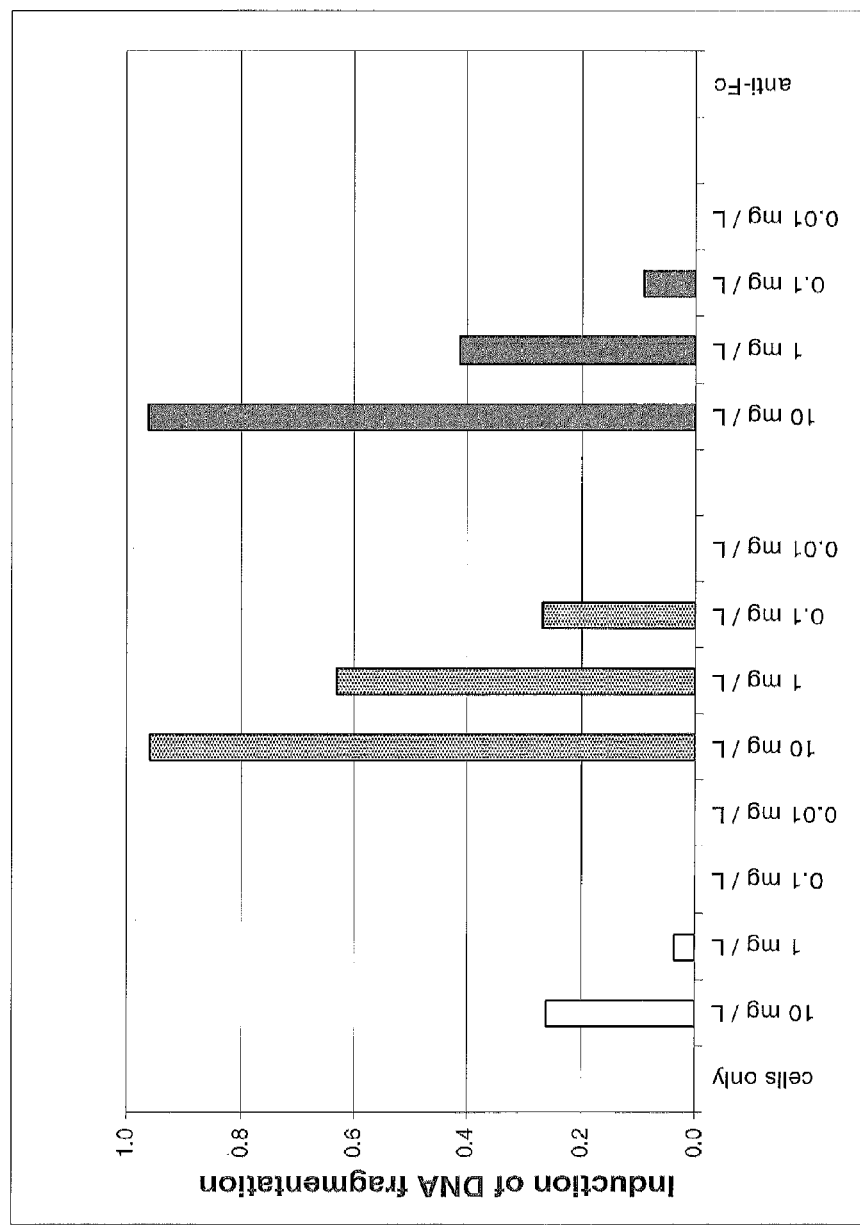
FIG. 6: Analysis of apoptosis induction (DNA fragmentation assay) of Lovo cells after 4 hrs of incubation with either Apomab (white bars), ApomAb that was cross-linked with an anti human Fc antibody (grey bars) or ApomAb_PR1A3_A bispecific construct (black bars). In each case apoptosis induction was dependent on the concentration of the antibody used. ApomAb alone also induced low levels of apoptosis at high concentrations (as described) but this was significantly increased by cross-linking. The bispecific ApomAb_PR1A3_A molecule was as active on its own as the cross-linked ApomAb was.

To investigate, if the observed effect of induction of apoptosis upon incubation with DR5-CEA bispecific molecules can be applied to other cell lines, a similar experiment as shown in FIG. 6 was performed using Lovo cells, another colon cancer cell line.

The results of apoptosis induction in Lovo cells using the death receptor agonistic bispecific molecule ApomAb_R1A3_A (DR5-CEA) compared to induction of apoptosis via ApomAb and cross-linked ApomAb are shown in FIG. 6. For all constructs a concentration dependent induction of apoptosis was observed. Here the ApomAb alone reached about 20% of the activity of cross-linked ApomAb when used in concentration of 10 µg/ml. Below this concentration apoptosis induction was much lower compared to cross-linked ApomAb. The ApomAb_PR1A3 bispecific antibody, in the absence of any cross-linking molecule, showed the same induction of DNA fragmentation as the hyper-cross-linked ApomAb antibody demonstrating that the apoptosis inducing effect using death receptor agonistic antibodies is a general phenomenon that can be applied to all apoptosis competent cell lines.

Figure 7:
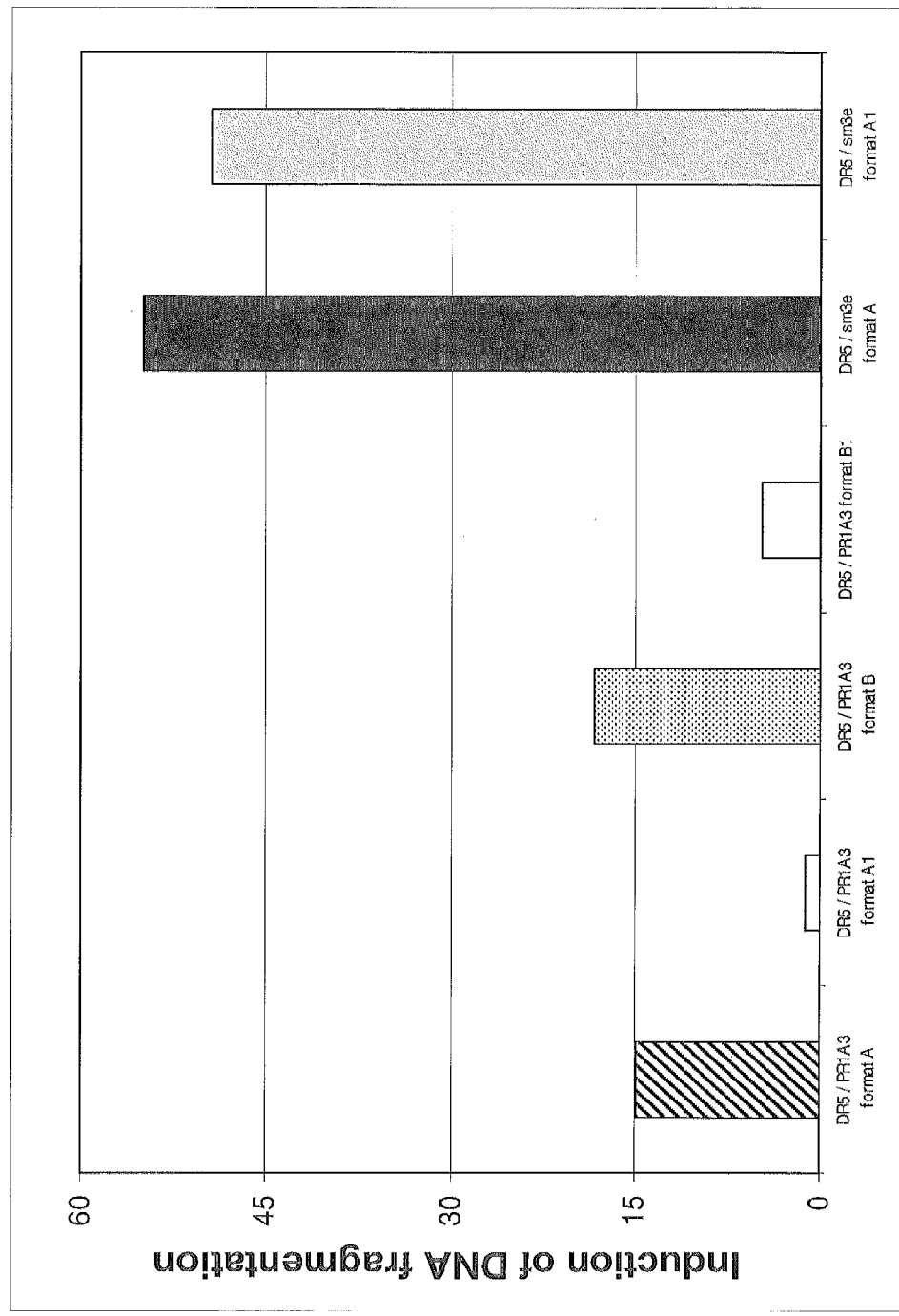
FIG. 7: Comparison of DNA fragmentation in LS174T cells after 4 hrs incubation with different apoptosis inducing bispecific antibodies. The used molecules are ApomAb_PR1A3 bispecific molecules in which the PR1A3 scFv (wt=A/B or disulfide stabilized=A1/B1) is fused to either the C-terminus of the heavy chain (A, hatched grey bar) or the light chain (B, dotted bar). While the fusion position of the scFv in this case does not seem to make a difference in terms of apoptosis induction, the kind of used scFv is important: using the disulfide stabilized scFv almost completely abolished induction of apoptosis compared to constructs containing the wt scFv fused to ApomAb (black and grey bar, respectively). Due to the lower affinity of PR1A3 compared to sm3e also the overall induction of apoptosis is lower with PR1A3 containing bispecific molecules.
Figure 8:
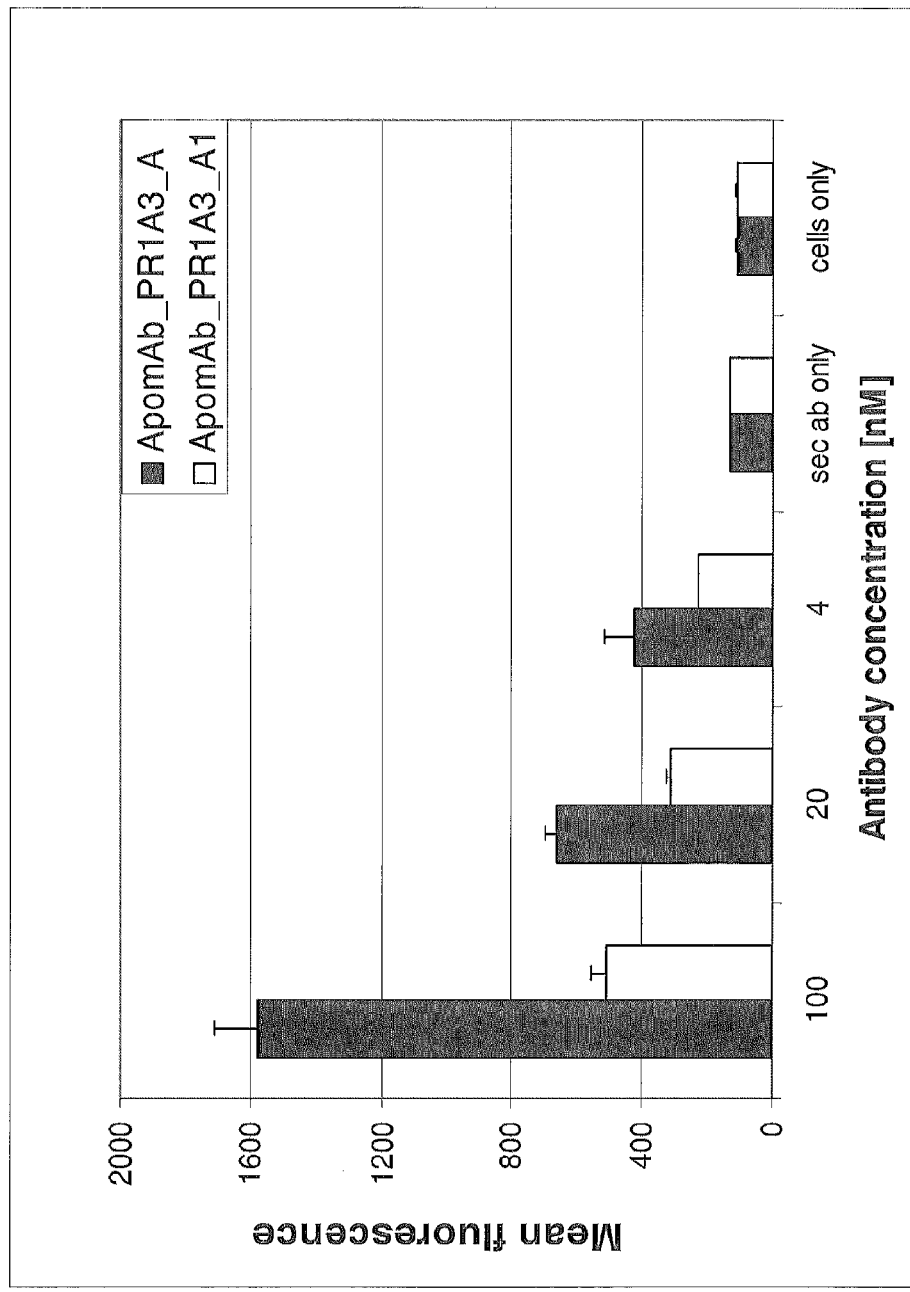
FIG. 8: FACS binding analysis of ApomAb-CEA (PR1A3) bispecific constructs on MKN-45 cells. Comparison of ApomAb_PR1A3 bispecific constructs with wild type (A) or disulfide stabilized scFv (A1). Both bispecific constructs bind in a concentration dependent manner to the target cells but the molecule containing PR1A3 in wild type scFv format binds with much higher affinity to the antigen than the disulfide stabilized PR1A3 scFv.

In FIG. 7 the results of a comparison between different ApomAb-PR1A3 and Apo-mAb-sm3e constructs are shown. Here the induction of apoptosis in LS174T cells after 4 hrs incubation with a concentration of 1 µg/ml are summarized. From the results it becomes quite obvious that the affinity to the CEA antigen indeed might play a role in mediating apoptosis via death receptor cross-linking There is a clear difference in apoptosis induction with constructs containing the high affinity CEA binder compared to the low affinity binder. ApomAb-PR1A3 shows only about one third of the apoptosis induction in LS174T cells compared to ApomAb-sm3e. Furthermore there seem to exist intrinsic differences in the different molecules which also are reflected in the capability of induction of apoptosis. In the cases in which the PR1A3 scFv is fused to ApomAb there is no difference in activity between molecules where the scFv is fused to either the C-terminus of the heavy or light chain. Both molecules show the same induction of apoptosis. In contrast to this, constructs containing the sm3e scFv behave different. Here the fusion of the scFv to the C-terminus of the heavy chain is superior to the fusion to the C-terminus of the light chain.

An additional difference between the two series of constructs is the fact that there is a different effect of disulfide stabilization of scFv. While disulfide stabilized sm3e scFv containing constructs are not affected regarding induction of apoptosis this is contrary for PR1A3 scFvs. These do not exhibit significant induction of apoptosis anymore if used in the disulfide stabilized form.

Example 4

Generation of Bispecific Death Receptor Agonistic Antibodies Targeting FAS (CD95) and CRIPTO as the Tumor Antigen and Evaluation of these Molecules in-vitro CRIPTO is a GPI-anchored growth factor that is reported to be over-expressed in cancer cells, but low or absent in normal cells. CRIPTO is found to be up-regulated in colon tumors and liver metastasis. As a member of the EGF family, it is considered to be an autocrine growth factor that plays a role in proliferation, metastasis, and/or survival of tumor cells. This growth factor activates a number of signaling pathways through several potential receptors or co-receptors.

To figure out if CRIPTO would be a suitable target for the death receptor agonistic bispecific antibody approach tetravalent, bispecific antibodies targeting FAS as the death receptor and CRIPTO as the tumor antigen were generated. These molecules consist of a full length IgG1 antibody (recognizing FAS) to which CRIPTO targeting scFvs are fused to the C-terminus of the heavy chain.

For the heavy and light chains of the FAS targeting IgG part of the molecule the sequences of the HFE7A antibody was used (Haruyama et al., 2002), which is a human/mouse cross-reactive antibody against CD95. The CRIPTO scFv was generated from sequences of a humanized anti-CRIPTO antibody that was generated by immunization (LC020_H3L2D1). The scFv was generated using standard recombinant DNA techniques and fused by a short peptide linker to the C-terminus of the FAS IgG1 heavy chain. The order of the single domains in the scFv is VH-(G4S)4 linker VL.

Figure 9:
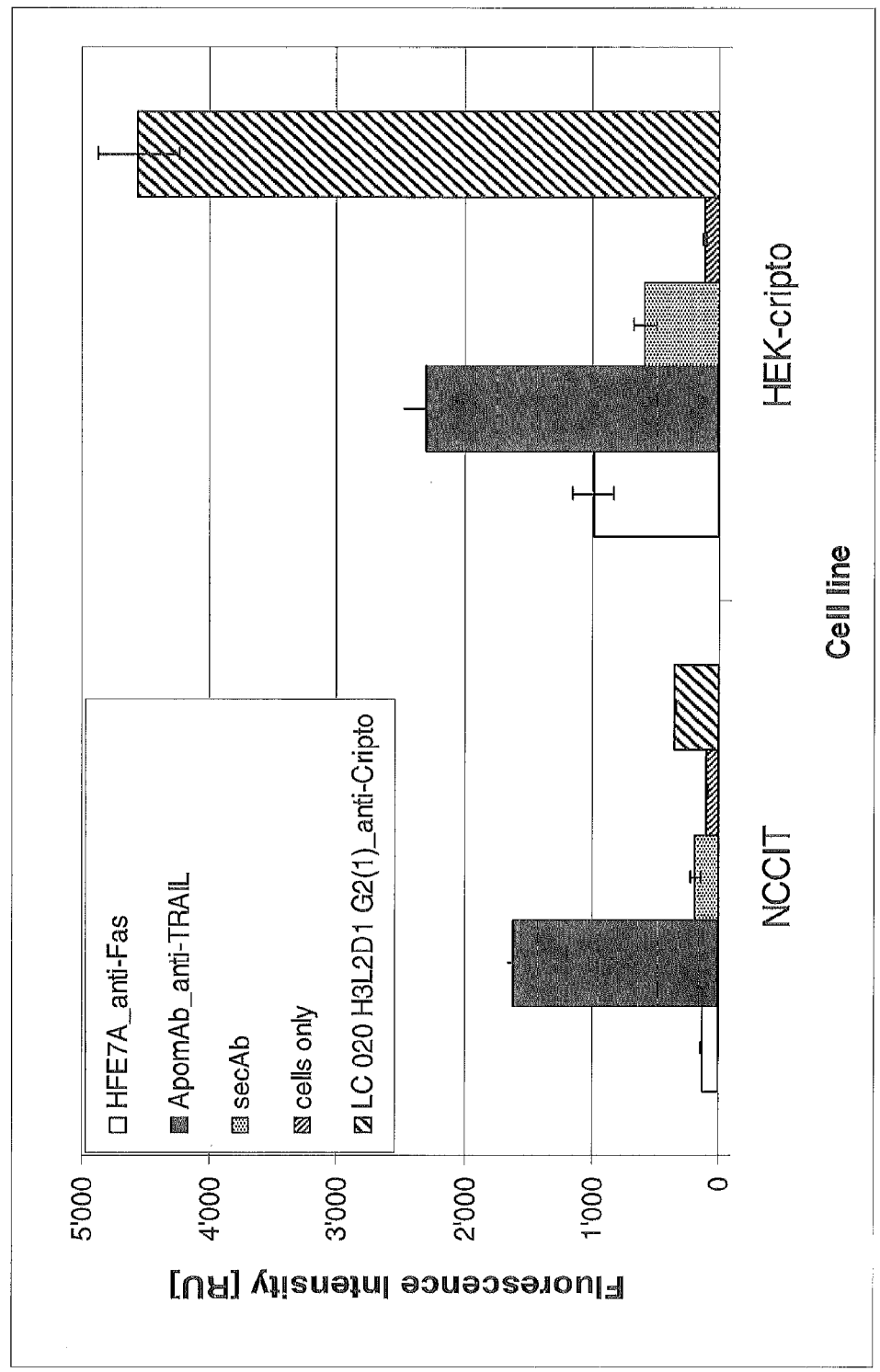
FIG. 9: Analysis of surface expression of CRIPTO, FAS and DR5 on NCCIT and recombinant, CRIPTO expressing HEK293 cells by FACS binding experiments. NCCIT cells do not express FAS, only low amounts of CRIPTO but similar amounts of DR5 compared to recombinant HEK293-CRIPTO cells. The latter cells show low levels of FAS, significant levels of DR5 and rather high levels of CRIPTO expression.

Unfortunately there are not that many suitable cell lines available that can be used for CRIPTO targeting. Therefore two cell lines were evaluated for their potential to be used as target cell line for FAS cross-linking mediated apoptosis induction via bispecific FAS/CRIPTO antibodies. In FIG. 9 the results of the evaluation of surface expression of FAS, DR5 and CRIPTO in NCCIT and recombinant, human CRIPTO expressing HEK cells (hereafter referred to as HEK-CRIPTO) are shown. In contrast to the HEK-CRIPTO cells NCCIT hardly express FAS on the surface and only very low levels of CRIPTO, while DR5 expression seems to be normal. In contrast to that HEK-CRIPTO cells express high levels of CRIPTO, significant levels of DR5 and suitable levels of FAS, why these cells were chosen for in-vitro analysis of apoptosis induction with FAS-CRIPTO bispecific antibodies.

Figure 10:
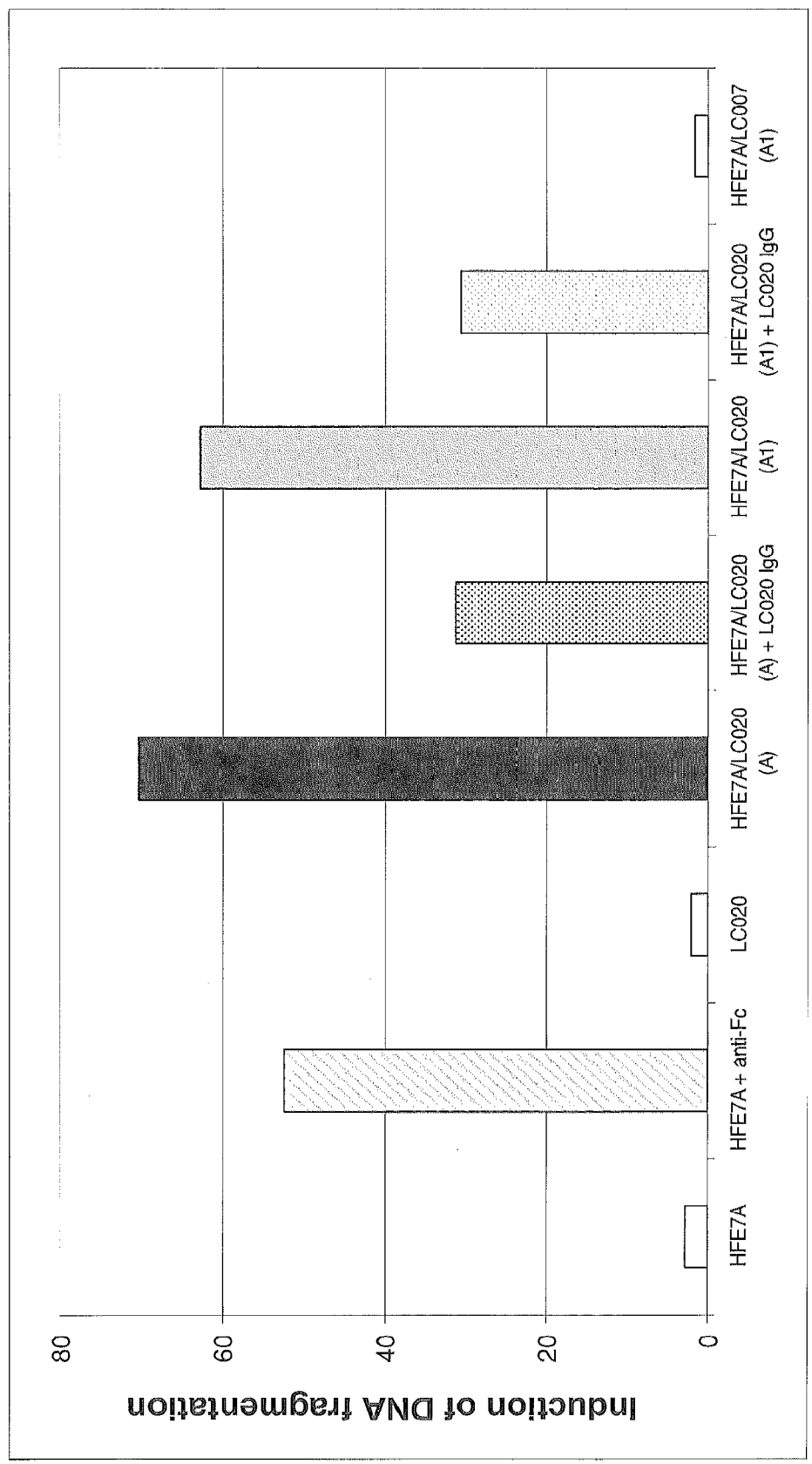
FIG. 10: Apoptosis induction comparison (DNA fragmentation in HEK293-CRIPTO cells) using FAS (HFE7A IgG), FAS (HFE7A IgG) cross-linked via anti human Fc antibody and FAS-CRIPTO bispecific molecules (HFE7A_LC020 H3L2D1, in which the wt (A) or disulfide stabilized (A1) CRIPTO scFv is fused to the C-terminus of the heavy chain of HFE7A. FAS IgG alone, CRIPTO IgG alone and a FAS-MCSP bispecific molecule did not induce apoptosis while the cross-linked FAS and the HFE7A-CRIPTO bispecific molecules show DNA fragmentation after 4 hrs incubation which also in part could be abolished by pre-incubation with excess of anti CRIPTO IgG.

FIG. 10 summarizes the results of in-vitro experiments for induction of apoptosis on HEK-CRIPTO cells using either HFE7A, cross-linked HFE7A or the HFE7A-CRIPTO bispecific constructs. There is no significant apoptosis induction with HFE7A or CRIPTO (LC020) alone. Cross-linking of HFE7A with an anti human Fc antibody leads to high levels of DNA fragmentation as do the bispecific HFE7A-CRIPTO molecules. In this case bispecific molecules that contain either the wild type CRIPTO scFv (HFE7A_LC020_A) or the disulfide stabilized scFv (HFE7A_LC020_A1) fused to the C-terminus of the HFE7A heavy chain. Almost no difference in apoptosis induction between these to molecules could be observed.

In both cases, pre-incubation with excess of CRIPTO IgG significantly reduced apoptosis induction but this reduction was not complete. The reason for that is not clear and needs to be evaluated. An analogous construct in which an MCSP targeting scFv is fused to the C-terminus of the heavy chain of HFE7A (HFE7A_LC007_A1) did not induce any apoptosis of the HEK-CRIPTO cells indicating that the observed apoptosis with the bispecific HFE7A-CRIPTO molecules is tumor antigen specific.

Figure 11:
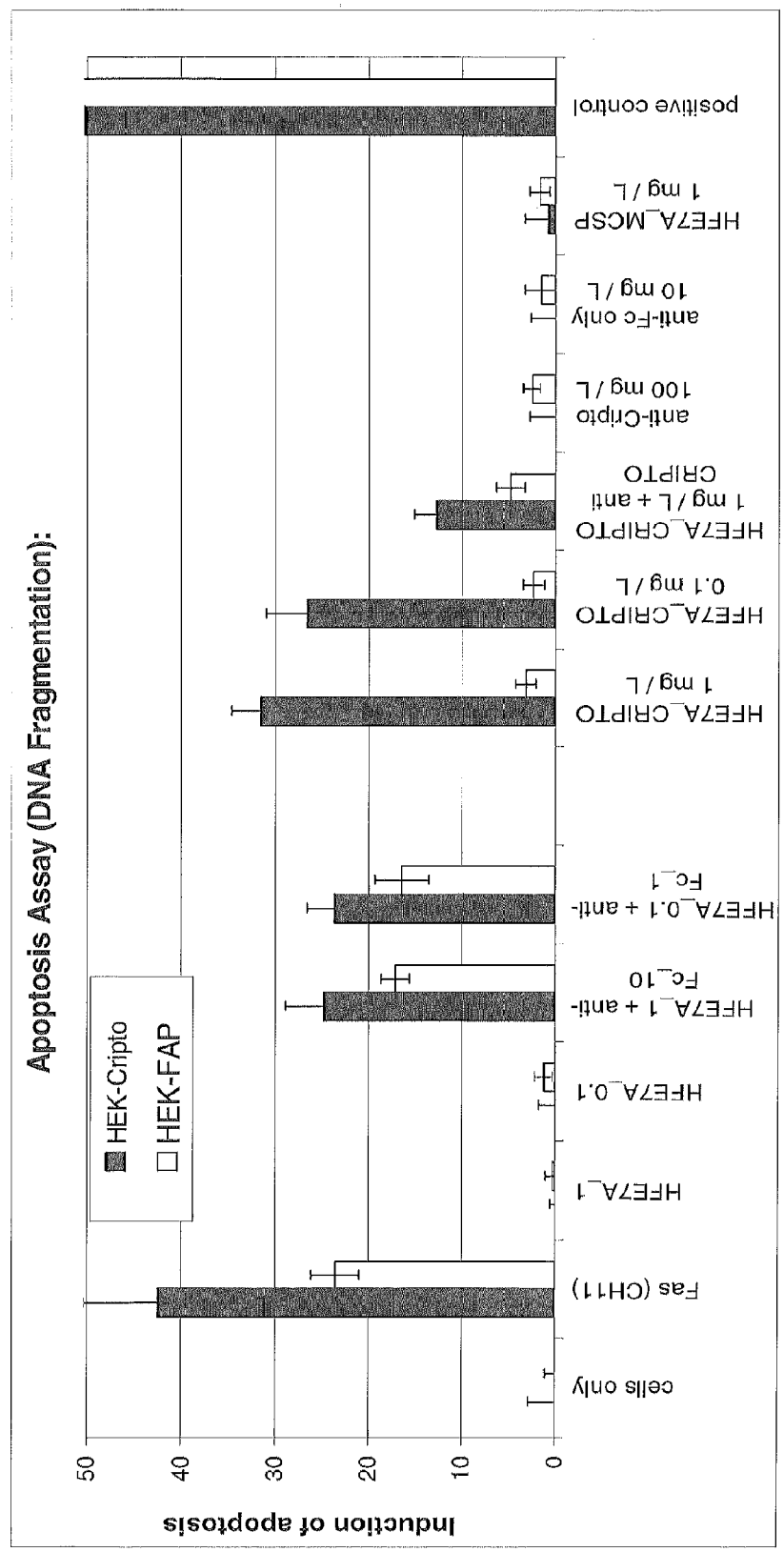
FIG. 11: Apoptosis induction (DNA fragmentation assay) by HFE7A-CRIPTO bispecific molecules in recombinant HEK293-CRIPTO cells (black bars) compared to recombinant HEK293-FAP (fibroblast activation protein) cells (white bars). In both cell lines apoptosis can be induced using an apoptosis inducing commercially available antibody (CH11) and with HFE7A IgG that was cross-linked via a second, Fc specific antibody, whereas HFE7A alone did not induce apoptosis under the used conditions. Induction of apoptosis with the bispecific FAS-CRIPTO molecule was higher than with the cross-linked HFE7A IgG but could not completely be inhibited by pre-incubation with an anti CRIPTO IgG in excess. In the HEK293-FAP cells a certain low background apoptosis could be observed which also could not be out-competed by CRIPTO IgG in excess. Even a negative control molecule (in which a disulfide stabilized MCSP specific scFv was fused to the C-terminus of the heavy chain of HFE7A) showed a low degree of apoptosis in HEK293-FAP cells.

The results from a comparison of apoptosis induction between HEK-CRIPTO and recombinant human FAP (fibroblast activating protein) expressing HEK cells (HEK-FAP) upon treatment with HFE7A-CRIPTO bispecific antibodies are shown in FIG. 11. Both cell lines undergo apoptosis if incubated with a positive control antibody conferring apoptosis already in solution or when treated with cross-linked HFE7A. The anti FAS antibody HFE7A on its own did not mediate apoptosis in these cell lines. The bispecific HFE7A-CRIPTO molecule induced apoptosis only in HEK-CRIPTO cells but not in the control HEK-FAP cells. There seems to be a low level of DNA fragmentation also in the HEK-FAP cells but this is non-specific basal activity since it can be observed also with a unrelated HFE7A-MCSP control molecule and even with the anti CRIPTO and anti Fc antibody alone. As observed in the experiments described in FIG. 10 also in this case the inhibition of apoptosis by pre-incubation with an excess of CRIPTO IgG was not complete.

Example 5

Generation of FAS-MCSP Bispecific Death Receptor Agonistic Antibodies and Evaluation of their Apoptosis Induction Potential Among antigens that are directly expressed and displayed on the tumor cell surface also other antigens are being considered for targeted cross-linking of death receptors to induce apoptosis. In particular these are antigens from the stroma or neovasculature. One example for the latter one is the melanoma associated chondroitin sulfate proteoglycan (MCSP). MCSP is expressed on the majority of melanoma cells but also on glioma cells and on neovasculature. Several monoclonal antibodies targeting human MCSP have been described but none of them was suitable to be used in cancer therapy due to missing efficacy (e.g. lack of ADCC). Therefore MCSP antibodies might gain value if used in a bispecific format that is able to mediate tumor site targeted apoptosis.

In order to evaluate simultaneous tumor/neovasculature targeting with respect to apoptosis induction bispecific death receptor agonistic antibodies were generated in which a MCSP specific scFv (wild type or disulfide stabilized) is fused to the C-terminus of the anti FAS antibody HFE7A. These scFvs are fused via a short peptide linker to HFE7A. The sequences of the variable light and heavy chains to generate the MCSP targeting scFv were taken from the MCSP antibody 9.2.27 (Beavers et al., 1996; U.S. Pat. No. 5,580,774).

Figure 12:
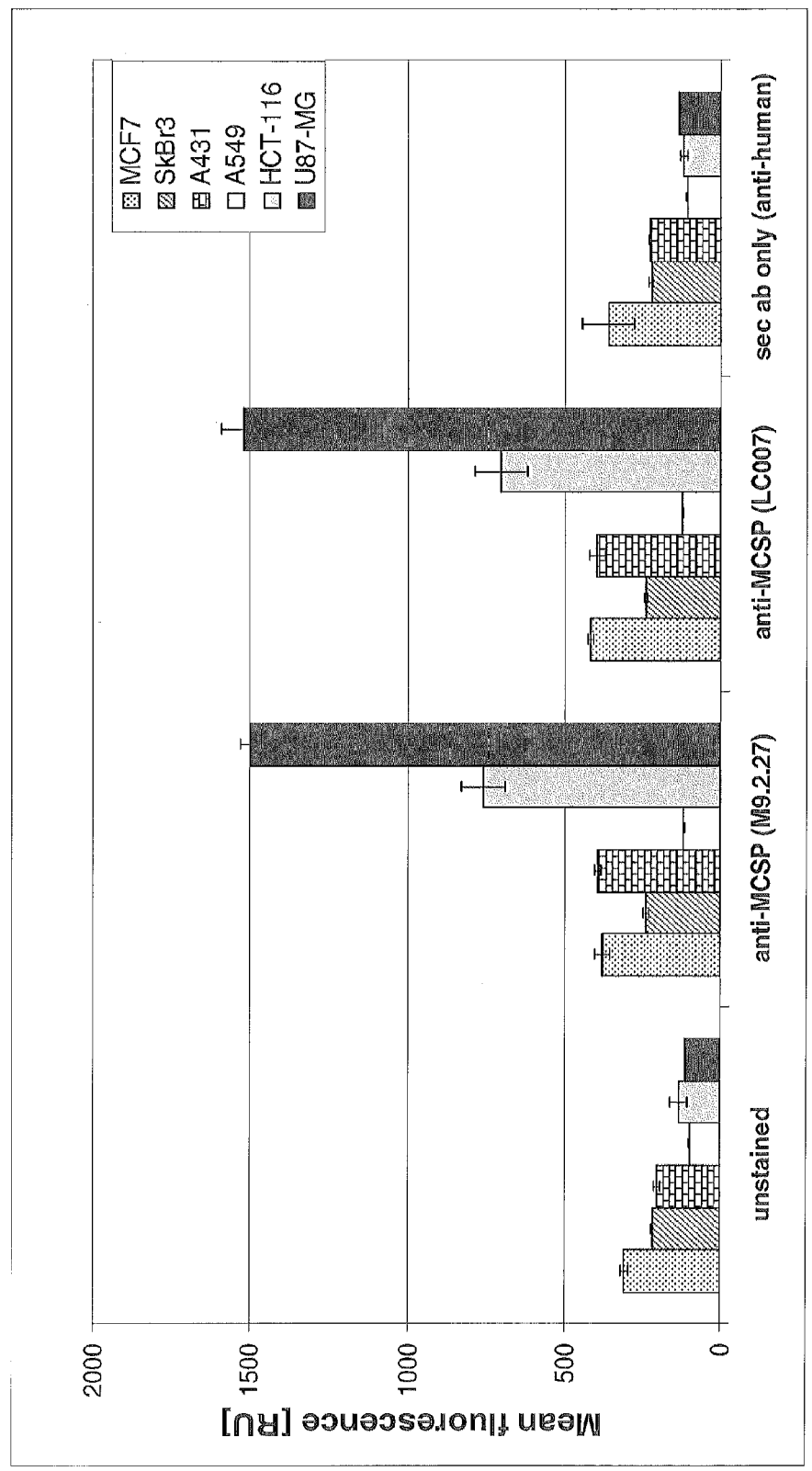
FIG. 12: FACS binding analysis for determination of surface expression levels of MCSP on different cell lines (MCF7, SkBr3, A431, A549, HCT-116 and U87-MG) using two different antibodies. With both antibodies the same levels of MCSP expression could be detected, indicating that U87-MG showed the highest MCSP expression, HCT-116 with a low MCSP expression whereas all other tested cell lines were MCSP negative (in the range of the negative control such as unstained cells).
Figure 13A:
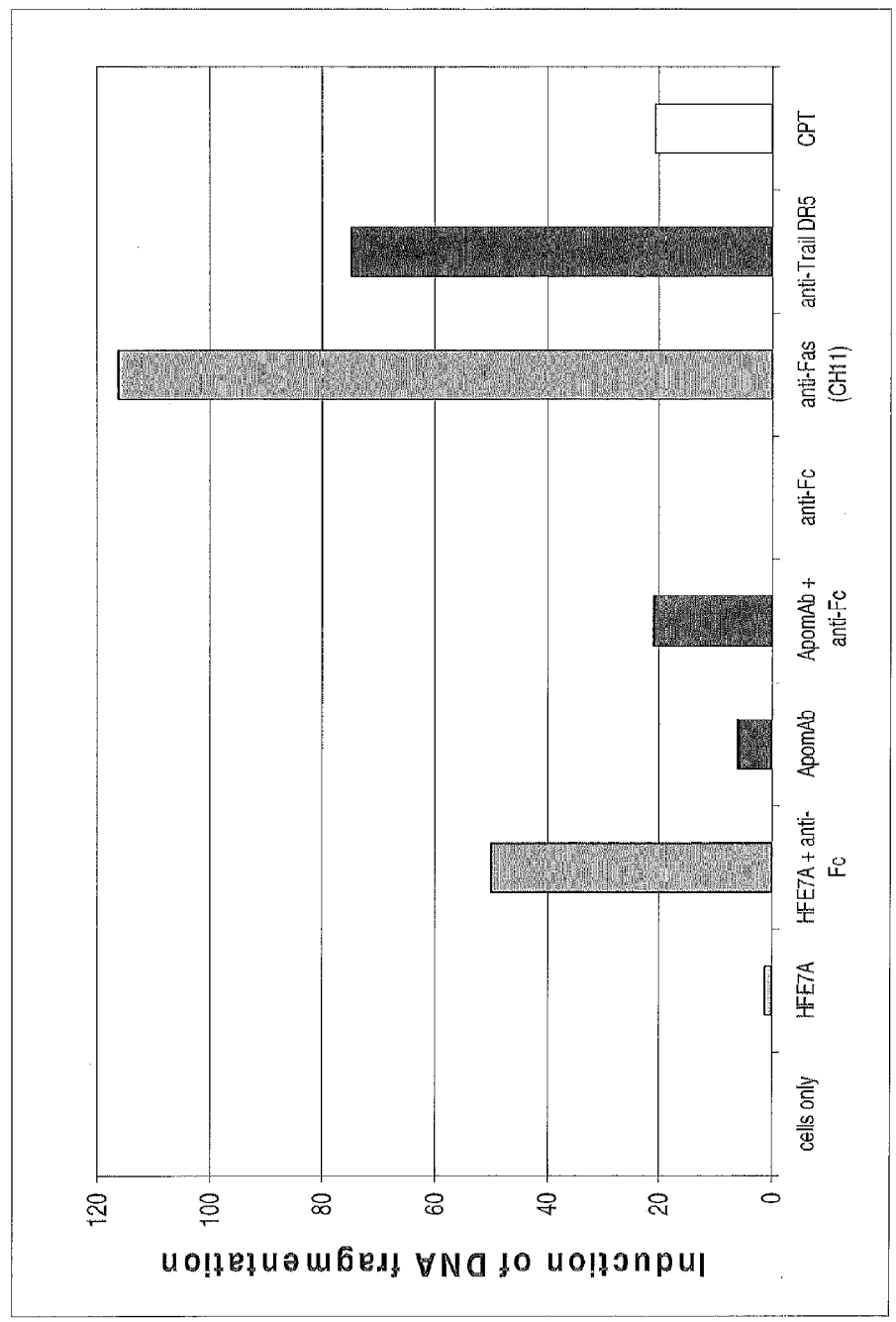
FIG. 13: Evaluation of apoptosis capability of U87-MG (A) and HCT-116 (B) cells using soluble and cross-linked ApomAb (black bars) and HFE7A (grey bars) and the relevant control molecules (anti FAS_CH11, anti DR5_R2 and anti Fc-IgG alone). While in HCT-116 cells apoptosis could only be induced via the DR5 receptor after four hours and not via FAS, this was different for U87-MG cells. Here, significant apoptosis only could be observed after 24 hours. In contrast to HCT-116 cells in U87-MG apoptosis induction by cross-linked HFE7A was twice as efficient as with cross-linked ApomAb. The control antibodies conferring apoptosis already in solution where even more efficient.
Figure 13:
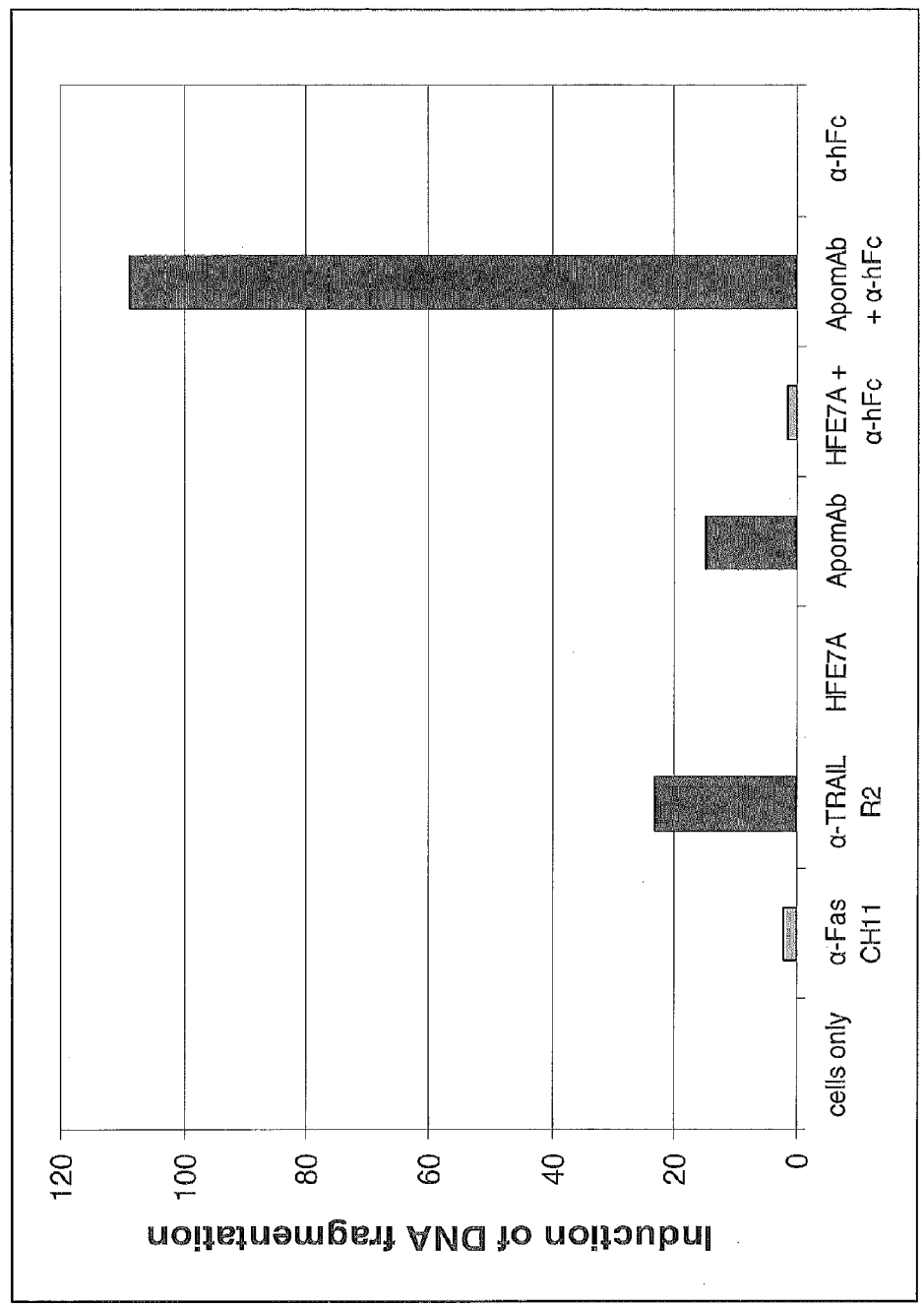

In order to define a cell line that is suitable for analysis of in-vitro apoptosis induction several cell lines were tested for MCSP expression by FACS binding analysis (FIG. 12). Among the tested cell lines only HCT-116 and U-87MG exhibited significant MCSP expression as detected with two anti MCSP antibodies (9.2.27 and LC007). All other cell lines tested showed only very low or no expression of MCSP. For that reason these two cell lines were analyzed if they go into apoptosis when treated with cross-linked agonistic death receptor antibodies or with control antibodies that confer apoptosis already in solution. In U-87MG cells apoptosis could be induced by both, anti FAS and anti DR5 antibodies (FIG. 13A) while this was different for HCT-116 cells. Here apoptosis only could be induced with anti DR5 antibodies (FIG. 13B). Therefore U-87MG cells were chosen to be used as target cells for future apoptosis induction experiments.

Figure 14:
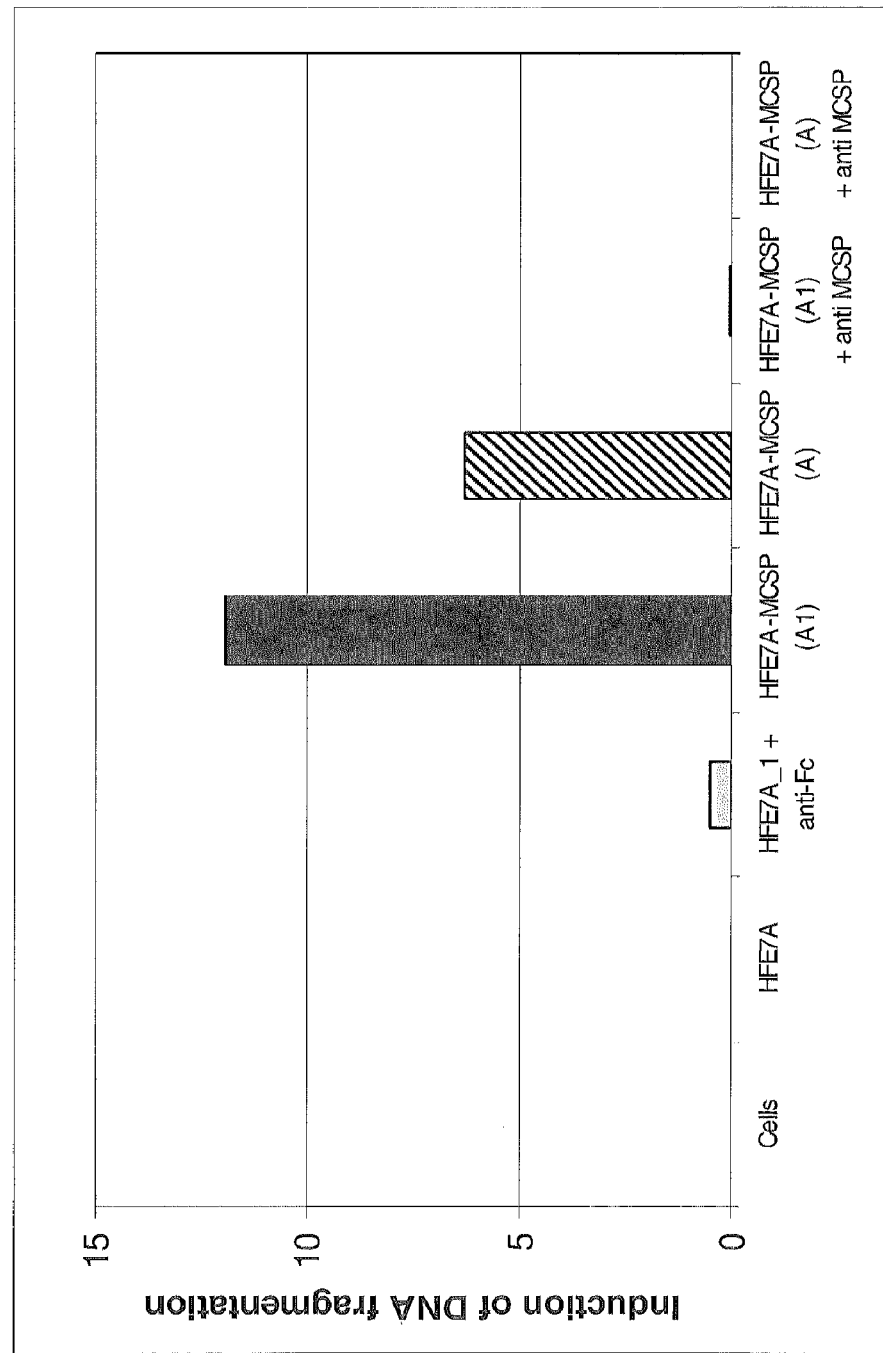
FIG. 14: Analysis of apoptosis induction on U87-MG glioma cells after 24 hours incubation with the bispecific HFE7A-MCSP antibody (mAb 9.2.27) in which either the wild type (A format) or disulfide stabilized MCSP scFv (A1 format) is fused to the C-terminus of the heavy chain of ApomAb. In this case the construct containing the disulfide stabilized scFv demonstrated significantly higher apoptosis that the molecule containing the wild type scFv (although the amount of apoptosis measured by DNA fragmentation was relatively low). However, in both cases the induction of apoptosis could be completely abolished by pre-incubation of the cells with an excess of competing MCSP IgG.

FIG. 14 shows the results obtained from apoptosis induction experiments with the glioma cell line U-87MG after treatment with FAS agonistic bispecific antibodies (in a concentration of 1 µg/ml) consisting of FAS targeting HFE7A IgG which is combined with a MCSP binding scFv (9.2.27). Both, the wild type (A format) and the H44/L100 disulfide stabilized scFv (A1 format) were compared to HFE7A alone or HFE7A cross-linked via a secondary anti human Fc antibody. Although, in general induction of apoptosis of these U-87MG cells is rather low (even after 24 hrs incubation) a significant DNA fragmentation can be observed when the bispecific FAS agonistic antibodies are used. In this case the construct containing the disulfide stabilized scFv seems to be superior over the one containing the wild type scFv, and both show much higher apoptosis induction capacity than the cross-linked HFE7A IgG molecule. Pre-incubation of the cells with a 100-fold excess of MCSP (9.2.27) IgG completely inhibited apoptosis induction by the bispecific constructs, indicating that the observed DNA fragmentation/apoptosis in the absence of competing antibody is specific and dependent on cross-linking of FAS via the MCSP antigen.

Example 6

A DR5-FAP Death Receptor Agonistic Bispecific Antibody is Able to Mediate Apoptosis of One Cell Line Via Cross-Linking by a Second Cell Line Another approach of induction of apoptosis by cross-linking of death receptors as DR5 (apart from cross-linking via an antigen expressed by the tumor cell), is targeting the stroma surrounding the tumor. In that case the targeted antigen is not displayed directly by the tumor cells but by a second, different cell type. One example for this kind of antigen would be FAP (fibroblast activation protein). This protein is expressed on activated fibroblast as they are found in the tumor stroma.

To investigate the possibilities of tumor targeted induction of apoptosis using bispecific death receptor agonistic antibodies targeting human DR5 and an antigen from the tumor stroma, bispecific molecules were generated that consist of an IgG1 part that recognizes DR5 and a FAP binding scFv that is fused to the C-terminus of the heavy chain of the antibody. The sequence of the DR5 targeting IgG was taken from the ApomAb sequence as described in US2007/0031414 A1. The sequence of variable heavy and light chain of the FAP binding scFv was taken from a Fab anti FAP molecule isolated by phage display as shown in sequence #1 and 2. The FAP scFv is fused by a (G4S)2 connector to the C-terminus of the anti DR5 IgG heavy chain.

In this kind of setting two different cell lines have to be used for the in-vitro activity assays: one cell line (the target cell line) should express human DR5, has to be apoptosis competent but does not need to express FAP. The second cell line (the effector cell line) has to be apoptosis negative (either by apoptosis resistance or by not expressing DR5) but needs to express FAP on the surface.

Figure 15:
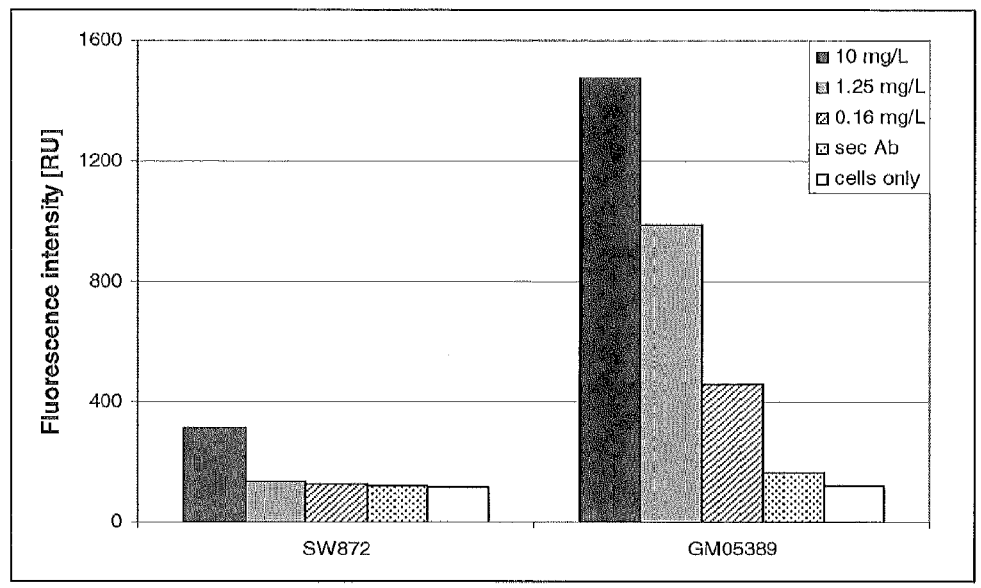
FIG. 15: FACS binding analysis of two different cell lines (SW872 and GM05389) for expression levels of human fibroblast activation protein (FAP) (A). The fluorescence intensity measured with different concentrations of an anti FAP antibody is shown over a range of three magnitudes (black, grey and hatched bars). Negative control reactions as secondary antibody and cells only ate shown as stippled and white bars, respectively. While the GM05389 cells demonstrate expression of FAP over all tested antibody concentrations that was above background, with the SW872 cells FAP expression only could be detected with the highest antibody concentration used (10 µg/ml), indicating that these cells are not suitable for FAP based binding/apoptosis induction experiments. In addition it is shown that this cell line hardly undergo Apo-mAb mediated apoptosis (B). ApomAb alone or another, commercially available anti DR5 antibody did not induce relevant DNA fragmentation. Only when ApomAb is cross-linked with an anti human Fc antibody a detectable low level apoptosis induction can be observed.
Figure 15:
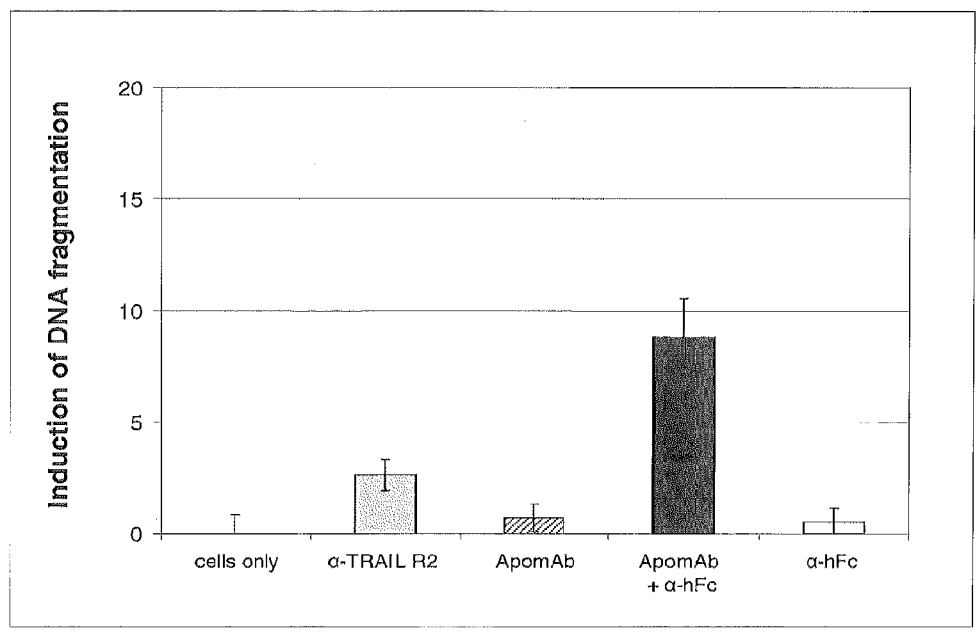

One possible effector cell line that fulfills the desired criteria is the human fibroblast cell line GM05389. As shown in FIG. 15A this cell line expresses significant levels of FAP compared to the cell line SW872 which only showed FAP expression with the highest tested antibody concentration (10 μg/ml) but does not undergo apoptosis by non-cross-linked ApomAb as seen in FIG. 15B. Therefore this cell line seems to be a potential effector cell line in an apoptosis assay where DNA fragmentation of a target cell line is induced by cross-linking via an antigen expressed on a second cell line.

Figure 16:
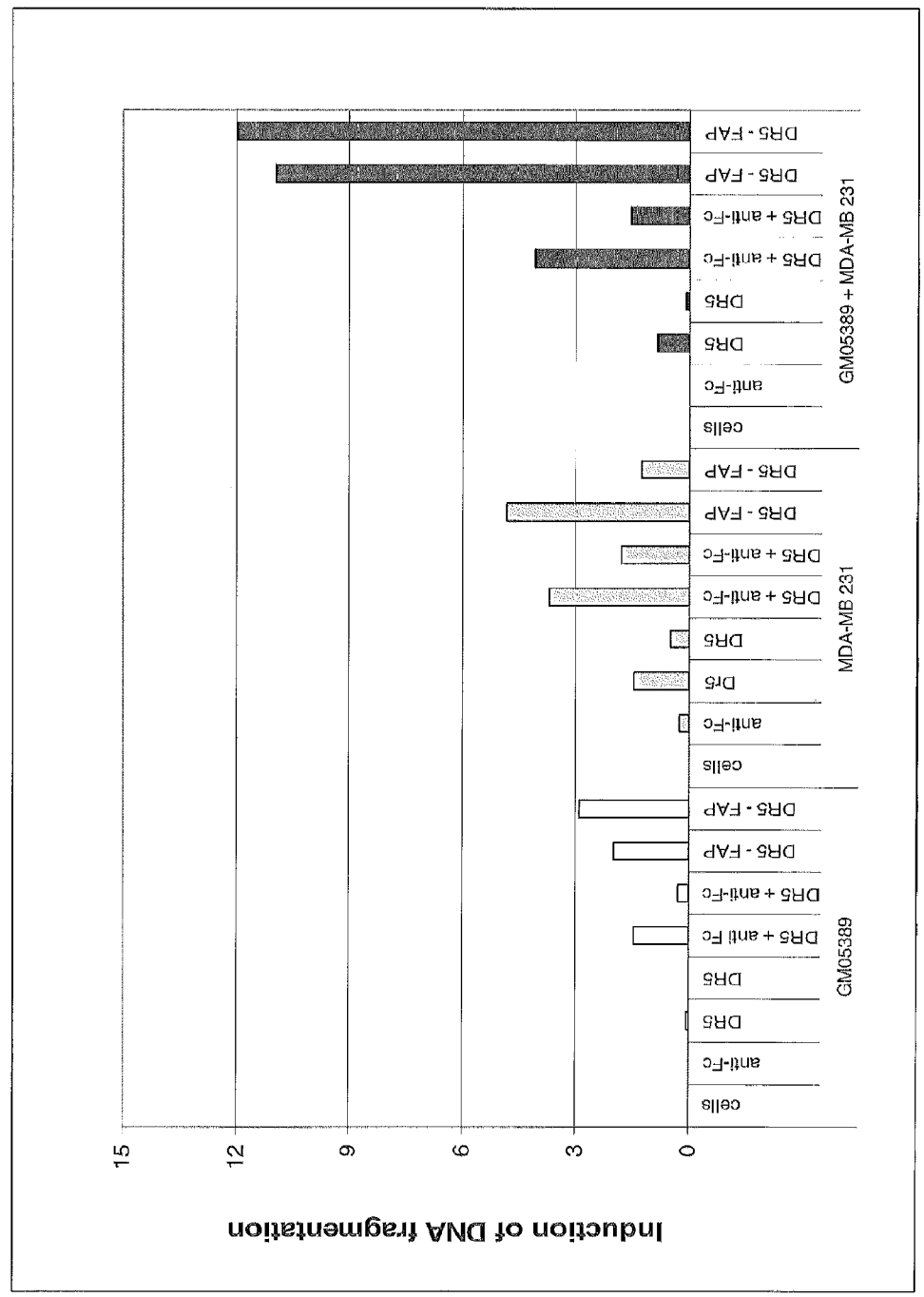
FIG. 16: Analysis of apoptosis induction of GM05389 (white bars) and MDA-MB-231 (grey bars) alone compared to apoptosis induction upon co-cultivation of both cell lines (black bars). In all cell lines ApomAb alone only had a minor effect, while cross-linking of ApomAb resulted in significant apoptosis induction in the MDA-MB-231 cells. Induction of DNA fragmentation with the death receptor agonistic bispecific constructs (ApomAb-FAP) only occurred in high levels when both cell lines are co-cultivated. Here the cross-linking of ApomAb alone did not increase apoptosis in the same range, indicating that for optimal induction of apoptosis two cell lines are necessary: one expressing the death receptor and a second one expressing the FAP antigen.

As a target cell line the human breast-adenocarcinoma cell line MDA-MB-231 was used that expresses low levels of DR5 and is sensitive to DR5 mediated apoptosis induction. In FIG. 16 the results of induction of DNA fragmentation of GM05389 cells and MDA-MB-231 cells compared to the combination of both cell lines by tumor targeted cross-linking of DR5 via FAP is summarized. A significant apoptosis induction after incubation with death receptor agonistic antibodies only can be observed when both cell lines are co-cultivated (black bars) while apoptosis by cross-linking of DR5 with an anti human Fc targeting ApomAb can be detected to a lower degree in both cell lines separately (white and grey bars, respectively). We interpret this result in a way that the DR5 receptors on MDA-MB-231 cells are cross-linked upon binding to the FAP antigen expressed by the fibroblast cell line GM05389.

Example 7

Fusion of CEA Single Chain Fab Molecules (scFab) to ApomAb for the Generation of DR5-CEA Bispecific Agonistic Antibodies Besides the stabilization of bispecific antibodies by defined insertion of internal cysteine residues in the variable heavy and variable light chain of scFv's to prevent aggregate formation, the use of single chain Fab's (scFab's) is another possible strategy to stabilize the entire bispecific antibody to avoid non-specific cross-linking.

To evaluate if this format (scFab fused to DR5 agonistic antibody) exhibits similar apoptosis induction activity as the corresponding scFv containing molecules, different bispecific antibodies in which a CEA scFab was fused to the C-terminus of either the heavy or light chain of ApomAb, were generated by standard recombinant DNA technology.

The orientation of the different domains of the scFab's is as follows: VL-CL-VH-CH1. The C-terminus of the constant light chain (CL) is connected to the N-terminus of the variable heavy chain (VH) via a 34 mer peptide linker. Fusion of the scFab occurs by a G4S connector (either 2 mer or 4 mer).

Single chain Fab containing bispecific antibodies were generated in two basically different formats: in one format two scFab's are fused to the C-terminus of the heavy or light chain of ApomAb (bispecific, tetravalent homodimeric molecules). On the other hand a bispecific molecule was constructed in which only one scFab is fused to the C-terminus of only one ApomAb heavy chain (bispecific, trivalent heterodimeric molecule). This heterodimerization was achieved by using the so-called knob into holes technology which uses Fc mutations that only allow formation of heterodimeric IgG molecules.

Figure 17:
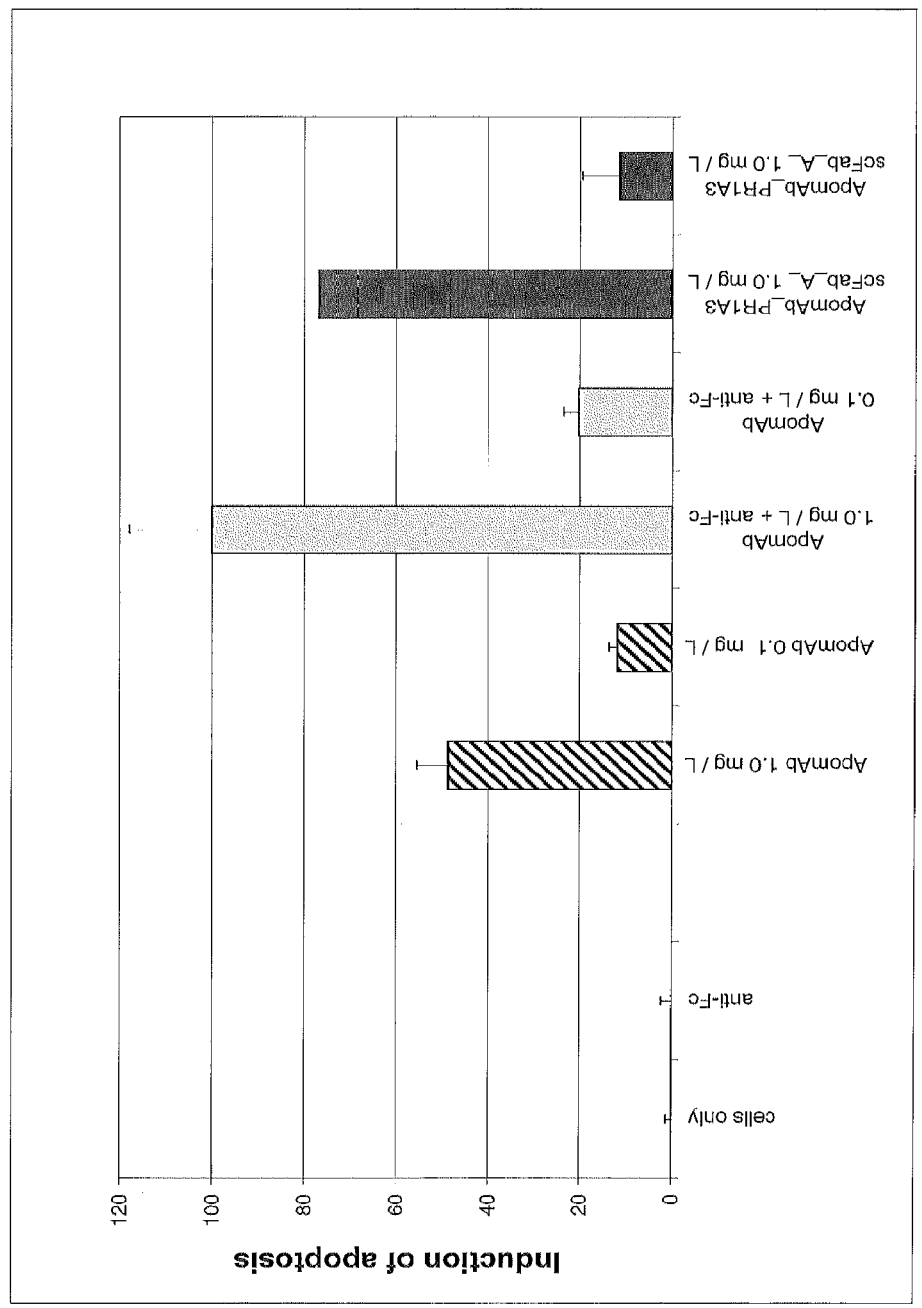
FIG. 17: Results of apoptosis induction assay (24 hrs) on MKN-45 cells with tetravalent bispecific ApomAb_PR1A3_scFab molecules in which the scFab is fused to the C-terminus of the heavy chain of ApomAb (A format). Apoptosis induction is compared to ApomAb (+/− cross-linking with 10 fold excess of anti-human-Fc-antibody) and negative controls. All constructs were used at concentrations of 0.1 and 1.0 µg/ml. Under the used assay conditions the bispecific ApomAb_PR1A3_scFab construct (black bars) clearly shows a concentration dependent induction of apoptosis which is in the same range as observed with hyper-cross-linked Apo-mAb (grey bars) and which is significantly higher as with ApomAb alone (hatched bars).

In FIG. 17 the results of apoptosis induction experiments in which ApomAb_PR1A3_scFab is compared to ApomAb or hyper-cross-linked ApomAb are shown. In this assay the gastric cancer cell line MKN-45 was used and apoptosis was measured after 24 hrs using a DNA fragmentation assay. Clearly, the bispecific construct exhibits apoptosis induction activity that is in the same range as can be observed with ApomAb that was cross-linked via an anti Fc antibody, and which is significantly higher as with the ApomAb alone. However, the apoptosis induction with ApomAb on its own is rather high, which most probably is due to the elongated incubation time of 24 hrs which is necessary to demonstrate maximum apoptosis induction on the used MKN-45 cell line (in contrast to e.g. LS174T cells with which the assay is only run for four hrs).

Figure 18:
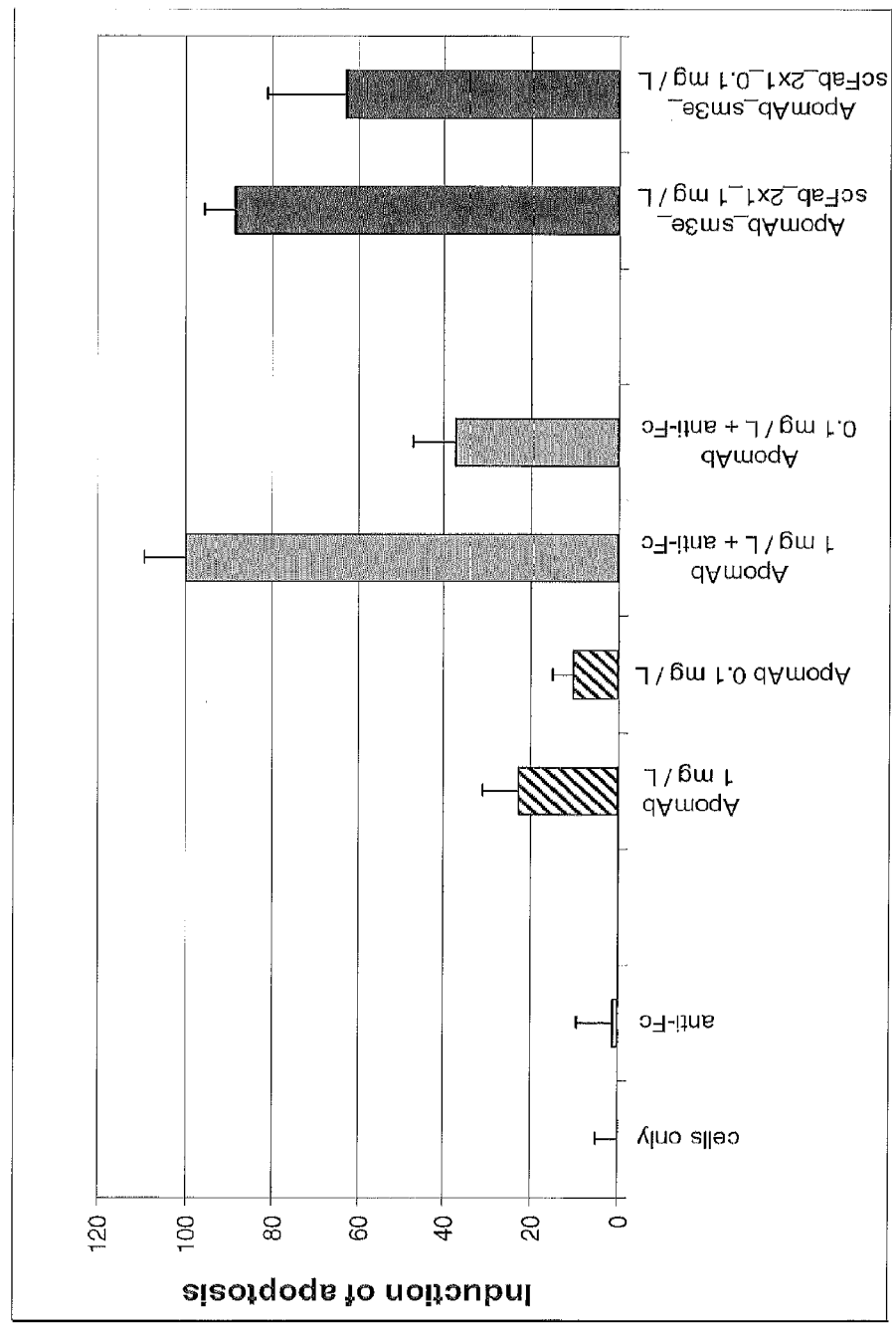
FIG. 18: Analysis of apoptosis induction of LS 174T cells by ApomAb (alone, hatched bars or hyper-cross-linked, grey bars) compared to bispecific trivalent constructs (ApomAb_sm3e_scFab; 2×1 valency, black bars) and negative controls. The assay was performed for 4 hrs using the constructs in concentrations of 0.1 and 1.0 µg/ml. The bispecific Apo-mAb_sm3e_scFab construct is able to induce apoptosis in a concentration dependent manner in the same range as hyper-cross-linked ApomAb does.

To evaluate if bispecific, trivalent DR5 agonistic antibodies (monovalent for the tumor target, CEA, and bivalent for DR5) also are able to induce tumor targeted apoptosis, a molecule was generated in which a CEA scFab (sm3e specificity) was fused to the C-terminus of the ApomAb heavy chain (containing the knob mutation). This heavy chain was co-expressed with the corresponding ApomAb heavy chain containing the 'hole' mutations and the ApomAb light chain. The results of the 4 hrs apoptosis induction assay in which the bispecific, trivalent molecule was analyzed on LS 174T cells (in concentrations of 0.1 and 1.0 μg/ml) are summarized in FIG. 18. From these results it is obvious that also the described trivalent format is able to induce targeted apoptosis in the same range as hyper-cross-linked ApomAb does. At a lower concentration the bispecific format even seems to be slightly more active as ApomAb upon cross-linking.

Example 8

DR5-CEA Bispecific Agonistic Antibody with Superior in-vivo Efficacy Compared to ApomAb For evaluation if the apoptotic activity of the death receptor agonistic antibodies that has been demonstrated in-vitro also translates into superior in-vivo efficacy an in-vivo experiment using the human colon carcinoma cell line LS174T as a model was set up.

In short, at day one of the experiment female SCID beige mice were treated with intrasplenic injection of 3×10⁶ tumor cells. At day seven a scout animal was tested for tumor engraftment as a criterion to start with the antibody treatment one day later. The treatment consisted of a series of three injections (each 10 mg/kg, i.v. in intervals of seven days). Each day the animals were analyzed for demonstrating termination criteria.

Figure 19:
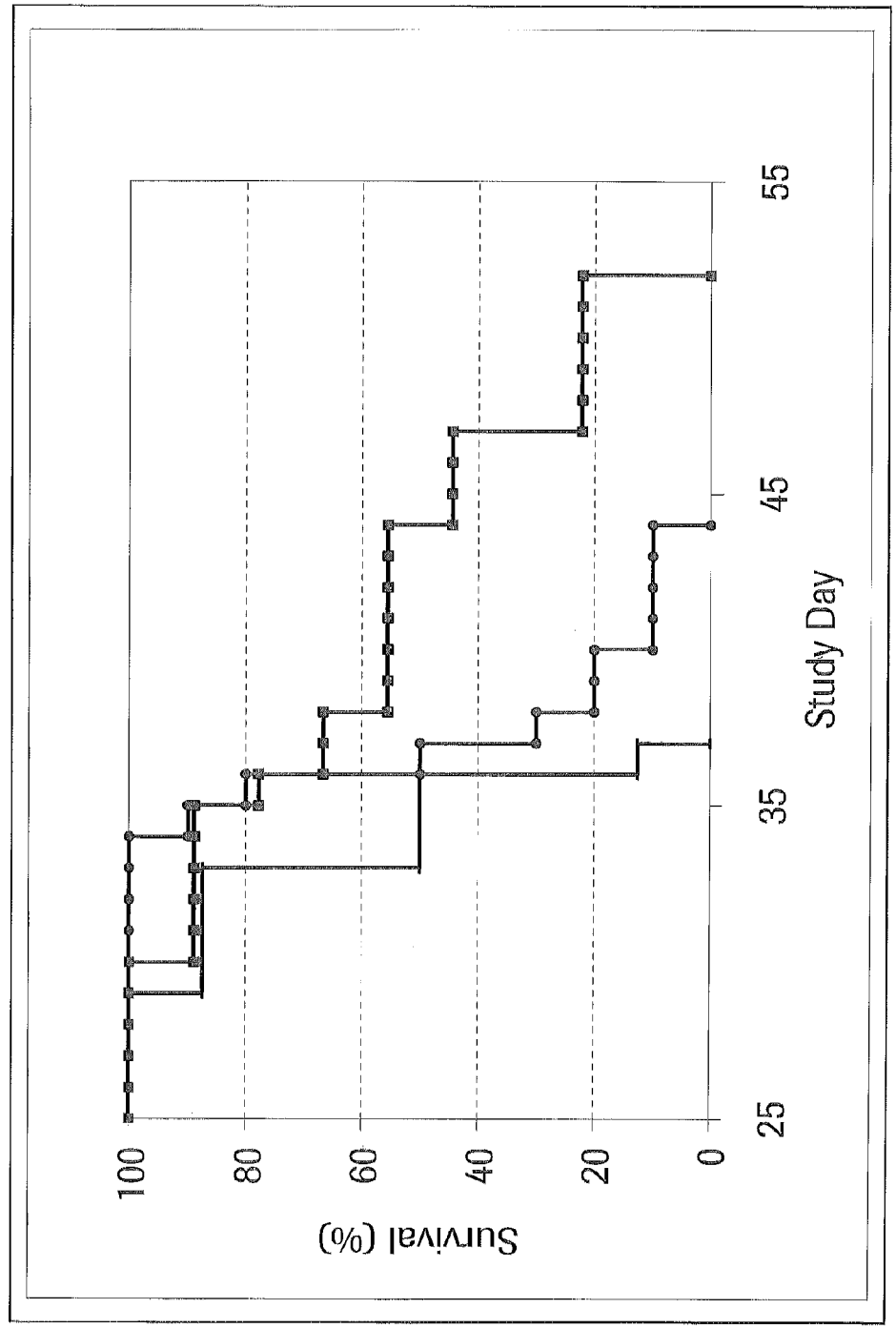
FIG. 19: Analysis of in-vivo efficacy of ApomAb and the bispecific DR5 agonistic antibody ApomAb_sm3e_A1 compared to the vehicle control in an intrasplenic metastatic model using the human colon carcinoma cell line LS 174T. Random groups of ten mice each were treated either with PBS (black line), with ApomAb (black circles) or the ApomAb-sm3e_A1 bispecific antibody (black squares). The percentage of survival is plotted against the time course of the experiment.

FIG. 19 summarizes the results obtained in this in-vivo experiment. Here the survival duration of three groups of mice (each consisting of initially ten animals and treated with different molecules) is compared. While the control group (PBS, black line) was completely terminated 37 days post tumor injection the group treated with ApomAb (filled circles) showed a prolonged survival (maximum of 44 days). The group treated with the bispecific antibody (ApomAb_sm3e_A1, black squares) even showed longer survival (52 days) than the group that had obtained ApomAb alone. Mathematical analysis of the obtained data demonstrated that these results are statistically significant (with p-values below 0.05) meaning that ApomAb showed in-vivo efficacy compared to the PBS control and that the bispecific ApomAb_sm3e_A1 demonstrated superior in-vivo efficacy even compared to ApomAb.

Material and Methods:
Transfection HEK293 EBNA Cells

All (bispecific) antibodies used herein were transiently produced in HEK 293 EBNA cells using a Ca$^{2+}$-phosphate dependent co-transfection procedure for heavy and light chain vectors as described below.

The cells were grown in standard DMEM medium (Invitrogen) containing 10% FCS (Gibco, #16000) at 37° C. in humidified incubators with 5% CO2 atmosphere. 48 hrs prior to transfection 3×10⁷ cells were inoculated in 200 ml DMEM/10% FCS in roller bottles (Falcon #353069, 1400 cm²) and were incubated at 37° C. in a roller bottle incubator (0.3 rpm). For transfection 880 µg total DNA (440 µg for each, heavy and light chain vector)+4.4 ml CaCl$_2$ were filled up with H$_2$O to a total volume of 8.8 ml. The solution was mixed shortly. After mixing 8.8 ml of 1.5 mM phosphate buffer (50 mM Hepes, 280 mM NaCl, 1.5 mM NaH$_2$PO$_4$; pH7.05) were added for DNA precipitation. After additional mixing for ten seconds and short incubation at room temperature (20 seconds) 200 ml of DMEM/2% FCS was added to the DNA solution. The medium/DNA solution was used to replace the original medium in the roller bottle to transfect the cells. After 48 hrs incubation at 37° C. the transfection medium was replaced by 200 ml DMEM/10% FCS and antibody production was continued for 7 days.

After production the supernatants were harvested and the antibody containing supernatants were filtered through 0.22 µm sterile filters and stored at 4° C. until purification.

Purification

The proteins were produced by transient expression in HEK293 EBNA cells. All bispecific molecules described here were purified in two steps using standard procedures, such as protein A affinity purification (Äkta Explorer) and size exclusion chromatography.

The supernatant was adjusted to pH 8.0 (using 2 M TRIS pH 8.0) and applied to Mabselect Sure resin (GE Healthcare) packed in a Tricorn™ 5/50 column (GE Healthcare, column volume (cv)=1 ml) equilibrated with buffer A (50 mM sodiumphosphate, pH 7.0, 250 mM NaCl). After washing with 10 column volumes (cv) of buffer A, 20 cv of buffer B (50 mM sodiumphosphate, pH 7.0, 1 M NaCl) and again 10 cv of buffer A, the protein was eluted using a pH-step gradient to buffer B (50 mM sodiumphosphate, 50 mM sodiumcitrate pH 3.0, 250 mM NaCl) over 20 cv. Fractions containing the protein were pooled and the pH of the solution was gently adjusted to pH 6.0 (using 2 M TRIS pH 8.0). Samples were concentrated to 2 ml using ultra-concentrators (Vivaspin 15R 30.000 MWCO HY, Sartorius) and subsequently applied to a HiLoad™ 16/60 Superdex™ 200 preparative grade (GE Healthcare) equilibrated with 20 mM Histidine, pH 6.0, 150 mM NaCl. The aggregate content of eluted fractions was analyzed by analytical size exclusion chromatography. Therefore 50 µl of each fraction was load to a Superdex™ 200 10/300 GL column (GE Healthcare) equilibrated with 2 mM MOPS, pH 7.4, 150 mM NaCl, 0.02% w/v NaN$_3$. Fractions containing less than 2% oligomers were pooled and concentrated to final concentration of 1-1.5 mg/ml using ultra concentrators (Vivaspin 15R 30.000 MWCO HY, Sartorius). Purified proteins were frozen in liquid N$_2$ and stored at −80° C.

FACS Binding Analysis

All used target cell lines were analyzed for relative expression levels of tumor-related antigens and FAS or DR5 death receptors before apoptosis assays were performed.

Number and viability of cells was determined. For this, adherently growing cells were detached with cell dissociation buffer (Gibco-Invitrogen #13151-014). Cells were harvested by centrifugation (4 min, 400×g), washed with FACS buffer (PBS/0.1% BSA) and the cell number was adjusted to 1.111×10⁶ cells/ml in FACS buffer. 180 µl of this cell suspension was used per well of a 96 well round bottom plate, resulting in 2×10⁵ cell per well. The cells were incubated for 30 min at 4° C. with the first antibody in appropriate dilution. Then the cells were harvested by centrifugation (4 min, 400×g), supernatant was completely removed and cells were washed once with 150 µl of FACS buffer. The cells were resuspended in 150 µl FACS buffer and incubated with the secondary antibody (in case unlabelled first antibody was used) for 30 min at 4° C. in the dark. After two washing steps with FACS buffer cells were resuspended in 200 µl of FACS buffer and analyzed in a HTS FACSCanto II (BD, Software FACS Diva). Alternatively the cells could be fixed with of 200 µl of 2% PFA (paraformaldehyde) in FACS buffer for 20 min at 4° C. and analyzed later. All assays were performed in triplicates.

Used antibodies and concentrations:

| Antibody | Source | Description | Conc. [mg/ml] | Conc. in test [µg/ml] |
|---|---|---|---|---|
| 1. First antibodies | | | | |
| anti hu CD95 (FAS) | BD #555671 | mu IgG1, kappa | 0.5 | 5-10 |
| anti hu DR5 (TRAIL R2) | R&D #MAB631 | mu IgG1, clone 71903 | 0.5 | 5-10 |
| anti hu CEA | Abcam #ab11330 | mu IgG1, clone C6G9 | 9.0 | 30 |

| Antibody | Source | Description | Conc. [mg/ml] | Conc. in test [µg/ml] |
|---|---|---|---|---|
| Isotype control | BD #554121 | mu IgG1 clone MOPC1 | | |
| anti hu MCSP | in house (e.g. M9.2.27, LC007) | human(ized)/ chimeric IgG1 | diff. | 30. |
| anti hu CRIPTO | in house (e.g. LC020, H3L2D1) | human(ized)/ chimeric IgG1 | diff. | 30. |
| anti hu ROBO4-PE | R&D #FAB2454P | mu IgG2a | 0.05 | 0.005 |
| Isotype control | BD #555574 | mu IgG2a-PE | 0.05 | 0.005 |
| 2. Secondary antibodies: | | | | |
| goat anti mouse IgG-PE | Serotec# STAR105PE | | 0.1 | |
| (Fab')₂ goat anti humanFc-PE | Jackson Immunoresearch# 109-116-170 | | | |

Biacore Analysis (Surface Plasmon Resonance, SPR)

SPR experiments were performed on a Biacore T100 with HBS-EP (0.01 M HEPES pH 7.4, 0.15 M NaCl, 3 mM EDTA, 0.005% Surfactant P20, GE Healthcare) as running buffer. Direct coupling of 1220, 740 and 300 resonance units (RU), respectively of biotinylated antigen was performed on a Streptavidin chip using the standard method (GE Healthcare). Different concentrations of the bispecific death receptor agonistic antibodies were passed with a flow of 40 µl/min through the flow cells at 278 K for 90 s to record the association phase. The dissociation phase was monitored for 300 s and triggered by switching from the sample solution to HBS-EP. Bulk refractive index differences were corrected for by subtracting the response obtained from a empty Streptavidin surface. Kinetic constants were derived using the Biacore T100 Evaluation Software (vAA, Biacore, Freiburg/Germany), to fit rate equations for 1:1 Langmuir binding by numerical integration. Since the antigen was immobilized the obtained kinetic constants using the 1:1 Langmuir binding by numerical integration are merely given the apparent KD-value or the avidity.

Induction of Apoptosis

For determination of induced apoptosis the Cell Death Detection ELISA PLUS kit from Roche was used. In short, $10^4$ cells per well of a 96-well plate (after detaching, and determination of cell number and viability) were seeded in 200 µl appropriate medium and were incubated over night at 37° C. in a 5% $CO_2$ atmosphere. The next day the medium was replaced by fresh medium containing the apoptosis inducing antibodies, control antibodies and other controls in appropriate concentrations:

The bispecific antibodies were used in a final concentration of 0.01-10 µg/ml; control antibodies were used at 0.5 µg/ml and cross-linking antibodies were used at 100 µg/ml. Competing antibodies were used at a 100 fold excess.

The cells were incubated for 4-24 hrs at 37° C., 5% $CO_2$ to allow induction of apoptosis. The cells were harvested by centrifugation (10 min, 200×g) and incubated for 1 h at room temperature in 200 µl of lysis buffer (supplied by the kit). Intact cells were sedimented by centrifugation (10 min, 200×g) and 20 µl of the supernatant was analyzed according to the manufacturer's recommendations for induction of apoptosis.

While there are shown and described presently preferred embodiments of the invention, it is to be distinctly understood that the invention is not limited thereto but may be otherwise variously embodied and practiced within the scope of the following claims.

What is claimed is:

1. A dimeric bispecific antibody comprising a first antibody specific for death receptor 5 polypeptide (DR5) and a second antibody specific for fibroblast activation protein (FAP) wherein the dimeric bispecific antibody is bivalent for DR5, wherein the bispecific antibody comprises a variant Fc region having a reduced affinity to Fcγ receptors compared to a wildtype Fc region, and further wherein the bispecific antibody induces apoptosis by cross-linking DR5.

2. The dimeric bispecific antibody of claim 1, wherein the first antibody is an Immunoglobulin (Ig) molecule comprising a light chain and a heavy chain and the second antibody is selected from the group consisting of scFv, scFab, Fab or Fv.

3. The dimeric bispecific antibody of claim 2, wherein the second antibody is fused to the N- or C-terminus of the heavy chain of the Ig molecule.

4. The dimeric bispecific antibody of claim 2, wherein the second antibody is fused to the N- or C-terminus of the light chain of the Ig molecule.

5. The dimeric bispecific antibody of claim 2, wherein the Ig molecule is a IgG.

6. The dimeric bispecific antibody of claim 2, wherein the second antibody is fused to the Ig molecule by a peptide linker.

7. The dimeric bispecific antibody of claim 6, wherein the peptide linker has a length of about 10-30 amino acids.

8. The dimeric bispecific antibody of claim 2, wherein the second antibody comprises additional cysteine residues to form disulfide bonds.

9. A pharmaceutical composition comprising the dimeric bispecific antibody of claim 1 and a pharmaceutical carrier.

* * * * *